(12) United States Patent
Noguchi et al.

(10) Patent No.: US 8,816,090 B2
(45) Date of Patent: Aug. 26, 2014

(54) BENZISOXAZOLE DERIVATIVES

(75) Inventors: Hirohide Noguchi, Chita-gun (JP); Isao Sakurada, Chita-gun (JP); Chikara Uchida, Chita-gun (JP); Nobuaki Waizumi, Chita-gun (JP)

(73) Assignee: Pfizer Inc., New York, NY (US)

( * ) Notice: Subject to any disclaimer, the term of this patent is extended or adjusted under 35 U.S.C. 154(b) by 74 days.

(21) Appl. No.: 11/814,588

(22) PCT Filed: Feb. 15, 2006

(86) PCT No.: PCT/IB2006/000313
§ 371 (c)(1),
(2), (4) Date: Jul. 24, 2007

(87) PCT Pub. No.: WO2006/090224
PCT Pub. Date: Aug. 31, 2006

(65) Prior Publication Data
US 2008/0207690 A1    Aug. 28, 2008

Related U.S. Application Data

(60) Provisional application No. 60/656,653, filed on Feb. 25, 2005, provisional application No. 60/715,977, filed on Sep. 9, 2005.

(51) Int. Cl.
*C07D 261/20*  (2006.01)
*A61K 31/4439*  (2006.01)

(52) U.S. Cl.
USPC .......................................... 546/198; 514/321

(58) Field of Classification Search
USPC .......................................... 546/198; 514/321
See application file for complete search history.

(56) References Cited

U.S. PATENT DOCUMENTS

| | | | | |
|---|---|---|---|---|
| 4,352,811 | A * | 10/1982 | Strupczewski et al. | 514/321 |
| 5,100,902 | A * | 3/1992 | Peglion et al. | 514/321 |
| 5,134,147 | A * | 7/1992 | Peglion et al. | 514/300 |
| 5,280,030 | A | 1/1994 | Jegham et al. | 514/322 |
| 5,780,474 | A * | 7/1998 | Peglion et al. | 514/252.19 |
| 6,335,326 | B1 * | 1/2002 | Den Hartog et al. | 514/217.1 |

FOREIGN PATENT DOCUMENTS

| | | | | |
|---|---|---|---|---|
| EP | 0602242 | 6/1994 | .......... | C07D 413/06 |
| WO | WO 9304063 | 3/1993 | .......... | C07D 413/06 |

OTHER PUBLICATIONS

Martin, Yvonne C. et. al. "Do Structurally Similar Molecules Have Similar Biological Activity?" Journal of Medicinal Chemistry 2002, 45, 4350-4358.*
Itoh et. al. "Synthesis and pharmacological evaluation of carboxamide derivatives as selective serotoninergic 5-HT4 receptor agonists." European Journal of Medicinal Chemistry 1999, 34, 977-989.*
Modica et. al. "Design, synthesis and binding properties of novel and selective 5-HT3 and 5-HT4 receptor ligands" European Journal of Medicinal Chemistry 2000, 35, 1065-1079.*
Lopez-Rodriguez et. al. "Benzimidazole Derivatives. Part 1: Synthesis and Structure ActivityRelationships of New Benzimidazole-4-carboxamides and Carboxylates as Potent and Selective 5-HT4 Receptor Antagonists" Bioorganic & Medicinal Chemistry 1999, 7, 2271-2281.*
"Food and Drug Administration Center for Drug Evaluation and Research Gastrointestinal Drugs Advisory Committee (GIDAC)" Nov. 17, 2011.*
International Search Report for PCT/IB2006/000313, 3 pages.
PCT/IB2006/000313 International Preliminary Examining Report, 7 pages.

* cited by examiner

*Primary Examiner* — David K O Dell
(74) *Attorney, Agent, or Firm* — Wenderoth, Lind & Ponack, L.L.P.

(57) ABSTRACT

This invention relates to compounds of the formula (I): wherein A, B, $R^1$, $R^4$, m, and n are each as described herein or a pharmaceutically acceptable salt thereof, and compositions containing such compounds and the use of such compounds in the treatment of a condition mediated by $5\text{-}HT_4$ receptor activity such as, but not limited to, gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageral disease, nausea, central 10 nervous system disease, Alzheimer's disease, cognitive disorder, emesis, migraine, neurological disease, pain, cardiovascular disorders such as cardiac failure and heart arrhythmia, diabetes and apnea syndrome.

10 Claims, No Drawings

BENZISOXAZOLE DERIVATIVES

BACKGROUND OF THE INVENTION

This invention relates to benzisoxazole derivatives. These compounds have selective 5-HT$_4$ receptor agonistic activity. The present invention also relates to a pharmaceutical composition, method of treatment and use, comprising the above derivatives for the treatment of disease conditions mediated by 5-HT$_4$ receptor activity; in particular 5-HT$_4$ receptor agonistic activity.

In general, 5-HT$_4$ receptor agonists are found to be useful for the treatment of a variety of diseases such as gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageral disease, nausea, central nervous system disease, Alzheimer's disease, cognitive disorder, emesis, migraine, neurological disease, pain, cardiovascular disorders, cardiac failure, heart arrhythmia, diabetes, and apnea syndrome (See *TiPs*, 1992, 13, 141; Ford A. P. D. W. et al., *Med. Res. Rev.*, 1993, 13, 633; Gullikson G. W. et al., *Drug Dev. Res.*, 1992, 26, 405; Richard M. Eglen et al, *TiPS*, 1995, 16, 391; Bockaert J. Et al., *CNS Drugs*, 1, 6; Romanelli M. N. et al., *Arzheim Forsch./Drug Res.*, 1993, 43, 913; Kaumann A. et al., *Naunyn-Schmiedeberg's*. 1991, 344, 150; and Romanelli M. N. et al., *Arzheim Forsch./Drug Res.*, 1993, 43, 913).

There are no prior arts that describe compounds with the similar chemical structure and selective 5-HT$_4$ receptor agonistic activity.

Then, benzisoxazole compounds with the similar chemical structure is disclosed in WO93/04063. Especially, a compound represented by the following formula is disclosed as Example 37. However, the compounds are acetylcholine esterase ⟨AChE⟩ inhibitors.

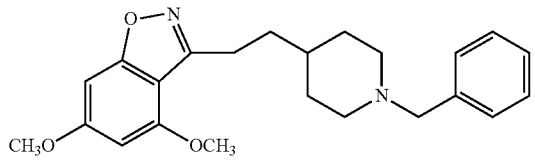

There is a need to provide new 5-HT$_4$ agonists that can be good drugs. In particular, preferred compounds should bind potently to the 5-HT$_4$ receptor whilst they show little affinity for other receptors and show functional activity as agonists. They should be well absorbed from the gastrointestinal tract, be metabolically stable and possess favorable pharmacokinetic properties. When targeted against receptors in the central nervous system they should cross the blood brain barrier freely and when targeted selectively against receptors in the peripheral nervous system they should not cross the blood brain barrier. They should be non-toxic and demonstrate few side-effects. Furthermore, the ideal drug candidate will exist in a physical form that is stable, non-hygroscopic and easily formulated.

SUMMARY OF THE INVENTION

In this invention, it has now surprisingly been found that 4-alkoxy-1,2-benzisoxazole compounds of this invention have selective 5-HT$_4$ agonistic activity, and thus are useful for the treatment of disease conditions mediated by 5-HT$_4$ activity such as gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageral disease, nausea, central nervous system disease, Alzheimer's disease, cognitive disorder, emesis, migraine, neurological disease, pain, cardiovascular disorders, cardiac failure, heart arrhythmia, diabetes and apnea syndrome (especially caused by an opioid administration).

The present invention provides a compound of the following formula (I):

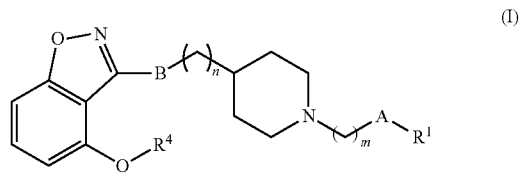

or a pharmaceutically acceptable salt thereof, wherein:

A is —C(R$^2$)(R$^3$)—, or C$_3$-C$_6$ cycloalkylene; said C$_3$-C$_6$ cycloalkylene being unsubstituted or substituted with 1 to 4 substituents independently selected from the group consisting of halogen, hydroxy, C$_1$-C$_4$ alkyl and C$_1$-C$_4$ alkoxy; wherein R$^2$ and R$^3$ are independently selected from the group consisting of halogen and C$_1$-C$_4$ alkyl, wherein said C$_1$-C$_4$ alkyl being unsubstituted or substituted with 1 to 4 substituents independently selected from the group consisting of halogen, hydroxy and C$_1$-C$_4$ alkoxy; or R$^2$ and R$^3$, together with the atom to which they are attached, form a 3-6 membered ring; wherein said ring being unsubstituted or substituted with 1 to 4 substituents independently selected from the group consisting of halogen, hydroxy, C$_1$-C$_4$ alkyl and C$_1$-C$_4$ alkoxy;

B is —O— or —N(H)—;

R$^1$ is carboxy, tetrazolyl, 5-oxo-1,2,4-oxadiazole-3-yl, 5-oxo-1,2,4-thiadiazole-3-yl or hydroxy;

R$^4$ is selected from the group consisting of C$_4$-C$_6$ cycloalkyl, heterocyclyl and —CH$_2$—R$^5$; wherein said C$_4$-C$_6$ cycloalkyl being unsubstituted or substituted with 1 to 4 substituents independently selected from the group consisting of hydroxy, oxo and C$_1$-C$_4$ alkoxy; wherein R$^5$ is selected from the group consisting of trifluoromethyl, isopropyl and C$_4$-C$_6$ cycloalkyl; wherein said C$_4$-C$_6$ cycloalkyl being unsubstituted or substituted with 1 to 4 substituents independently selected from the group consisting of hydroxy, oxo, C$_1$-C$_4$ alkoxy and hydroxy-C$_1$-C$_4$ alkyl;

m is 1 or 2; and n is 1 or 2.

The present invention also provides a compound of formula (I), or a pharmaceutically acceptable salt thereof, each as described herein, for use in the treatment of a condition mediated by 5-HT$_4$ receptor activity; in particular, 5-HT$_4$ agonistic activity.

The present invention also provides a use of a compound of formula (I), or a pharmaceutically acceptable salt thereof, each as described herein, for the manufacture of a medicament for the treatment of a condition mediated by 5-HT$_4$ receptor activity; in particular, 5-HT$_4$ agonistic activity.

The present invention also provides a pharmaceutical composition comprising a compound of formula (I) or a pharmaceutically acceptable salt thereof, each as described herein, together with a pharmaceutically acceptable carrier for said compound.

Further, the present invention provides a method of treatment of a condition mediated by 5-HT$_4$ receptor activity, in a mammalian subject, which comprises administering to a mammal in need of such treatment a therapeutically effective amount of a compound of formula (I) or a pharmaceutically acceptable salt thereof, each as described herein.

Examples of conditions mediated by 5-HT$_4$ receptor activity include, but are not limited to, gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageral disease, nausea, central nervous system disease, Alzheimer's disease, cognitive disorder, emesis, migraine, neurological disease, pain, cardiovascular disorders, cardiac failure, heart arrhythmia, diabetes, and apnea syndrome.

The compounds of the present invention may show less toxicity, good absorption, distribution, good solubility, less protein binding affinity, less drug-drug interaction, and good metabolic stability.

DETAILED DESCRIPTION OF THE INVENTION

In the compounds of the present invention:

Where A is $C_3$-$C_6$ cycloalkylene, this $C_3$-$C_6$ cycloalkylene represents a cyclic divalent hydrocarbon group having 3 to 6 carbon atoms derived from the removal of one hydrogen atom from each of two different carbon atoms in the ring, this $C_3$-$C_6$ cycloalkylene may be cyclopropylene, cyclobutylene, cyclopentylene, and cyclohexylene. Of these, cyclopentylene and cyclohexylene are preferred; cyclohexylene is more preferred.

Where $R^2$ or $R^3$, or the substituent of $C_3$-$C_6$ cycloalkylene or the substituent of a 3-6 membered ring is $C_1$-$C_4$ alkyl, this $C_1$-$C_4$ alkyl may be a straight or branched chain group having one to four carbon atoms, and examples include, but are not limited to, methyl, ethyl, propyl, isopropyl, butyl, isobutyl, sec-butyl, and tert-butyl. Of these, methyl and ethyl are preferred; and methyl is more preferred.

Where the substituent of $R^2$, the substituent of $R^3$, the substituent of $R^4$, the substituent of $R^5$, the substituent of $C_3$-$C_6$ cycloalkylene, or the substituent of a 3-6 membered ring is $C_1$-$C_4$ alkoxy, this $C_1$-$C_4$ alkoxy represents the oxygen atom substituted with said $C_1$-$C_4$ alkyl as defined above, and examples include, but are not limited to, methoxy, ethoxy, propyloxy, isopropyloxy, butoxy, isobutyloxy, sec-butyloxy, and tert-butyloxy. Of these, $C_1$-$C_2$ alkyloxy is preferred; methoxy is more preferred.

Where $R^2$ or $R^3$, or the substituent of $R^2$, the substituent of $R^3$, the substituent of $C_3$-$C_6$ cycloalkylene or the substituent of a 3-6 membered ring is halogen, this halogen may be fluorine, chlorine, bromine, or iodine. Of these, fluorine and chlorine are preferred.

Where $R^2$ and $R^3$, together with the atom to which they are attached, form a 3-6 membered ring, this 3-6 membered ring represents a 3-6 membered carbocyclic ring or a 3-6 membered heterocyclic ring containing at least one heteroatom selected from N, O, and S. Examples of such ring include, but are not limited to, cyclopropyl, cyclobutyl, cyclopentyl, cyclohexyl, tetrahydrofuryl, tetrahydrothienyl, and tetrahydropyranyl, preferably cyclopropyl, cyclobutyl, cyclopentyl, cyclohexyl, and tetrahydropyranyl, and most preferably cyclobutyl, cyclopentyl, cyclohexyl, and tetrahydropyranyl.

Where $R^4$ is $C_4$-$C_6$ cycloalkyl, this $C_4$-$C_6$ cycloalkyl may be cyclobutyl, cyclopentyl, cyclohexyl. Of these, cyclopentyl and cyclohexyl are preferred.

Where $R^4$ is heterocyclyl group, this represents a 3 to 6-membered ring containing at least one hetero atom selected from N, O and S. Examples include, but are not limited to, oxyranyl, 2-pyrrolidinyl, 3-pyrrolidinyl, 3-tetrahydrofuranyl, 2-piperidinyl, 3-piperidinyl, 4-piperidinyl, 1-piperazinyl, 3-tetrahydropyranyl, 4-tetrahydropyranyl. Of these, tetrahydrofuryl, tetrahydrothienyl, and tetrahydropyranyl are preferred. Of these, tetrahydropyranyl is more preferred.

Where the substituent of $R^5$ is hydroxy-$C_1$-$C_4$ alkyl, the $C_1$-$C_4$ alky moiety of the hydroxy-$C_1$-$C_4$ alkyl is as defined above.

The term "treating" and "treatment", as used herein, refers to curative, palliative and prophylactic treatment, including reversing, alleviating, inhibiting the progress of, or preventing the disorder or condition to which such term applies, or one or more symptoms of such disorder or condition.

As used herein, the article "a" or "an" refers to both the singular and plural form of the object to which it refers unless indicated otherwise.

Preferred compounds of the invention are those compounds of formula (I), as set forth above, or a pharmaceutically acceptable salt thereof, in which:

(A) A is —C($R^2$)($R^3$)—, or $C_3$-$C_6$ cycloalkylene; said $R^2$ and $R^3$ are independently selected from the group consisting of halogen or $C_1$-$C_4$ alkyl; or $R^2$ and $R^3$, together with the atom to which they are attached, form a 3-6 membered ring; B is —O— or —N(H)—; $R^1$ is carboxy or hydroxy; $R^4$ is selected from the group consisting of $C_4$-$C_6$ cycloalkyl, heterocyclyl and —CH$_2$—$R^5$; said $C_4$-$C_6$ cycloalkyl being unsubstituted or substituted with 1 to 2 substituents independently selected from the group consisting of hydroxy, oxo, and $C_1$-$C_4$ alkoxy; $R^5$ is selected from the group consisting of trifluoromethyl, isopropyl and $C_4$-$C_6$ cycloalkyl; said $C_4$-$C_6$ cycloalkyl being unsubstituted or substituted with 1 to 2 substituents independently selected from the group consisting of hydroxy, oxo, $C_1$-$C_4$ alkoxy and hydroxy-$C_1$-$C_4$ alkyl; m is 1 or 2; and n is 1;

(B) A is —C($R^2$)($R^3$)—, or

said $R^2$ and $R^3$ are independently selected from the group consisting of halogen or $C_1$-$C_4$ alkyl; or $R^2$ and $R^3$, together with the atom to which they are attached, form a 3-6 membered ring; B is —O— or —N(H)—; $R^1$ is carboxy or hydroxy; $R^4$ is selected from the group consisting of $C_4$-$C_6$ cycloalkyl, heterocyclyl and —CH$_2$—$R^5$; said $C_4$-$C_6$ cycloalkyl being unsubstituted or substituted with 1 to 2 substituents independently selected from the group consisting of hydroxy, oxo, and $C_1$-$C_4$ alkoxy; $R^5$ is selected from the group consisting of trifluoromethyl, isopropyl and $C_4$-$C_6$ cycloalkyl; said $C_4$-$C_6$ cycloalkyl being unsubstituted or substituted with 1 to 2 substituents independently selected from the group consisting of hydroxy, oxo, $C_1$-$C_4$ alkoxy and hydroxy-$C_1$-$C_4$ alkyl; m is 1 or 2; and n is 1;

(C) A is —C($R^2$)($R^3$)—, or

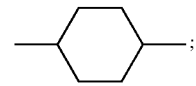

said $R^2$ and $R^3$, together with the atom to which they are attached, form a 3-6 membered ring; B is —O— or —N(H)—; $R^1$ is carboxy or hydroxy; $R^4$ is selected from the group consisting of $C_4$-$C_6$ cycloalkyl, heterocyclyl and —$CH_2$—$R^5$; said $C_4$-$C_6$ cycloalkyl being unsubstituted or substituted with 1 to 2 substituents independently selected from the group consisting of hydroxy, oxo, and $C_1$-$C_4$ alkoxy; $R^5$ is selected from the group consisting of trifluoromethyl, isopropyl and $C_4$-$C_6$ cycloalkyl; said $C_4$-$C_6$ cycloalkyl being unsubstituted or substituted with 1 to 2 substituents independently selected from the group consisting of hydroxy, oxo, $C_1$-$C_4$ alkoxy and hydroxy-$C_1$-$C_4$ alkyl; m is 1 or 2; and n is 1;

(D) A is —$C(R^2)(R^3)$—; $R^2$ and $R^3$ are independently selected from the group consisting of fluoro, methyl, and ethyl; or $R^2$ and $R^3$, together with the atom to which they are attached, form a ring selected from the group consisting of

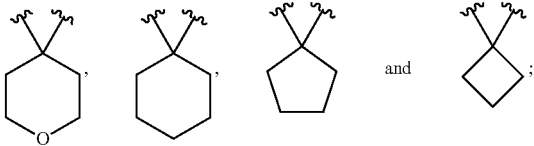

B is —O— or —N(H)—; $R^1$ is carboxy; $R^4$ is selected from the group consisting of $C_4$-$C_6$ cycloalkyl, heterocyclyl and —$CH_2$—$R^5$; said $C_4$-$C_6$ cycloalkyl being unsubstituted or substituted with 1 to 2 substituents independently selected from the group consisting of hydroxy, oxo, and $C_1$-$C_4$ alkoxy; $R^5$ is selected from the group consisting of trifluoromethyl, isopropyl and $C_4$-$C_6$ cycloalkyl; said $C_4$-$C_6$ cycloalkyl being unsubstituted or substituted with 1 to 2 substituents independently selected from the group consisting of hydroxy, oxo, $C_1$-$C_4$ alkoxy and hydroxy-$C_1$-$C_4$ alkyl; m is 1; and n is 1;

(E) A is —$C(R^2)(R^3)$—; $R^2$ and $R^3$ are independently selected from the group consisting of fluoro and methyl; or $R^2$ and $R^3$, together with the atom to which they are attached, form a ring selected from the group consisting of

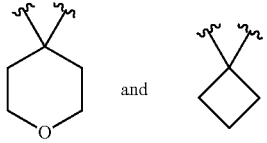 [SMILES: *C1(*)CCOCC1 ; *C1(*)CCC1]

B is —O— or —N(H)—; $R^1$ is carboxy; $R^4$ is selected from the group consisting of $C_4$-$C_6$ cycloalkyl, heterocyclyl and —$CH_2$—$R^5$; said $C_4$-$C_6$ cycloalkyl being unsubstituted or substituted with 1 to 2 substituents independently selected from the group consisting of hydroxy, oxo, and $C_1$-$C_4$ alkoxy; $R^5$ is selected from the group consisting of trifluoromethyl, isopropyl and $C_4$-$C_6$ cycloalkyl; said $C_4$-$C_6$ cycloalkyl being unsubstituted or substituted with 1 to 2 substituents independently selected from the group consisting of hydroxy, oxo, $C_1$-$C_4$ alkoxy and hydroxy-$C_1$-$C_4$ alkyl; m is 1; and n is 1.

Preferred compounds of the invention are those compounds of formula (I), as set forth above, or a pharmaceutically acceptable salt thereof, in which:
(a) A is —$C(R^2)(R^3)$—;
(b) $R^2$ and $R^3$ are independently selected from the group consisting of halogen or $C_1$-$C_4$ alkyl; or $R^2$ and $R^3$, together with the atom to which they are attached, form a 3-6 membered ring; said ring being unsubstituted or substituted with 1 to 4 substituents independently selected from the group consisting of halogen, hydroxy, $C_1$-$C_4$ alkyl, and $C_1$-$C_4$ alkoxy;
(c) $R^2$ and $R^3$, together with the atom to which they are attached, form a 3-6 membered ring; said ring being unsubstituted or substituted with 1 to 4 substituents independently selected from the group consisting of halogen, hydroxy, $C_1$-$C_4$ alkyl, and $C_1$-$C_4$ alkoxy;
(d) $R^2$ and $R^3$, together with the atom to which they are attached, form a 3-6 membered ring;
(e) $R^2$ and $R^3$, together with the atom to which they are attached, form a 4-6 membered ring;
(f) $R^2$ and $R^3$, together with the atom to which they are attached, form a 6 membered ring;
(g) $R^2$ and $R^3$, together with the atom to which they are attached, form

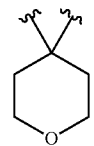

(h) B is —O—;
(i) $R^1$ is carboxy or hydroxy;
(j) $R^1$ is carboxy;
(k) $R^4$ is selected from the group consisting of $C_4$-$C_6$ cycloalkyl, heterocyclyl and —$CH_2$—$R^5$; said $C_4$-$C_6$ cycloalkyl being unsubstituted or substituted with 1 to 2 substituents independently selected from the group consisting of hydroxy, oxo, and $C_1$-$C_4$ alkoxy;
(l) $R^4$ is a group selected from the group consisting of trifluoroethyl, isobutyl, cyclobutylmethyl, cyclopentylmethyl, cyclopentyl, tetrahydro-2H-pyran-4-yl, (1-hydroxycyclopentyl)methyl, 2-hydroxycyclopentyl, 2-methoxycyclopentyl, 2-oxocyclopentyl, 3-hydroxycyclopentyl, 2-hydroxycyclohexyl, 4-hydroxycyclohexyl, 4-(hydroxymethyl)cyclohexyl, [1-(hydroxymethyl)cyclobutyl]methyl and [1-(hydroxymethyl)cyclopentyl]methyl;
(m) $R^5$ is selected from the group consisting of trifluoromethyl, isopropyl and $C_4$-$C_6$ cycloalkyl; said $C_4$-$C_6$ cycloalkyl being unsubstituted or substituted with 1 to 2 substituents independently selected from the group consisting of hydroxy, oxo, $C_1$-$C_4$ alkoxy and hydroxy-$C_1$-$C_4$ alkyl;
(n) $R^5$ is selected from the group consisting of trifluoromethyl, isopropyl, cyclobutyl, cyclopentyl, 1-hydroxycyclopentyl, 1-(hydroxymethyl)cyclobutyl and 1-(hydroxymethyl)cyclopentyl;
(o) $R^5$ is selected from the group consisting of trifluoromethyl, isopropyl and cyclobutyl. Of these classes of compounds, any combination among (a) to (l) is also preferred.

One embodiment of the invention provides a compound selected from the group consisting of:
4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid;
1-{[4-({[4-(2,2,2-Trifluoroethoxy)-1,2-benzisoxazol-3-yl]oxy}methyl)piperidin-1-yl]methyl}cyclobutanecarboxylic acid;
2,2-Dimethyl-3-[4-({[4-(2,2,2-trifluoroethoxy)-1,2-benzisoxazol-3-yl]oxy}methyl)piperidin-1-yl]propanoic acid;
trans-4-{[4-({[4-(2,2,2-Trifluoroethoxy)-1,2-benzisoxazol-3-yl]oxy}methyl)piperidin-1-yl]methyl}cyclohexane carboxylic acid 4-{2-[4-({[4-(2,2,2-Trifluoroethoxy)-1,2-benzisoxazol-3-yl]oxy}methyl)piperidin-1-yl]ethyl}tetrahydro-2H-pyran-4-carboxylic acid;

2,2-Difluoro-3-[4-({[4-(2,2,2-trifluoroethoxy)-1,2-benzisoxazol-3-yl]oxy}methyl)piperidin-1-yl]propanoic acid;

4-{[4-(2-{[4-(2,2,2-Trifluoroethoxy)-1,2-benzisoxazol-3-yl]oxy}ethyl)piperidin-1-yl]methyl}tetrahydro-2H-pyran-4-carboxylic acid;

4-[(4-{[(4-isobutoxy-1,2-benzisoxazol-3-yl)oxy]methyl}piperidin-1-yl)methyl]tetrahydro-2H-pyran-4-carboxylic acid;

1-[(4-{[(4-isobutoxy-1,2-benzisoxazol-3-yl)oxy]methyl}piperidin-1-yl)methyl]cyclobutanecarboxylic acid;

4-[2-(4-{[(4-isobutoxy-1,2-benzisoxazol-3-yl)oxy]methyl}piperidin-1-yl)ethyl]tetrahydro-2H-pyran-4-carboxylic acid;

trans-4-[(4-{[(4-isobutoxy-1,2-benzisoxazol-3-yl)oxy]methyl}piperidin-1-yl)methyl]cyclohexanecarboxylic acid;

4-[(4-{[(4-isobutoxy-1,2-benzisoxazol-3-yl)amino]methyl}piperidin-1-yl)methyl]tetrahydro-2H-pyran-4-carboxylic acid;

4-{[4-({[4-(cyclobutylmethoxy)-1,2-benzisoxazol-3-yl]oxy}methyl)piperidin-1-yl]methyl}tetrahydro-2H-pyran-4-carboxylic acid;

3-[4-({[4-(cyclobutylmethoxy)-1,2-benzisoxazol-3-yl]oxy}methyl)piperidin-1-yl]-2,2-dimethylpropanoic acid; and 4-{[4-({[4-(2,2,2-trifluoroethoxy)-1,2-benzisoxazol-3-yl]amino}methyl)piperidin-1-yl]methyl}tetrahydro-2H-pyran-4-carboxylic acid; or a pharmaceutically acceptable salt thereof.

One embodiment of the invention provides a compound selected from the group consisting of:

4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid;

1-{[4-({[4-(2,2,2-Trifluoroethoxy)-1,2-benzisoxazol-3-yl]oxy}methyl)piperidin-1-yl]methyl}cyclobutanecarboxylic acid;

2,2-Dimethyl-3-[4-({[4-(2,2,2-trifluoroethoxy)-1,2-benzisoxazol-3-yl]oxy}methyl)piperidin-1-yl]propanoic acid;

trans-4-{[4-({[4-(2,2,2-Trifluoroethoxy)-1,2-benzisoxazol-3-yl]oxy}methyl)piperidin-1-yl]methyl}cyclohexane carboxylic acid 4-{2-[4-({[4-(2,2,2-Trifluoroethoxy)-1,2-benzisoxazol-3-yl]oxy}methyl)piperidin-1-yl]ethyl}tetrahydro-2H-pyran-4-carboxylic acid;

4-[(4-{[(4-isobutoxy-1,2-benzisoxazol-3-yl)oxy]methyl}piperidin-1-yl)methyl]tetrahydro-2H-pyran-4-carboxylic acid;

1-[(4-{[(4-isobutoxy-1,2-benzisoxazol-3-yl)oxy]methyl}piperidin-1-yl)methyl]cyclobutanecarboxylic acid;

4-[2-(4-{[(4-isobutoxy-1,2-benzisoxazol-3-yl)oxy]methyl}piperidin-1-yl)ethyl]tetrahydro-2H-pyran-4-carboxylic acid;

trans-4-[(4-{[(4-isobutoxy-1,2-benzisoxazol-3-yl)oxy]methyl}piperidin-1-yl)methyl]cyclohexanecarboxylic acid;

4-[(4-{[(4-isobutoxy-1,2-benzisoxazol-3-yl)amino]methyl}piperidin-1-yl)methyl]tetrahydro-2H-pyran-4-carboxylic acid;

4-{[4-({[4-(cyclobutylmethoxy)-1,2-benzisoxazol-3-yl]oxy}methyl)piperidin-1-yl]methyl}tetrahydro-2H-pyran-4-carboxylic acid;

3-[4-({[4-(cyclobutylmethoxy)-1,2-benzisoxazol-3-yl]oxy}methyl)piperidin-1-yl]-2,2-dimethylpropanoic acid; and 4-{[4-({[4-(2,2,2-trifluoroethoxy)-1,2-benzisoxazol-3-yl]amino}methyl)piperidin-1-yl]methyl}tetrahydro-2H-pyran-4-carboxylic acid; or a pharmaceutically acceptable salt thereof.

Pharmaceutically acceptable salts of a compound of formula (I) include the acid addition and base salts (including disalts) thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate, and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine, and zinc salts.

For a review on suitable salts, see *Handbook of Pharmaceutical Salts: Properties, Selection, and Use* by Stahl and Wermuth (Wiley-VCH, Weinheim, Germany, 2002). A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionisation in the salt may vary from completely ionised to almost non-ionised.

The compounds of the invention may exist in both unsolvated and solvated forms. The term "solvate" is used herein to describe a molecular complex comprising a compound of the invention and one or more pharmaceutically acceptable solvent molecules, for example, ethanol. The term "hydrate" is employed when said solvent is water.

Pharmaceutically acceptable solvates in accordance with the invention include hydrates and solvates wherein the solvent of crystallization may be isotopically substituted, e.g. $D_2O$, $d_6$-acetone, $d_6$-DMSO.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see *J Pharm Sci*, 64 (8), 1269-1288 by Haleblian (August 1975).

Hereinafter all references to a compound of formula (I) include references to salts, solvates and complexes thereof and to solvates and complexes of salts thereof.

The term "compound of the invention" or "compounds of the invention" refers to, unless indicated otherwise, a compound of formula (I) as hereinbefore defined, polymorphs, prodrugs, and isomers thereof (including optical, geometric, and tautomeric isomers) as hereinafter defined and isotopically-labeled compounds of formula (I).

Also within the scope of the invention are so-called "prodrugs" of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as "prodrugs". Further information on the use of prodrugs may be found in *Pro-drugs as Novel Delivery Systems*, Vol. 14, ACS Symposium Series (T Higuchi and W Stella) and *Bioreversible Carriers in Drug Design*, Pergamon Press, 1987 (ed. E B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in *Design of Prodrugs* by H Bundgaard (Elsevier, 1985).

Some examples of prodrugs in accordance with the invention include:
(i) where the compound of formula (I) contains a carboxylic acid functionality
(—COOH), an ester thereof, for example, replacement of the hydrogen with alkyl, acyloxyalkyl, alkoxycarbonyloxyalkyl, phthalidyl or (2-oxo-1,3-dioxolen-4-yl)alkyl groups which may have an alkyl or aryl group at its position;
(ii) where the compound of formula (I) contains an alcohol functionality (—OH), an ether thereof, for example, replacement of the hydrogen with acyloxyalkyl, 1-(alkoxycarbonyloxy)alkyl, phthalidyl and acyloxyalkyloxycarbonyl such as pivaloyloxymethyloxycarbonyl.

Further examples of replacement groups in accordance with the foregoing examples and examples of other prodrug types may be found in the aforementioned references.

Finally, certain compounds of formula (I) may themselves act as prodrugs of other compounds of formula (I).

Compounds of formula (I) containing one or more asymmetric carbon atoms can exist as two or more stereoisomers. Where a compound of formula (I) contains an alkenyl or alkenylene group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art—see, for example, *Stereochemistry of Organic Compounds* by E L Eliel (Wiley, New York, 1994).

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of formula (I), for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. 2H, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

All of the compounds of the formula (I) can be prepared by the procedures described in the general methods presented below or by the specific methods described in the Examples section and the Preparations section, or by routine modifications thereof. The present invention also encompasses any one or more of these processes for preparing the compounds of formula (I), in addition to any novel intermediates used therein.

General Synthesis

The compounds of the present invention may be prepared by a variety of processes well known for the preparation of compounds of this type, for example as shown in the following Methods A to F.

The following Methods A to C illustrate the preparation of compounds of formula (I). Methods D to F illustrate the preparation of various intermediates.

Unless otherwise indicated, A, B, $R^1$, $R^2$, $R^3$, $R^4$, $R^5$, m, and n in the following Methods are as defined above. The term "protecting group", as used hereinafter, means a hydroxy, carboxy, or amino-protecting group which is selected from typical hydroxy, carboxy, or amino-protecting groups described in *Protective Groups in Organic Synthesis* edited by T. W. Greene et al. (John Wiley & Sons, 1999). All starting materials in the following general syntheses may be commercially available or obtained by conventional methods known to those skilled in the art, such as *European Journal of Medicinal Chemistry*, 12(1), 87-91; 1977 and the disclosures of which are incorporated herein by reference.

Method A

This illustrates the preparation of compounds of formula (I).

Reaction Scheme A

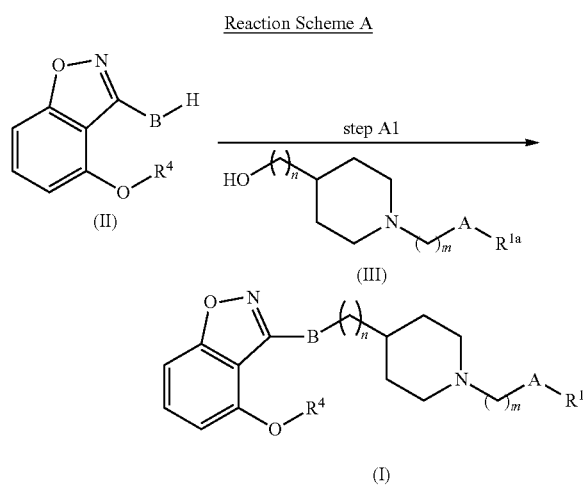

In Reaction Scheme A, $R^{1a}$ is $R^1$ as defined above or a group of formula —COOR$^6$, wherein $R^6$ is a carboxy-protecting group.

The term "carboxy-protecting group", as used herein, signifies a protecting group capable of being cleaved by chemical means, such as hydrogenolysis, hydrolysis, electrolysis, or photolysis, and such carboxy-protecting groups are described in *Protective Groups in Organic Synthesis* edited by T. W. Greene et al. (John Wiley & Sons, 1999). Typical carboxy-protecting groups include, but are not limited to: methyl, ethyl, t-butyl, methoxymethyl, 2,2,2-trichloroethyl, benzyl, diphenylmethyl, trimethylsilyl, t-butyldimethylsilyl and allyl. Of these groups, t-butyl or methyl are preferred.

Step A1

In this step, the desired compound of formula (I) of the present invention is prepared by coupling reaction of the compound of formula (II) with the compound of formula (III). The compound of formula (II) is commercially available or can be prepared according to the methods such as described in *Organic Letteres* 2000, 2(23), 3731-3734 and *J. Heterocyclic Chem.* 1989, 26, 1293. The compound of the formula (III) can be prepared according to Method D to F set forth below.

This reaction is carried out in the presence of reagent(s). There is likewise no particular restriction on the nature of the reagents used, and any reagent commonly used in reactions of this type may equally be used here. Examples of such reagents include but not limited to:

(a) a combination of (a1) dialkyl azodicarboxylate such as diethyl azodicarboxylate (DEAD), dimethyl azodicarboxylate (DMAD) and diisopropyl azodicarboxylate (DIAD) and (a2) trialkylphosphine such as tributylphosphine (TBP) or triarylphosphine such as triphenylphosphine (TPP);

(b) a combination of (b1) tetraalkylazodicarboxamide such as N,N,N',N'-tetraisopropylazodicarboxamide (TIPA) and N,N,N',N'-tetramethylazodicarboxamide (TMAD) and (b2) trialkylphosphine such as tributylphosphine (TBP) or triarylphosphine such as triphenylphosphine (TPP);

(c) phosphorane such as cyanomethylenetributylphosphorane (CMBP), cyanomethylenetrimethylphosphorane and dimethyl (tributylphosphoranylidene)malonate (DMTP).

The coupling reaction can take place over a wide range of temperatures, and the precise reaction temperature is not critical to the invention. The preferred reaction temperature will depend upon such factors as the nature of the solvent, the starting materials and reagents used. It is convenient to carry out the reaction at a temperature of from about −78° C. to about 25° C. for reagents (a) and 50° C. to 100° C. for reagents (b) and (c). The time required for the reaction may also vary widely, depending on many factors, notably the reaction temperature and the nature of the starting materials and solvent employed. However, provided that the reaction is effected under the preferred conditions outlined above, a period of from about 30 minutes to about 24 hours.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but not limited to: aliphatic hydrocarbons, such as hexane, heptane, and petroleum ether; halogenated hydrocarbons, such as dichloromethane, chloroform, carbon tetrachloride, and dichloroethane; ethers, such as diethyl ether, diisopropyl ether, tetrahydrofuran (THF), dimethoxyethane, and dioxane; aromatic hydrocarbons, such as benzene, toluene, xylene, chlorobenzene, dichlorobenzene, and nitrobenzene; amides, such as formamide, N,N-dimethylformamide, N,N-dimethylacetamide, and hexamethylphosphoric triamide; amines, such as N-methylmorpholine, triethylamine, tripropylamine, tributylamine, diisopropylethylamine, pyridine, 4-pyrrolidinopyridine, N,N-dimethylaniline, and N,N-diethylaniline; nitriles, such as acetonitrile and benzonitrile; sulfoxides, such as dimethyl sulfoxide, and sulfolane. Of these solvents, toluene, benzene, xylene, chlorobenzene, dichlorobenzene, THF, diethylether, diisopropylether, dimethoxyethane, acetonitrile, dichloromethane, dichloroethane, and chloroform are preferred.

In the case where $R^{1a}$ is a group of formula —COOR$^6$, the deprotection will follow to yield a carboxy group. This reaction is described in detail by T. W. Greene et al., *Protective Groups in Organic Synthesis*, 369-453, (1999), the disclosures of which are incorporated herein by reference. The following exemplifies a typical reaction involving the protecting group methyl.

The deprotection is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: ethers, such as diethyl ether, diisopropyl ether, tetrahydrofuran (THF), and dioxane, and alcohols such as methanol, ethanol, propanol, isopropanol, and butanol. Of these solvents, THF and methanol are preferred.

The deprotection is carried out in the presence of a base. There is likewise no particular restriction on the nature of the bases used, and any base commonly used in reactions of this type may equally be used here. Examples of such bases include: alkali metal hydroxides, such as lithium hydroxide, sodium hydroxide, potassium hydroxide, and barium hydroxide. Of these, sodium hydroxide and potassium hydroxide are preferred.

The deprotection can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −20° C. to about 120° C., more preferably from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 30 minutes to about 48 hours.

Method B

This illustrates an alternative preparation of the desired compound of formula (I).

Step B1

In this step, the desired compound of formula (V) is prepared by coupling reaction of the compound of formula (II) with the compound of formula (IV) (B1-a), followed by the deprotection of $Pg^1$ (B1-b).

(B1-a) The Coupling Reaction

The coupling reaction is carried out with the similar method described in Step A1.

(B1-b) The Deprotection

This deprotection method is described in detail by T. W. Greene et al. [*Protective Groups in Organic Synthesis*, 494-653, (1999)], the disclosures of which are incorporated herein by reference. The following is a typical method, provided the protecting group is t-butoxycarbonyl.

The deprotection is carried out in the presence of an acid. There is likewise no particular restriction on the nature of the acids used, and any acid commonly used in reactions of this type may equally be used here. Examples of such acids

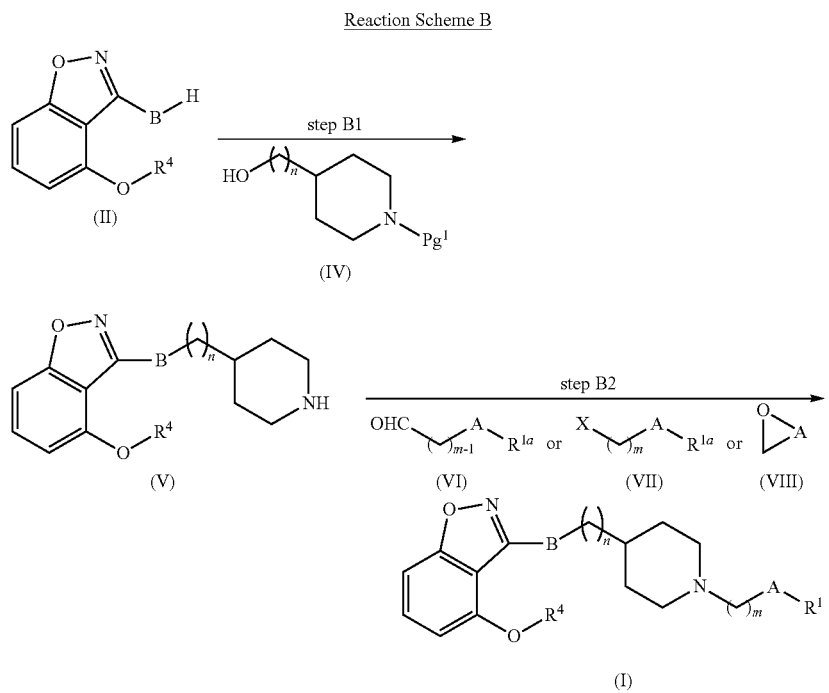

Reaction Scheme B

In Reaction Scheme B, $R^{1a}$ is as defined above and $Pg^1$ is an amino-protecting group and X is a leaving group.

The term "amino-protecting group", as used herein, signifies a protecting group capable of being cleaved by chemical means, such as hydrogenolysis, hydrolysis, electrolysis or photolysis and such amino-protecting groups are described in *Protective Groups in Organic Synthesis* edited by T. W. Greene et al. (John Wiley & Sons, 1999). Typical amino-protecting groups include benzyl, $C_2H_5O(C=O)—$, $CH_3(C=O)—$, benzyloxycarbonyl and t-butoxycarbonyl. Of these groups, t-butoxycarbonyl is preferred.

The term "leaving group", as used herein, signifies a group capable of being substituted by nucleophilic groups, such as a hydroxy group, amines, or carboanions and examples of such leaving groups include halogen atoms, an alkylsulfonyl group and an arylsulfonyl group. Of these, an iodine atom, a metanesulfonyl group, a trifluoromethanesulfonyl group, and 4-methylphenylsulfonyl group are preferred.

include, but are not limited to: acids, such as trifluoroacetic acid and trifluoromethanesulfonic acid, or hydrogen halide such as HCl, HBr, and HI.

The deprotection is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride, and dichloroethane; ethers, such as diethyl ether, diisopropyl ether, tetrahydrofuran (THF), and dioxane, esters such as ethyl acetate, alcohols such as methanol, ethanol, propanol, isopropano, and butanol, water and aromatic hydrocarbons, such as benzene, toluene, and nitrobenzene. Of these solvents, dichloromethane, dichloroethane, chloroform, water, alcohol, THF, and ethyl acetate are preferred.

Step B2

In this step, the desired compound of formula (I) is prepared by employing (B2-a) reductive alkylation, (B2-b) alkylation or (B2-d) alkylation.

(B2-a) Reductive Alkylation

The desired compound of formula (I) is prepared by coupling the compound of formula (V) with the compound of formula (VI).

This reaction is carried out in the presence of a reducing agent. There is likewise no particular restriction on the nature of the reducing agents used, and any reducing agent commonly used in reactions of this type may equally be used here. Examples of such reducing agents include: metal borohydrides such as sodium borohydride, sodium cyanoborohydride and sodium triacetoxyborohydride; a combinations of a hydrogen supplier, such as hydrogen gas and ammonium formate, and a catalyst, such as palladium-carbon, platinum, and Raney nickel; borane reagents, such as boran-tetrahydrofuran complex, boran-dimethyl sulfide complex (BMS), and 9-borabicyclo[3,3,1]nonane (9-BBN). Of these agents, sodium cyanoborohydride and sodium triacetoxyborohydride are preferred.

This reaction is normally and preferably effected in the presence of solvent. There is no particular restriction on the nature of the solvent to be employed, provided that it has no adverse effect on the reaction or the reagents involved and that it can dissolve reagents, at least to some extent.
Examples of suitable solvents include, but not limited to: halogenated hydrocarbons, such as dichloromethane, chloroform, carbon tetrachloride, and dichloroethane; ethers, such as diethyl ether, diisopropyl ether, tetrahydrofuran (THF), and dioxane; aromatic hydrocarbons, such as benzene, toluene, and nitrobenzene; amides, such as formamide, N,N-dimethylformamide, N,N-dimethylacetamide and hexamethylphosphoric triamide; alcohols, such as methanol, ethanol, propanol, isopropanol, and butanol; nitriles, such as acetonitrile and benzonitrile; sulfoxides, such as dimethyl sulfoxide and sulfolane. Of these solvents, dichloromethane, dichloroethane, chloroform, alcohol, and THF are preferred.

This reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −78° C. to about 100° C., more preferably from about 0° C. to about 70° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 48 hours.

(B2-b) Alkylation

The desired compound of formula (I) is prepared by coupling the compound of the formula (V) with the compound of the formula (VII).

The reaction is carried out in the presence of a base. There is likewise no particular restriction on the nature of the bases used, and any base commonly used in reactions of this type may equally be used here. Examples of such bases include: alkali metal hydroxides, such as lithium hydroxide, sodium hydroxide, potassium hydroxide, and barium hydroxide; alkali metal hydrides, such as lithium hydride, sodium hydride, and potassium hydride; alkali metal alkoxides, such as sodium methoxide, sodium ethoxide, and potassium t-butoxide; alkali metal carbonates, such as lithium carbonate, sodium carbonate, potassium carbonate, and cesium carbonate; alkali metal hydrogencarbonates, such as lithium hydrogencarbonate, sodium hydrogencarbonate, and potassium hydrogencarbonate; amines, such as N-methylmorpholine, triethylamine, tripropylamine, tributylamine, diisopropylethylamine, N-methylpiperidine, pyridine, 4-pyrrolidinopyridine, picoline, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO), 1,8-diazabicyclo[5.4.0]undec-7-ene (DBU), lutidine, and colidine; alkali metal amides, such as lithium amide, sodium amide, potassium amide, lithium diiropropyl amide, potassium diisopropyl amide, sodium diiropropyl amide, lithium bis(trimethylsilyl)amide and potassium bis(trimethylsilyl)amide. Of these, triethylamine, diisopropylethylamine, 1,8-diazabicyclo[5.4.0]undec-7-ene (DBU), 1,5-diazabicyclo[4.3.0]non-5-ene (DBN), 1,4-diazabicyclo[2.2.2]octane (DABCO), pyridine, lutidine, colidine, sodium carbonate, sodium hydrogencarbonate, sodium hydroxide, potassium carbonate, potassium hydrogencarbonate, potassium hydroxide, barium hydroxide, and cesium carbonate are preferred.

This reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but not limited to: halogenated hydrocarbons, such as dichloromethane, chloroform, carbon tetrachloride, and dichloroethane; ethers, such as diethyl ether, diisopropyl ether, tetrahydrofuran (THF), and dioxane; aromatic hydrocarbons, such as benzene, toluene and nitrobenzene; amides, such as, N,N-dimethylformamide (DMF), N,N-dimethylacetamide, and hexamethylphosphoric triamide; amines, such as N-methylmorpholine, triethylamine, tripropylamine, tributylamine, diisopropylethylamine, N-methylpiperidine, pyridine, 4-pyrrolidinopyridine, N,N-dimethylaniline, and N,N-diethylaniline; alcohols, such as methanol, ethanol, propanol, isopropanol, and butanol; nitriles, such as acetonitrile and benzonitrile; sulfoxides, such as dimethyl sulfoxide (DMSO) and sulfolane; ketones, such as acetone and diethylketone. Of these solvents, including but not limited to DMF, DMSO, THF, diethylether, diisopropylether, dimethoxyethane, acetonitrile, dichloromethane, dichloroethane and chloroform are preferred.

This reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −20° C. to about 150° C., more preferably from about 0° C. to about 70° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 48 hours.

(B2-c) The Deprotection

In the case where $R^{1a}$ is a group of formula —COOR$^6$, the deprotection will follow to yield a carboxy group by using the similar method described in Step A1.

(B2-d) Alkylation

The desired compound of formula (I), wherein m=1 and $R^1$=OH, is prepared by coupling the compound of the formula (V) with the compound of the formula (VIII).

The reaction is carried out in the presence of a base. There is likewise no particular restriction on the nature of the bases used, and any base commonly used in reactions of this type may equally be used here. Examples of such bases include: alkali metal hydroxides, such as lithium hydroxide, sodium hydroxide, potassium hydroxide, and barium hydroxide; alkali metal hydrides, such as lithium hydride, sodium hydride, and potassium hydride; alkali metal alkoxides, such as sodium methoxide, sodium ethoxide, and potassium t-butoxide; alkali metal carbonates, such as lithium carbonate, sodium carbonate, potassium carbonate, and cesium carbonate; alkali metal hydrogencarbonates, such as lithium hydrogencarbonate, sodium hydrogencarbonate, and potassium hydrogencarbonate; amines, such as N-methylmorpholine, triethylamine, tripropylamine, tributylamine, diisopropylethylamine, N-methylpiperidine, pyridine, 4-pyrrolidinopyridine, picoline, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO), 1,8-diazabicyclo[5.4.0]undec-7-ene (DBU), lutidine, and colidine; alkali metal amides, such as lithium amide, sodium amide, potassium amide, lithium diiropropyl amide, potassium diisopropyl amide, sodium diiropropyl amide, lithium bis(trimethylsilyl)amide and potassium bis(trimethylsilyl)amide. Of these, triethylamine, diisopropylethylamine, 1,8-diazabicyclo[5.4.0]undec-7-ene (DBU), 1,5-diazabicyclo[4.3.0]non-5-ene (DBN), 1,4-diazabicyclo[2.2.2]octane (DABCO), pyridine, lutidine, colidine, sodium carbonate, sodium hydrogencarbonate, potassium carbonate, potassium hydrogencarbonate, and cesium carbonate are preferred.

This reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but not limited to: halogenated hydrocarbons, such as dichloromethane, chloroform; carbon tetrachloride, and dichloroethane; ethers, such as diethyl ether, diisopropyl ether, tetrahydrofuran (THF), and dioxane; aromatic hydrocarbons, such as benzene, toluene and nitrobenzene; amides, such as, N,N-dimethylformamide (DMF), N,N-dimethylacetamide, and hexamethylphosphoric triamide; amines, such as N-methylmorpholine, triethylamine, tripropylamine, tributylamine, diisopropylethylamine, N-methylpiperidine, pyridine, 4-pyrrolidinopyridine, N,N-dimethylaniline, and N,N-diethylaniline; alcohols, such as methanol, ethanol, propanol, isopropanol, and butanol; nitriles, such as acetonitrile and benzonitrile; sulfoxides, such as dimethyl sulfoxide (DMSO) and sulfolane; ketones, such as acetone and diethylketone. Of these solvents, including but not limited to DMF, DMSO, THF, methanol, and ethanol are preferred.

This reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −20° C. to about 150° C., more preferably from about 20° C. to about 70° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 48 hours.

Method C

This illustrates an alternative preparation of the desired compound of formula (I).

Reaction Scheme C

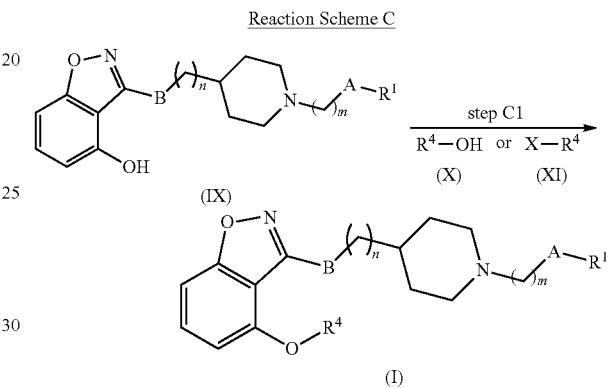

In Reaction Scheme C, X is as defined above.

Step C1

In this step, the desired compound of formula (I) of the present invention is prepared by coupling reaction of the compound of formula (IX) with the compound of formula (X) or (XI). The compound of the formula (IX) can be prepared according to method similar to Method A or B as described above.

(C1-a) The Coupling Reaction with Formula (X)

The coupling reaction is carried out with the similar method described in Step A1.

(C1-b) The Coupling Reaction with Formula (XI)

The coupling reaction is carried out with the similar method described in Step B2-b.

Method D

This illustrates a preparation of the intermediate of formula (III).

Reaction Scheme D

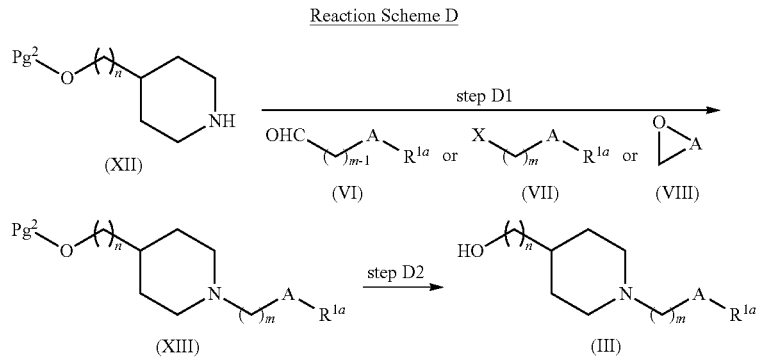

In Reaction Scheme D, Pg$^2$ is a hydroxy-protecting group and R$^{1a}$ and X are as defined above.

The term "hydroxy-protecting group", as used herein, signifies a protecting group capable of being cleaved by chemical means, such as (hydrogenolysis, hydrolysis, electrolysis, or photolysis and such as hydroxy-protecting groups are described in *Protective Groups in Organic Synthesis* edited by T. W. Greene et al. (John Wiley & Sons, 1999). Typical hydroxy-protecting groups include, but not limited to: methyl, CH$_3$OCH$_2$—, CH$_3$SCH$_2$—, benzyl, p-methoxybenzyl, benzoyl, acetyl, trimethylsilyl, triethylsilyl, t-butyldimethylsilyl, and t-butyldiphenylsilyl. Of these groups, t-butyldimethylsilyl and t-butyldiphenylsilyl are preferred.

Step D1

In this step, the desired compound of formula (XIII) is prepared by employing (D1-a) reductive alkylation, (D1-b) alkylation or (D1-c) alkylation.

(D1-a) Reductive Alkylation

The desired compound of formula (XIII) is prepared by coupling reaction of the compound of formula (XII) with the compound of formula (VI) using the similar method described in Step B2-a. The compound of formula (XII) is commercially available or can be prepared according to the methods such as described in *J. Comb. Chem.* 2000, 2, 441 and WO 98/11086.

(D1-b) Alkylation

The desired compound of formula (XIII) is prepared by coupling reaction of the compound of formula (XII) with the compound of formula (VII) using the similar method described in Step B2-b.

(D1-c) Alkylation

The desired compound of formula (XIII), wherein m=1 and R$^{1a}$=OH, is prepared by coupling reaction of the compound of formula (XII) with the compound of formula (VIII) using the similar method described in Step B2-d.

Step D2

In this step, the desired compound of formula (III) is prepared by the deprotection of the compound of formula (XIII).

This deprotection method is described in detail by T. W. Greene et al. [*Protective Groups in Organic Synthesis*, 17-245, (1999)], the disclosures of which are incorporated herein by reference. The following is a typical method, provided the protecting group is t-butyldimethylsilyl.

The deprotection is carried out in the presence of a reagent. There is likewise no particular restriction on the nature of the reagents used, and any reagent commonly used in reactions of this type may equally be used here. Examples of such reagent include, but are not limited to: acids, such as hydrochloric acid, sulfuric acid, hydrobromic acid, trifluoromethanesulfonic acid, toluenesulfonic acid, methanesulfonic acid; and fluorides such as HF, and tetrabutylammonium fluoride (TBAF).

This reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but not limited to: halogenated hydrocarbons, such as dichloromethane, chloroform, carbon tetrachloride, and dichloroethane; ethers, such as diethyl ether, diisopropyl ether, tetrahydrofuran (THF), and dioxane; aromatic hydrocarbons, such as benzene, toluene, xylene, chlorobenzene, dichlorobenzene, and nitrobenzene; amides, such as formamide, N,N-dimethylformamide (DMF), N,N-dimethylacetamide, and hexamethylphosphoric triamide; amines, such as N-methylmorpholine, triethylamine, tripropylamine, tributylamine, diisopropylethylamine, N-methylpiperidine, pyridine, 4-pyrrolidinopyridine, N,N-dimethylaniline and N,N-diethylaniline; alcohols, such as methanol, ethanol, propanol, isopropanol, and butanol; nitriles, such as acetonitrile and benzonitrile;

sulfoxides, such as dimethyl sulfoxide (DMSO) and sulfolane; ketones, such as acetone and diethylketone. Of these solvents, alcohol, THF, diethyl ether, dimethoxyethane, 1,4-dioxane, glyme, diglyme, DMF, DMSO, dichloromethane, dichloroethane, chloroform, carbontetrachloride, benzene, toluene, xylene, chlorobenzene, dichlorobenzene, pyridine, lutidine, colidine, and acetonitrile are preferred.

This reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about –20° C. to about 100° C., more preferably from about 0° C. to about 50° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours.

Method E

This illustrates the preparation of the compound of formula (III) wherein m=1.

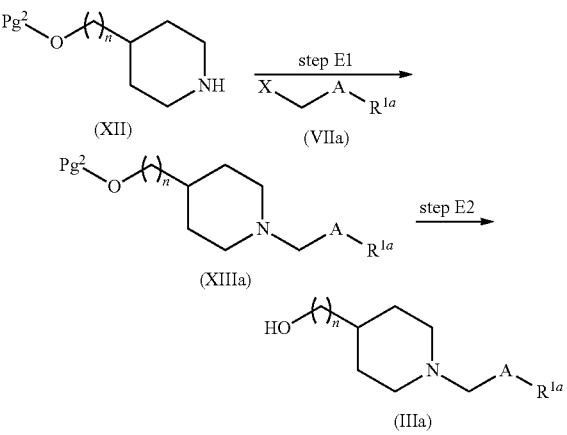

In Reaction Scheme E, Pg$^2$, R$^{1a}$ and X are as defined above.

Step E1

In this step, the compound of formula (XIIIa) is prepared using the compound of formula (XII), 1H-benztriazole-1-methanol and the compound of formula (VIIa) by Katritzky reaction similar to the method that described in *Tetrahedron Lett.*, 1998, 39, 7063-7066.

This reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but not limited to: aliphatic hydrocarbons, such as pentane, hexane, heptane, and petroleum ether; halogenated hydrocarbons, such as dichloromethane, chloroform, carbon tetrachloride, and dichloroethane; ethers, such as diethyl ether, diisopropyl ether, tetrahydrofuran (THF), and dioxane; aromatic hydrocarbons, such as benzene, toluene, xylene, chlorobenzene, dichlorobenzene, and nitrobenzene; amides, such as formamide, N,N-dimethylformamide, N,N-dimethylacetamide, and hexamethylphosphoric triamide; amines, such as N-methylmorpholine, triethylamine, tripropylamine, tributylamine, diisopropylethylamine, N-methylpiperidine, pyridine, 4-pyrrolidinopyridine, N,N-dimethylaniline, and N,N-diethylaniline; alcohols, such as methanol, ethanol, propanol, 2-propanol, butanol, glyme, and diglyme; nitriles, such as acetonitrile and benzonitrile; sulfoxides, such as dimethyl sulfoxide, and sulfolane; ketones, such as acetone and diethylketone. Of these solvents, THF, diethyl ether, diisopropyl ether, dimethoxyethane, glyme, diglyme, acetonitrle, dichlomethane, dichloroethane, chloroform, carbontetrachloride, benzene, toluene, xylene, chlorobenzene, dichlorobenzene, are preferred.

This reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C., more preferably from about 25° C. to about 80° C. The time required for the reaction may also vary widely, depending on many factors, notably the reaction temperature and the nature of the starting materials and solvent employed. However, provided that the reaction is effected under the preferred conditions outlined above, a period of from about 30 minutes to about 6 hours.

Step E2

In this step, the desired compound of formula (IIIa) is prepared by the deprotection of the compound of formula (XIIIa) using the similar method described in Step C2.

Method F

This illustrates the preparation of the compound of formula (IIIb) wherein $R^{1a}$ is —COOR$^6$, A is —C(R$^2$)(R$^3$)— and m=1.

Reaction Scheme F

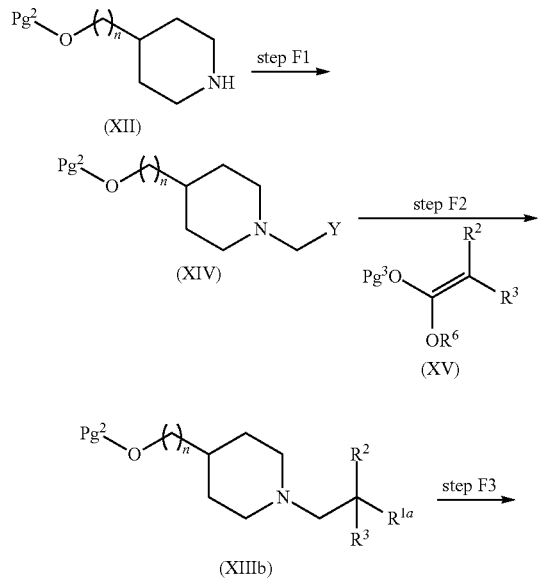

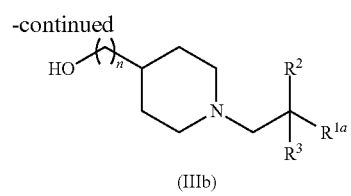

In Reaction scheme F, Pg$^2$ and R$^6$ are as defined above; Pg$^3$ represents a silyl group such as t-butyldimethylsilyl, t-butyldiphenylsilyl, triisopropylsilyl, triethylsilyl or trimethylsilyl; and Y represents an alkoxy group having 1 to 4 carbon atoms, an imidazolyl group or a phtalimidyl group.

Step F1

In this step, the compound of formula (XIV) is prepared by condensation of the compound of formula (XII) with HY in the presence of paraformaldehyde.

In the case Y is an alkoxy group, the reaction is carried out in the presence of base. There is likewise no particular restriction on the nature of the bases used, and any base commonly used in reactions of this type may equally be used here. Examples of such bases include: alkali metal carbonates, such as lithium carbonate, sodium carbonate, potassium carbonate and cesium carbonate; alkali metal hydrogencarbonates, such as lithium hydrogencarbonate, sodium hydrogencarbonate, and potassium hydrogencarbonate; amines, such as N-methylmorpholine, triethylamine, tripropylamine, tributylamine, diisopropylethylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO), 1,8-diazabicyclo[5.4.0]undec-7-ene (DBU), pyridine, lutidine, and colidine; alkali metal amides, such as lithium amide, sodium amide, potassium amide, lithium diiropropyl amide, potassium diisopropyl amide, sodium diiropropyl amide, lithium bis(trimethylsilyl)amide and potassium bis(trimethylsilyl)amide. Of these, triethylamine, diisopropylethylamine, 1,8-diazabicyclo[5.4.0]undec-7-ene (DBU), 1,5-diazabicyclo[4.3.0]non-5-ene (DBN), 1,4-diazabicyclo[2.2.2]octane (DABCO), pyridine, lutidine, colidine, sodium carbonate, sodium hydrogencarbonate, potassium carbonate, potassium hydrogencarbonate, and cesium carbonate are preferred.

In the case Y is not an alkoxy group, the reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: halogenated hydrocarbons, such as dichloromethane, chloroform, carbon tetrachloride, and dichloroethane; ethers, such as diethyl ether, diisopropyl ether, tetrahydrofuran (THF), and dioxane; aromatic hydrocarbons, such as benzene, toluene, xylene, chlorobenzene, dichlorobenzene, and nitrobenzene; amides, such as formamide, N,N-dimethylformamide (DMF), N,N-dimethylacetamide, and hexamethylphosphoric triamide; alcohols, such as methanol, ethanol, propanol, 2-propanol, butanol, glyme, and diglyme; nitriles, such as acetonitrile and benzonitrile; sulfoxides, such as dimethyl sulfoxide, and sulfolane; ketones, such as acetone and diethylketone. Of these solvents, DMF, THF, dichlomethane, methanol are preferred. The reaction can take place over a wide range of temperatures, and the precise reaction temperature is not critical to the invention. The preferred reaction temperature will depend upon such factors as the nature of the solvent, and the starting materials.

However, in general, we find it convenient to carry out the reaction at a temperature of from 0° C. to 70° C. The time required for the reaction may also vary widely, depending on many factors, notably the reaction temperature and the nature of the starting materials and solvent employed. However, provided that the reaction is effected under the preferred conditions outlined above, a period of from 5 minutes to 48 hours, will usually suffice.

Step F2

In this step, the compound of formula (XIIIb) is prepared by Mannich reaction of the compound of formula (XIV) with the compound of formula (XV).

This reaction is normally and preferably effected in the presence of solvent. There is no particular restriction on the nature of the solvent to be employed, provided that it has no adverse effect on the reaction or the reagents involved and that it can dissolve reagents, at least to some extent.

Examples of suitable solvents include, but not limited to: halogenated hydrocarbons, such as dichloromethane, chloroform, carbon tetrachloride, and dichloroethane; ethers, such as diethyl ether, diisopropyl ether, tetrahydrofuran (THF), and dioxane; aromatic hydrocarbons, such as benzene, toluene, xylene, chlorobenzene, dichlorobenzene, and nitrobenzene; amides, such as formamide, N,N-dimethylformamide, N,N-dimethylacetamide and hexamethylphosphoric triamide; amines, such as N-methylmorpholine, triethylamine, tripropylamine, tributylamine, diisopropylethylamine, N-methylpiperidine, pyridine, 4-pyrrolidinopyridine, N,N-dimethylaniline, and N,N-diethylaniline; nitriles, such as acetonitrile and benzonitrile; sulfoxides, such as dimethyl sulfoxide and sulfolane. Of these solvents, THF and acetonitrle are preferred.

The reaction is carried out in the presence of a Lewis acid. There is no particular restriction on the nature of the Lewis acids used, and any Lewis acid commonly used in reactions of this type may equally be used here. Examples of such Lewis acid include: $BF_3$, $AlCl_3$, $FeCl_3$, $AgCl$, $Fe(NO_3)_3$, $Yb(CF_3SO_3)_3$, $SnCl_4$, trimethylsilyl trifluoromethanesulfonate (TMSOTf), $ZnCl_2$, $MgCl_2$, $BF_3.OC_2H_5$, and titanium tetraisopropoxide ($Ti(OPr^i)_4$). Of these, TMSOTf, $ZnCl_2$, $MgCl_2$, $BF_3.OC_2H_5$, and $Ti(OPr^i)_4$ are preferred.

This reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −20° C. to about 100° C., more preferably from about 0° C. to about 50° C. The time required for the reaction may also vary widely, depending on many factors, notably the reaction temperature and the nature of the starting materials and solvent employed. However, provided that the reaction is effected under the preferred conditions outlined above, a period of from about 30 minutes to about 24 hours.

Step F3

In this step, the desired compound of formula (IIIb) is prepared by the deprotection of the compound of formula (XIIIb) using the similar method described in Step C2.

The compounds of formula (I), and the intermediates above-mentioned preparation methods can be isolated and purified by conventional procedures, such as distillation, recrystallization or chromatographic purification.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a pharmaceutical composition or formulation in association with one or more pharmaceutically acceptable carriers or excipients. The term "carrier" or "excipient" is used herein to describe any ingredient other than the compound(s) of the invention. The choice of carrier or excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences*, 19th Edition (Mack Publishing Company, 1995).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as, for example, tablets, capsules containing particulates, liquids, or powders, lozenges (including liquid-filled), chews, multi- and nano-particulates, gels, solid solution, liposome, films (including muco-adhesive), ovules, sprays, and liquid formulations.

Liquid formulations include, for example, suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in *Expert Opinion in Therapeutic Patents*, 11 (6), 981-986 by Liang and Chen (2001).

For tablet dosage forms, depending on dose, the drug may make up from about 1 wt % to about 80 wt % of the dosage form, more typically from about 5 wt % to about 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch, and sodium alginate. Generally, the disintegrant will comprise from about 1 wt % to about 25 wt %, preferably from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose, and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch, and dibasic calcium phosphate dihydrate.

Tablets may also optionally comprise surface active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from about 0.25 wt % to about 10 wt %, preferably from about 0.5 wt % to about 3 wt % of the tablet.

Other possible ingredients include anti-oxidants, colourants, flavouring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in *Pharmaceutical Dosage Forms: Tablets, Vol.* 1, by H. Lieberman and L. Lachman, Marcel Dekker, N.Y., N.Y., 1980 (ISBN 0-8247-6918-X).

Solid formulations for oral administration may be formulated to be immediate and/or modified release. Modified release formulations include delayed-, sustained-, pulsed-, controlled-, targeted, and programmed release.

Suitable modified release formulations for the purposes of the invention are described in U.S. Pat. No. 6,106,864. Details of other suitable release technologies such as high energy dispersions and osmotic and coated particles are to be found in Verma et al, *Pharmaceutical Technology On-line,* 25(2), 1-14 (2001). The use of chewing gum to achieve controlled release is described in WO 00/35298.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, and subcutaneous. Suitable devices for parenteral administration include needle (including microneedle) injectors, needle-free injectors, and infusion techniques.

Parenteral formulations are typically aqueous solutions which may contain excipients such as salts, carbohydrates and buffering agents (preferably to a pH of from about 3 to about 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, *J. Pharm. Sci.,* 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurized container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as I-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from about 1 μg to about 20 mg of the compound of the invention per actuation and the actuation volume may vary from about 1 μl to about 100 μl. A typical formulation may comprise a compound of formula (I), propylene glycol, sterile water, ethanol, and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration. Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted-, and programmed release.

In the case of dry powder inhalers and aerosols, the dosage unit is determined by means of a valve which delivers a metered amount. Units in accordance with the invention are typically arranged to administer a metered dose or "puff" containing from about 1 to about 100 μg of the compound of formula (I). The overall daily dose will typically be in the range about 50 μg to about 20 mg which may be administered in a single dose or, more usually, as divided doses throughout the day.

Rectal/Intravaginal Administration

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular/Aural Administration

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen), and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Kit-of-Parts

Inasmuch as it may be desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules, and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

Dosage

For administration to human patients, the total daily dose of the compounds of the invention is typically in the range of about 0.05 mg to about 100 mg depending, of course, on the mode of administration, preferred in the range of about 0.1 mg to about 50 mg and more preferred in the range of about 0.5 mg to about 20 mg. For example, oral administration may require a total daily dose of from about 1 mg to about 20 mg, while an intravenous dose may only require from about 0.5 mg to about 10 mg. The total daily dose may be administered in single or divided doses.

These dosages are based on an average human subject having a weight of about 65 kg to about 70 kg. The physician will readily be able to determine doses for subjects whose weight falls outside this range, such as infants and the elderly.

As discussed above, a compound of the invention exhibits 5-$HT_4$ agonist activity. A 5-$HT_4$ agonist of the present invention may be usefully combined with at least one other pharmacologically active agent or compound, particularly in the treatment of gastroesophageal reflux disease. For example, a 5-$HT_4$ agonist, particularly a compound of the formula (I), or a pharmaceutically acceptable salt thereof, as defined above, may be administered simultaneously, sequentially or separately in combination with one or more pharmacologically active agents selected from:

(i) histamine $H_2$ receptor antagonists, e.g. ranitidine, lafutidine, nizatidine, cimetidine, famotidine, and roxatidine;

(ii) proton pump inhibitors, e.g. omeprazole, esomeprazole, pantoprazole, rabeprazole, tenatoprazole, ilaprazole, and lansoprazole;

(iii) Acid pump antagonists, e.g. soraprazan, revaprazan(YH-1885), AZD-0865, CS-526, AU-2064, and YJA-20379-8;

(iv) oral antacid mixtures, e.g. Maalox®, Aludrox®, and Gaviscon®;

(v) mucosal protective agents, e.g. polaprezinc, ecabet sodium, rebamipide, teprenone, cetraxate, sucralfate, chloropylline-copper, and plaunotol;

(vi) $GABA_B$ agonists, e.g. baclofen and AZD-3355;

(vii) α2 agonists, e.g. clonidine, medetomidine, lofexidine, moxonidine, tizanidine, guanfacine, guanabenz, talipexole, and dexmedetomidine;

(viii) Xanthin derivatives, e.g. Theophylline, aminophylline and doxofylline;

(ix) calcium channel blockers, e.g. aranidipine, lacidipine, falodipine, azelnidipine, clinidipine, lomerizine, diltiazem, gallopamil, efonidipine, nisoldipine, amlodipine, lercanidipine, bevantolol, nicardipine, isradipine, benidipine, verapamil, nitrendipine, barnidipine, propafenone, manidipine, bepridil, nifedipine, nilvadipine, nimodipine, and fasudil;

(x) benzodiazepine agonists, e.g. diazepam, zaleplon, zolpidem, haloxazolam, clonazepam, prazepam, quazepam, flutazolam, triazolam, lormetazepam, midazolam, tofisopam, clobazam, flunitrazepam, and flutoprazepam;

(xi) prostaglandin analogues, e.g. Prostaglandin, misoprostol, treprostinil, esoprostenol, latanoprost, iloprost, beraprost, enprostil, ibudilast, and ozagrel;

(xii) histamine $H_3$ agonists, e.g. R-alpha-methylhistamine and BP-294;

(xiii) anti-gastric agents, e.g. Anti-gastrin vaccine, itriglumide, and Z-360;

(xiv) 5-$HT_3$ antagonists, e.g. dolasetron, palonosetron, alosetron, azasetron, ramosetron, mitrazapine, granisetron, tropisetron, E-3620, ondansetron, and indisetron;

(xv) tricyclic antidepressants, e.g. imipramine, amitriptyline, clomipramine, amoxapine, and lofepramine;

(xvi) GABA agonists, e.g. gabapentin, topiramate, cinolazepam, clonazepam, progabide, brotizolam, zopiclone, pregabalin, and eszopiclone;

(xvii) opioid analgesics, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine, and pentazocine;

(xviii) somatostatin analogues, e.g. octreotide, AN-238 and PTR-3173;

(xix) Cl Channel activator: e.g. lubiprostone;

(xx) selective serotonin reuptake inhibitors, e.g. sertraline, escitalopram, fluoxetine, nefazodone, fluvoxamine, citalopram, milnacipran, paroxetine, venlafaxine, tramadol, sibutramine, duloxetine, desvenlafaxine, and dapoxetine;

(xxi) anticholinergics, e.g. dicyclomine and hyoscyamine;

(xxii) laxatives, e.g. Trifyba®, Fybogel®, Konsyl®, Isogel®, Regulan®, Celevac®, and Normacol®;

(xxiii) fiber products, e.g. Metamucil®;

(xxiv) antispasmodics, e.g.: mebeverine;

(xxv) dopamine antagonists, e.g. metoclopramide, domperidone, and levosulpiride;

(xxvi) cholinergics, e.g. neostigmine (xxvii) AChE inhibitors, e.g. galantamine, metrifonate, rivastigmine, itopride, and donepezil;

(xxviii) Tachykinin (NK) antagonists, particularly NK-3, NK-2, and NK-1 antagonists e.g. nepadutant, saredutant, talnetant, (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]naphthridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]methyl]-1,2-dihydro-3H-1,2,4-triazol-3-one (MK-869), lanepitant, dapitant and 3-[[2-methoxy-5-(trifluoromethoxy)-phenyl]methylamino]-2-phenyl-piperidine (2S,3S).

Method for Assessing Biological Activities:

The 5-$HT_4$ receptor binding affinities of the compounds of this invention are determined by the following procedures.

Human 5-$HT_4$ Binding (1)

Human 5-$HT_{4(d)}$ transfected HEK293 cells were prepared and grown in-house. The collected cells were suspended in 50 mM HEPES (pH 7.4 at 4° C.) supplemented with protease inhibitor cocktail (Boehringer, 1:1,000 dilution) and homogenized using a hand held Polytron PT 1200 disrupter set at full power for 30 sec on ice. The homogenates were centrifuged at 40,000×g at 4° C. for 30 min. The pellets were then resuspended in 50 mM HEPES (pH 7.4 at 4° C.) and centrifuged once more in the same manner. The final pellets were resuspended in an appropriate volume of 50 mM HEPES (pH 7.4 at 25° C.), homogenized, aliquoted and stored at −80° C. until use. An aliquot of membrane fractions was used for protein concentration determination using BCA protein assay kit (PIERCE) and ARVOsx plate reader (Wallac).

For the binding experiments, 25 μl of test compounds were incubated with 25 μl of [$^3$H]-GR113808 (Amersham, final 0.2 nM) and 150 μl of membrane homogenate and WGA-SPA beads (Amersham) suspension solutions (10 μg protein and 1 mg SPA beads/well) for 60 min at room temperature. Nonspecific binding was determined by 1 μM GR113808 (Tocris) at the final concentration. Incubation was terminated by centrifugation at 1,000 rpm.

Receptor-bound radioactivity was quantified by counting with MicroBeta plate counter (Wallac).

All compounds of Examples showed 5-$HT_4$ receptor affinity.

Human 5-$HT_4$ Binding (2)

Human 5-$HT_{4(d)}$ transfected HEK293 cells were prepared and grown in-house. The collected cells were suspended in 50 mM Tris buffer (pH 7.4 at 4° C.) supplemented with protease inhibitor cocktail (Boehringer, 1:1,000 dilution) and homogenized using a hand held Polytron PT 1200 disrupter set at full power for 30 sec on ice. The homogenates were centrifuged at 40,000×g at 4° C. for 10 min. The pellets were then resuspended in 50 mM Tris buffer (pH 7.4 at 4° C.) and centrifuged once more in the same manner. The final pellets were resuspended in an appropriate volume of 50 mM Tris buffer (pH 7.4 at 25° C.) containing 10 mM $MgCl_2$, homogenized, aliquoted and stored at −80° C. until use. An aliquot of membrane fractions was used for protein concentration determination using BCA protein assay kit (PIERCE) and ARVOsx plate reader (Wallac).

For the binding experiments, 50 μl of test compounds were incubated with 50 μl of [$^3$H] 5-HT (Amersham, final 8.0 nM) and 400 μl of membrane homogenate (300 μg protein/tube) for 60 min at room temperature. Nonspecific binding was determined by 50 μM GR113808 (Tocris) at the final concentration. All incubations were terminated by rapid vacuum filtration over 0.2% PEI soaked glass fiber filter papers using BRANDEL harvester followed by three washes with 50 mM Tris buffer (pH 7.4 at 25° C.). Receptor-bound radioactivity was quantified by liquid scintillation counting using Packard LS counter.

All compounds of Examples showed 5-$HT_4$ receptor affinity.

Agonist-Induced cAMP Elevation in Human 5-$HT_{4(d)}$ Transfected HEK293 Cells

Human 5-$HT_{4(d)}$ transfected HEK293 cells were established in-house. The cells were grown at 37° C. and 5% $CO_2$ in DMEM supplemented with 10% FCS, 20 mM HEPES (pH 7.4), 200 µg/ml hygromycin B (Gibco), 100 units/ml penicillin and 100 µg/ml streptomycin.

The cells were grown to 60-80% confluence. On the previous day before treatment with compounds dialyzed FCS (Gibco) was substituted for normal and the cells were incubated overnight.

Compounds were prepared in 96-well plates (12.5 µl/well). The cells were harvested with PBS/1 mM EDTA, centrifuged and washed with PBS. At the beginning of the assay, cell pellet was resuspended in DMEM supplemented with 20 mM HEPES, 10 µM pargyline (Sigma) and 1 mM 3-isobutyl-1-methylxanthine (Sigma) at the concentration of $1.6 \times 10^5$ cells/ml and left for 15 min at room temperature. The reaction was initiated by addition of the cells into plates (12.5 µl/well). After incubation for 15 min at room temperature, 1% Triton X-100 was added to stop the reaction (25 µl/well) and the plates were left for 30 minutes at room temperature. Homogenous time-resolved fluorescence-based cAMP (Schering) detection was made according to the manufacturer's instruction. ARVOsx multilabel counter (Wallac) was used to measure HTRF (excitation 320 nm, emission 665 nm/620 nm, delay time 50 µs, window time 400 µs).

Data was analyzed based on the ratio of fluorescence intensity of each well at 620 nm and 665 nm followed by cAMP quantification using cAMP standard curve. Enhancement of cAMP production elicited by each compound was normalized to the amount of cAMP produced by 1,000 nM serotonin (Sigma).

All compounds of Examples showed $5\text{-HT}_4$ receptor agonistic activity as shown by the following table.

Agonist-induced cAMP elevation in human $5\text{-HT}_4$

| Example # | $EC_{50}$(nM) | Emax(%) |
|---|---|---|
| 1 | 1.5 | 69 |
| 2 | 0.51 | 47 |
| 3 | 0.69 | 34 |
| 4 | 1.2 | 77 |
| 5 | 2.7 | 70 |
| 6 | 20 | 30 |
| 7 | 48 | 35 |
| 8 | 2.6 | 39 |
| 9 | 2.9 | 36 |
| 10 | 3.1 | 45 |
| 11 | 1.4 | 29 |
| 12 | 2.3 | 45 |
| 13 | 2.7 | 54 |
| 14 | 2.0 | 41 |
| 15 | 39 | 32 |
| 16 | 1.6 | 55 |
| 17 | 3.6 | 41 |
| 18 | 2.0 | 52 |
| 19 | 0.16 | 45 |
| 20 | 0.24 | 50 |
| 21 | 5.3 | 61 |
| 22 | 4.4 | 73 |
| 23 | 22 | 77 |
| 24 | 1.4 | 52 |
| 25 | 3.0 | 41 |
| 26 | 6.5 | 49 |
| 27 | 11 | 71 |
| 28 | 6.6 | 78 |
| 29 | 11 | 70 |
| 30 | 19 | 88 |
| 31 | 27 | 31 |
| 32 | 1.6 | 40 |
| 33 | 3.3 | 51 |
| 34 | 2.7 | 46 |
| 35 | 1.4 | 56 |
| 36 | 1.9 | 52 |
| 37 | 8.8 | 50 |
| 38 | 0.84 | 40 |

Agonist-induced cAMP elevation in human $5\text{-HT}_4$

| Example # | $EC_{50}$(nM) | Emax(%) |
|---|---|---|
| 39 | 1.3 | 56 |
| 40 | 16 | 42 |
| 41 | 3.0 | 44 |
| 42 | 18 | 67 |
| 43 | 3.3 | 49 |
| 44 | 2.4 | 55 |
| 45 | 3.8 | 42 |
| 46 | 5.5 | 45 |
| 47 | 5.3 | 71 |
| 48 | 4.3 | 43 |
| 49 | 65 | 40 |
| 50 | 98 | 50 |
| 51 | 27 | 33 |
| 52 | 30 | 41 |
| 53 | 2.8 | 59 |

Human Dofetilide Binding

Human HERG transfected HEK293S cells were prepared and grown in-house. The collected cells were suspended in 50 mM Tris-HCl (pH 7.4 at 4° C.) and homogenized using a hand held Polytron PT 1200 disruptor set at full power for 20 sec on ice. The homogenates were centrifuged at 48,000×g at 4° C. for 20 min. The pellets were then resuspended, homogenized, and centrifuged once more in the same manner. The final pellets were resuspended in an appropriate volume of 50 mM Tris-HCl, 10 mM KCl, 1 mM $MgCl_2$ (pH 7.4 at 4° C.), homogenized, aliquoted and stored at −80° C. until use. An aliquot of membrane fractions was used for protein concentration determination using BCA protein assay kit (PIERCE) and ARVOsx plate reader (Wallac).

Binding assays were conducted in a total volume of 200 µl in 96-well plates. Twenty µl of test compounds were incubated with 20 µl of [$^3$H]-dofetilide (Amersham, final 5 nM) and 160 µl of membrane homogenate (25 µg protein) for 60 min at room temperature. Nonspecific binding was determined by 10 µM dofetilide at the final concentration. Incubation was terminated by rapid vacuum filtration over 0.5% presoaked GF/B Betaplate filter using Skatron cell harvester with 50 mM Tris-HCl, 10 mM KCl, 1 mM $MgCl_2$, pH 7.4 at 4° C. The filters were dried, put into sample bags and filled with Betaplate Scint. Radioactivity bound to filter was counted with Wallac Betaplate counter.

Caco-2 Permeability

Caco-2 permeability was measured according to the method described in Shiyin Yee, *Pharmaceutical Research*, 763 (1997).

Caco-2 cells were grown on filter supports (Falcon HTS multiwell insert system) for 14 days. Culture medium was removed from both the apical and basolateral compartments and the monolayers were preincubated with pre-warmed 0.3 mL apical buffer and 1.0 mL basolateral buffer for 0.5 hour at 37° C. in a shaker water bath at 50 cycles/min. The apical buffer consisted of Hanks Balanced Salt Solution, 25 mM D-glucose monohydrate, 20 mM MES Biological Buffer, 1.25 mM $CaCl_2$ and 0.5 mM $MgCl_2$ (pH 6.5). The basolateral buffer consisted of Hanks Balanced Salt Solution, 25 mM D-glucose monohydrate, 20 mM HEPES Biological Buffer, 1.25 mM $CaCl_2$ and 0.5 mM $MgCl_2$ (pH 7.4). At the end of the preincubation, the media was removed and test compound solution (10 µM) in buffer was added to the apical compartment. The inserts were moved to wells containing fresh basolateral buffer at 1 h. Drug concentration in the buffer was measured by LC/MS analysis.

Flux rate (F, mass/time) was calculated from the slope of cumulative appearance of substrate on the receiver side and apparent permeability coefficient ($P_{app}$) was calculated from the following equation.

$$P_{app}(cm/sec)=(F*VD)/(SA*MD)$$

where SA is surface area for transport (0.3 cm$^2$), VD is the donor volume (0.3 mL), MD is the total amount of drug on the donor side at t=0. All data represent the mean of 2 inserts. Monolayer integrity was determined by Lucifer Yellow transport.

Half-Life in Human Liver Microsomes (HLM)

Test compounds (1 µM) were incubated with 3.3 mM MgCl$_2$ and 0.78 mg/mL HLM (HL101) in 100 mM potassium phosphate buffer (pH 7.4) at 37° C. on the 96-deep well plate. The reaction mixture was split into two groups, a non-P450 and a P450 group. NADPH was only added to the reaction mixture of the P450 group. An aliquot of samples of P450 group was collected at 0, 10, 30, and 60 min time point, where 0 min time point indicated the time when NADPH was added into the reaction mixture of P450 group. An aliquot of samples of non-P450 group was collected at −10 and 65 min time point. Collected aliquots were extracted with acetonitrile solution containing an internal standard. The precipitated protein was spun down in centrifuge (2000 rpm, 15 min). The compound concentration in supernatant was measured by LC/MS/MS system.

The half-life value was obtained by plotting the natural logarithm of the peak area ratio of compounds/internal standard versus time. The slope of the line of best fit through the points yields the rate of metabolism (k). This was converted to a half-life value using following equations:

$$\text{Half-life}=\ln 2/k$$

EXAMPLES

The invention is illustrated in the following non-limiting examples in which, unless stated otherwise: all reagents are commercially available, all operations were carried out at room or ambient temperature, that is, in the range of about 18-25° C.; evaporation of solvent was carried out using a rotary evaporator under reduced pressure with a bath temperature of up to about 60° C.; reactions were monitored by thin layer chromatography (tlc) and reaction times are given for illustration only; melting points (m.p.) given are uncorrected (polymorphism may result in different melting points); the structure and purity of all isolated compounds were assured by at least one of the following techniques: tlc (Merck silica gel 60 $F_{254}$ precoated TLC plates or Merck NH$_2$ $F_{254s}$ precoated HPTLC plates), mass spectrometry, nuclear magnetic resonance (NMR), infrared red absorption spectra (IR), or microanalysis. Yields are given for illustrative purposes only. Flash column chromatography was carried out using Merck silica gel 60 (230-400 mesh ASTM) or Fuji Silysia Chromatorexo DU3050 (Amino Type, 30~50 µm). Low-resolution mass spectral data (EI) were obtained on a Integrity (Waters) mass spectrometer or a Automass 120 (JEOL) mass spectrometer. Low-resolution mass spectral data (ESI) were obtained on a ZMD2 (Waters) mass spectrometer or a Quattro II (Micromass) mass spectrometer. NMR data was determined at 270 MHz (JEOL JNM-LA 270 spectrometer) or 300 MHz (JEOL JNM-LA300) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br.=broad, etc. IR spectra were measured by a Shimazu infrared spectrometer (IR-470). Optical rotations were measured using a JASCO DIP-370 Digital Polarimeter (Japan Spectroscopic Co., Ltd.). Chemical symbols have their usual meanings; b.p. (boiling point), m.p. (melting point), L (liter(s)), mL (milliliter(s)), g (gram(s)), mg (milligram(s)), mol (moles), mmol (millimoles).

Example 1

4-{[4-({[4-(2,2,2-Trifluoroethoxy)-1,2-benzisoxazol-3-yl]oxy}methyl)piperidin-1-yl]methyl}tetrahydro-2H-pyran-4-carboxylic acid

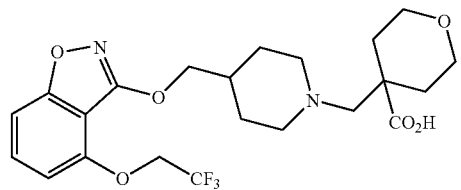 [SMILES: O=C(O)C1(CN2CCC(COc3noc4cccc(OCC(F)(F)F)c34)CC2)CCOCC1]

Step 1

Methyl 2-hydroxy-6-(2,2,2-trifluoroethoxy)benzoate

A mixture of 5-hydroxy-2,2-dimethyl-4H-1,3-benzodioxin-4-one (123 g, 633 mmol, Synth. Commun. 1994, 24, 1025), potassium carbonate (262 g, 1.9 mol) and 2,2,2-trifluoroethyl trifluoromethanesulfonate (95.8 mL, 665 mmol) in N,N-dimethylformamide (600 mL) was stirred at 50° C. for 30 min. Then methanol (300 mL) was added to the mixture, and stirring was continued for 5 h at that temperature. After cooling to room temperature, the mixture was diluted with water (500 mL) and neutralized with 2N hydrochloric acid. Product was extracted with a mixture of ethyl acetate-hexane (5:1, 500 mL×3). Combined organic layers were washed with water (500 mL), dried over magnesium sulfate and concentrated under reduced pressure. The residual solid was recrystallized from methanol-water to afford 125 g (79%) of the desired product as colorless crystals.

$^1$H-NMR (CDCl$_3$) δ: 11.47 (1H, s), 7.36 (1H, t, J=8.4 Hz), 6.72 (1H, dd, J=1.1, 8.4 Hz), 6.38 (1H, q, J=8.1 Hz), 4.36 (2H, q, J=8.0 Hz), 3.96 (3H, s).

MS (ESI) m/z: 251 (M+H)$^+$, 249 (M−H)$^-$.

Step 2

4-(2,2,2-Trifluoroethoxy)-1,2-benzisoxazol-3-ol

To a solution of hydroxylamine sulfate (120 g, 732 mmol) in water (360 mL) was added potassium carbonate (121 g, 875 mmol) at 0° C. After 30 min of stirring, sodium sulfite (3.74 g, 29.7 mmol) and a methanolic solution of methyl 2-hydroxyl-6-(2,2,2-trifluoroethoxy)benzoate (36.4 g, 146 mmol, EXAMPLE 1, step 1, in 360 mL of methanol) were added to the mixture. Then the mixture was warmed to 50° C. and stirred for 30 h. After cooling to room temperature, reaction mixture was partially concentrated to approx. ⅔ volume and acidified with 2N hydrochloric acid. Product was extracted three times with ethyl acetate. Combined organic layer was washed with brine, dried over sodium sulfate and concentrated under reduced pressure to afford the desired product as a crystalline solid. Crude product (36.3 g) was used for the next step without further purification.

The described above crude product (5.56 g, 22.14 mmol) was suspended in tetrahydrofuran (22.0 mL) and heated at 50° C. 1,1'-carbonyldiimidazole (7.54 g, 46.48 mmol) was added to the suspension at 50° C. After addition, the mixture was stirred at 50° C. for 14 h, the mixture was cooled to room temperature. 2N hydrochloric acid was added to the mixture and extracted with ethyl acetate. The organic layer was extracted with 10% aq. potassium carbonate (100 mL×5). The water layers were acidified with 2N hydrochloric acid and extracted with ethyl acetate (200 mL×2). The extracts were combined and dried over sodium sulfate and concentrated in vacuo to give brown solid. The residual solid was recrystallized from ethyl acetate/hexane to give 3.21 g (61%) of the title compound as colorless needles.

$^1$H-NMR (CDCl$_3$) δ: 7.53 (1H, t, J=8.5 Hz), 7.14 (1H, d, J=8.5 Hz), 6.73 (1H, d, J=7.9 Hz), 4.63 (2H, q, J=8.0 Hz), 3.83 (1H, br).

MS (ESI) m/z: 234 (M+H)$^+$, 232 (M−H)$^−$.

Step 3

[Methoxy(tetrahydro-4H-pyran-4-ylidene)methoxy](trimethyl)silane

To a stirred solution of diisopropylamine (5.2 mL, 37 mmol) in tetrahydrofuran (15 mL) was added dropwise n-butyllithium (1.6 M in hexane, 21 mL, 34 mmol) at 0° C. and stirred for 20 min. A mixture of methyl tetrahydro-2H-pyran-4-carboxylate (4.5 g, 31 mmol) and trimethylsilyl chloride (4.3 mL, 34 mmol) was added to the mixture at −40° C., then trimethylsilyl chloride (0.4 mL, 0.3 mmol) was added to the mixture. The mixture was stirred at room temperature for 2 h. The volatile components were removed by evaporation and the residual mixture was filtered through a pad of celite washing with hexane. The filtrate was evaporated to give 6.9 g (quant.) of the title compound as a clear yellow oil.

$^1$H-NMR (CDCl$_3$) δ: 3.64-3.59 (4H, m), 3.52 (3H, s), 2.24 (2H, t, J=5.6 Hz), 2.15 (2H, t, J=5.4 Hz), 0.22 (9H, s).

Step 4

Methyl 4-{[4-(hydroxymethyl)piperidin-1-yl]methyl}tetrahydro-2H-pyran-4-carboxylate To a stirred mixture of piperidin-4-ylmethanol (5.0 g, 43.4 mmol), t-butyldimethylsilylchloride (7.2 g, 47.8 mmol), and triethylamine (7.3 mL, 52.1 mmol) in dichloromethane (50 mL) was added 4-dimethylaminopyridine (530 mg, 4.3 mmol) at 0° C. After being stirred at 0° C. for 2 h, 50 mL of water was added to the mixture. The mixture was extracted with dichloromethane (50 mL×3) and the extracts were combined, dried over sodium sulfate, and concentrated in vacuo to give 10.2 g of a crude oil. The residual oil was dissolved with 86 mL of ethanol, and potassium carbonate (7.2 g, 52.1 mmol) and paraformaldehyde (1.56 g, 52.1 mmol) were added to the solution. After being stirred at room temperature for 2 days, the mixture was filtered and the filtrate was concentrated in vacuo to give a yellow oil. The residual oil was dissolved with 45 mL of acetonitrile and magnesium chloride (414 mg, 4.3 mmol) was added to the solution. [methoxy(tetrahydro-4H-pyran-4-ylidene)methoxy](trimethyl)silane (11.3 g, 52.1 mmol, EXAMPLE 1, step 3) was added to the mixture at 0° C. After being stirred at 0° C. for 20 h, 100 mL of 2N hydrochloric acid was added to the mixture. The mixture was stirred for 30 min and washed with diethyl ether (100 mL×2). The water layer was neutralized with aq. ammonia and extracted with ethyl acetate (100 mL×2). The extracts were combined and dried over sodium sulfate and concentrated in vacuo to give a yellow oil. The residual oil was purified by silica gel column chromatography (dichloromethane/methanol/aq. ammonia 400:10:1) to give 6.8 g (41%) of the title compound as a colorless waxy solid.

$^1$H-NMR (CDCl$_3$) δ: 3.75-3.90 (2H, m), 3.71 (3H, s), 3.40-3.55 (4H, m), 2.73 (2H, m), 2.49 (2H, m), 2.10-2.25 (2H, m), 1.95-2.10 (2H, m), 1.50-1.70 (4H, m), 1.30-1.50 (2H, m), 1.10-1.30 (2H, m).

MS (ESI) m/z: 272 (M+H)$^+$.

Step 5

Methyl 4-{[4-({[4-(2,2,2-trifluoroethoxy)-1,2-benzisoxazol-3-yl]oxy}methyl)piperidin-1-yl]methyl}-tetrahydro-2H-pyran-4-carboxylate A mixture of 4-(2,2,2-trifluoroethoxy)-1,2-benzisoxazol-3-ol (230 mg, 1 mmol, EXAMPLE 1, step 2), methyl 4-{[4-(hydroxymethyl)piperidin-1-yl]methyl}tetrahydro-2H-pyran-4-carboxylate (270 mg, 1 mmol, EXAMPLE 1, step 4), and cyanomethyltributylphosphorane (400 mg, 1.5 mmol) in toluene (1.0 mL) was stirred at 100° C. for 16 h. After cooling, the mixture was concentrated in vacuo to give a dark brown oil. The residual oil was purified by silica gel column chromatography (hexane/ethyl acetate 2:1) to give 250 mg (51%) of the title compound as a white solid.

$^1$H-NMR (CDCl$_3$) δ: 7.44 (1H, dd, J=7.9, 8.4 Hz), 7.12 (1H, d, J=8.4 Hz), 6.61 (1H, d, J=7.9 Hz), 4.49 (2H, q, J=8.1 Hz), 4.24 (2H, d, J=6.4 Hz), 3.88-3.78 (2H, m), 3.72 (3H, s), 3.54-3.41 (2H, m), 2.83-2.71 (2H, m), 2.52 (2H, s), 2.35-1.29 (11H, m).

MS (ESI) m/z: 487 (M+H)$^+$.

Step 6

4-{[4-({[4-(2,2,2-Trifluoroethoxy)-1,2-benzisoxazol-3-yl]oxy}methyl)piperidin-1-yl]methyl}tetrahydro-2H-pyran-4-carboxylic acid A mixture of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate (89 mg, 0.18 mmol, EXAMPLE 1, Step 5) in tetrahydrofuran (1 mL), methanol (1 mL) and 2 N aq. sodium hydroxide (1 mL) was stirred at 70° C. for 17 h. The mixture was neutralized with 2 N hydrochloric acid (1 mL) and formed precipitate was filtered.

The precipitate was triturated with diethylether to give 50 mg (58%) of the title compound as a white solid.

$^1$H-NMR (DMSO-d$_6$) δ: 7.59 (1H, dd, J=8.1, 8.4 Hz), 7.25 (1H, d, J=8.4 Hz), 6.94 (1H, d, J=8.1 Hz), 4.93 (2H, q, J=8.7 Hz), 4.19 (2H, d, J=5.9 Hz), 3.75-3.62 (2H, m), 3.48-3.30 (2H, m), 2.90-2.74 (2H, m), 2.50 (2H, s), 2.29-2.13 (2H, m), 1.94-1.23 (9H, m).

A signal due to CO$_2$H was not observed.

MS (ESI) m/z: 473 (M+H)$^+$, 471 (M−H)$^−$.

m.p.: 171.7° C.

IR (KBr) ν: 2950, 1617, 1527, 1188, 1113 cm$^{-1}$.

Anal. Calcd for C$_{22}$H$_{27}$N$_2$O$_6$F$_3$: C, 55.93; H, 5.76; N, 5.93. Found: C, 55.72; H, 5.78; N, 5.80.

Example 2

1-{[4-({[4-(2,2,2-Trifluoroethoxy)-1,2-benzisoxazol-3-yl]oxy}methyl)piperidin-1-yl]methyl}-cyclobutanecarboxylic acid

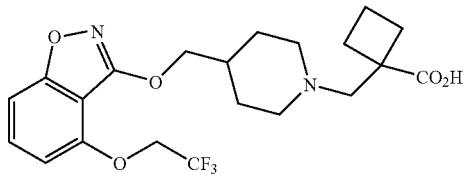 [SMILES: O=C(O)C1(CN2CCC(COc3noc4cccc(OCC(F)(F)F)c34)CC2)CCC1]

Step 1 tert-Butyl 4-({[4-(2,2,2-trifluoroethoxy)-1,2-benzisoxazol-3-yl]oxy}methyl)piperidine-1-carboxylate A mixture of 4-(2,2,2-trifluoroethoxy)-1,2-benzisoxazol-3-ol (0.12 g, 0.50 mmol, EXAMPLE 1, step 2), tert-butyl 4-(hydroxymethyl)piperidine-1-carboxylate (0.13 g, 0.60 mmol), and dimethyl (tributylphosphoranylidene)malonate (0.32 g, 1.0 mmol, J. Org. Chem. 2003, 68, 1597-1600) in toluene (0.5 mL) was stirred at 80° C. for 16 h. The mixture was purified by silica gel column chromatography (hexane/ethyl acetate 4:1) to give 0.14 g (65%) of the title compound as a white solid.

$^1$H-NMR (CDCl$_3$) δ: 7.45 (1H, dd, J=7.9, 8.6 Hz), 7.12 (1H, d, J=8.6 Hz), 6.60 (1H, d, J=7.9 Hz), 4.48 (2H, q, J=7.9 Hz), 4.33-4.06 (4H, m), 2.85-2.68 (2H, m), 2.18-1.97 (1H, m), 1.89-1.77 (2H, m), 1.47 (9H, s), 1.44-1.22 (2H, m).

MS (ESI) m/z: 331 (M−CO$_2$Bu$^t$+H)$^+$.

TLC Rf: 0.2 (ethyl acetate/hexane 4:1)

Step 2

3-(Piperidin-4-ylmethoxy)-4-(2,2,2-trifluoroethoxy)-1,2-benzisoxazole

To a stirred mixture of tert-butyl 4-({[4-(2,2,2-trifluoroethoxy)-1,2-benzisoxazol-3-yl]oxy}methyl)-piperidine-1-carboxylate (3.0 g, 6.96 mmol, EXAMPLE 2, Step 1) in 10% hydrogen chloride in methanol (100 mL) was added hydrochloric acid (3.0 mL) at ambient temperature. After being stirred at room temperature for 2 h, the mixture was concentrated in vacuo to give a solid. The residual solid was dissolved with water and dichloromethane. Sat. aq. ammonia was added to the mixture and extracted with dichloromethane (100 mL×3). The extracts were combined and dried over sodium sulfate and concentrated in vacuo to give 2.31 g (quant.) of the title compound as a white solid.

$^1$H-NMR (CDCl$_3$) δ: 7.44 (1H, t, J=8.5 Hz), 7.13 (1H, d, J=8.5 Hz), 6.61 (1H, d, J=7.9 Hz), 4.50 (2H, q, J=7.9 Hz), 4.26 (2H, d, J=6.6 Hz), 3.15 (2H, br), 2.67 (2H, m), 2.05 (1H, m) 1.73-1.93 (3H, m), 1.33 (2H, m).

MS (ESI) m/z: 331 (M+H)$^+$.

Step 3

Methyl 1-{[4-({[4-(2,2,2-trifluoroethoxy)-1,2-benzisoxazol-3-yl]oxy}methyl)piperidin-1-yl]methyl}-cyclobutanecarboxylate To a stirred mixture of 3-(piperidin-4-ylmethoxy)-4-(2,2,2-trifluoroethoxy)-1,2-benzisoxazole (0.33 g, 1.0 mmol, EXAMPLE 2, Step 2) and methyl 1-formylcyclobutanecarboxylate (0.17 g, 1.2 mmol, J. Org. Chem. 1993, 58, 6843-6850) in dichloromethane (5 mL) was added sodium triacetoxyborohydride (0.42 g, 2.0 mmol) at room temperature. After being stirred at room temperature for 16 h, sat. aq. sodium hydrogencarbonate (20 mL) was added to the mixture. The mixture was extracted with dichloromethane (30 mL×2). The combined extract was dried over magnesium sulfate and concentrated in vacuo to give 0.46 g (quant.) of the title compound as a colorless oil.

$^1$H-NMR (CDCl$_3$) δ: 7.43 (1H, dd, J=7.9, 8.4 Hz), 7.12 (1H, d, J=8.4 Hz), 6.61 (1H, d, J=7.9 Hz), 4.49 (2H, q, J=8.1 Hz), 4.23 (2H, d, J=6.6 Hz), 3.88-3.78 (2H, m), 3.71 (3H, s), 2.89-2.77 (2H, m), 2.72 (2H, s), 2.51-1.69 (9H, m), 1.45-1.25 (2H, m).

Step 4

1-{[4-({[4-(2,2,2-Trifluoroethoxy)-1,2-benzisoxazol-3-yl]oxy}methyl)piperidin-1-yl]methyl}-cyclobutanecarboxylic acid The title compound was prepared according to the procedure described in Step 6 of EXAMPLE 1 using methyl 1-{[4-({[4-(2,2,2-trifluoroethoxy)-1,2-benzisoxazol-3-yl]oxy}methyl)piperidin-1-yl]methyl}-cyclobutanecarboxylate (0.46 g, 1.0 mmol, EXAMPLE 2, Step 3) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

$^1$H-NMR (DMSO-d$_6$) δ: 7.59 (1H, dd, J=8.1, 8.4 Hz), 7.25 (1H, d, J=8.4 Hz), 6.94 (1H, d, J=8.1 Hz), 4.93 (2H, q, J=8.7 Hz), 4.20 (2H, d, J=6.3 Hz), 2.96-2.82 (2H, m), 2.73 (2H, s), 2.37-2.11 (4H, m), 2.02-1.70 (7H, m), 1.42-1.20 (2H, m).

A signal due to CO$_2$H was not observed.

MS (ESI) m/z: 443 (M+H)$^+$, 441 (M−H)$^−$.

m.p.: 164.9° C.

IR (KBr) ν: 3404, 2951, 1617, 1534, 1161, 1117 cm$^−$.

Anal. Calcd for C$_{21}$H$_{25}$N$_2$O$_5$F$_3$.H$_2$O: C, 54.78; H, 5.91; N, 6.08. Found: C, 54.61; H, 5.90; N, 6.14.

Example 3

2,2-Dimethyl-3-[4-({[4-(2,2,2-trifluoroethoxy)-1,2-benzisoxazol-3-yl]oxy}methyl)-piperidin-1-yl]propanoic acid

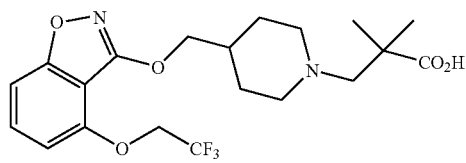 [SMILES: CC(C)(CN1CCC(COc2noc3cccc(OCC(F)(F)F)c23)CC1)C(=O)O]

Step 1

Methyl 2,2-dimethyl-3-[4-({[4-(2,2,2-trifluoroethoxy)-1,2-benzisoxazol-3-yl]oxy}methyl)-Piperidin-1-yl]propanoate The title compound was prepared according to the procedure described of Step 3 in the EXAMPLE 2 using methyl 2,2-dimethyl-3-oxopropanoate (0.16 g, 1.2 mmol, Tetrahedron Asymmetry 2003, 14, 3371-3378) instead of methyl 1-formylcyclobutanecarboxylate.

$^1$H-NMR (CDCl$_3$) δ: 7.43 (1H, dd, J=7.9, 8.4 Hz), 7.12 (1H, d, J=8.4 Hz), 6.61 (1H, d, J=7.9 Hz), 4.49 (2H, q, J=7.9 Hz), 4.24 (2H, d, J=6.4 Hz), 3.66 (3H, s), 2.88-2.77 (2H, m), 2.49 (2H, s), 2.30-1.67 (5H, m), 1.51-1.31 (2H, m), 1.17 (6H, s).

Step 2

2,2-Dimethyl-3-[4-({[4-(2,2,2-trifluoroethoxy)-1,2-benzisoxazol-3-yl]oxy}methyl)-piperidin-1-yl]propanoic acid The title compound was prepared according to the procedure described of Step 6 in the EXAMPLE 1 using methyl 2,2-dimethyl-3-[4-({[4-(2,2,2-trifluoroethoxy)-1,2-benzisoxazol-3-yl]oxy}methyl)-piperidin-1-yl]propanoate (0.40 g, 1.0 mmol, EXAMPLE 3, Step 1) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

$^1$H-NMR (DMSO-d$_6$) δ: 7.59 (1H, dd, J=8.1, 8.4 Hz), 7.25 (1H, d, J=8.4 Hz), 6.94 (1H, d, J=8.1 Hz), 4.93 (2H, q, J=8.7 Hz), 4.20 (2H, d, J=5.9 Hz), 2.94-2.81 (2H, m), 2.46 (2H, s), 2.32-2.15 (2H, m), 1.89-1.64 (3H, m), 1.49-1.26 (2H, m), 1.07 (6H, s).

A signal due to CO$_2$H was not observed.
MS (ESI) m/z: 431 (M+H)$^+$, 429 (M−H)$^−$.
m.p.: 129.2° C.
IR (KBr) ν: 3395, 2961, 1617, 1534, 1160, 1116 cm$^{-1}$.
Anal. Calcd for C$_{20}$H$_{25}$N$_2$O$_5$F$_3$·H$_2$O: C, 53.57; H, 6.07; N, 6.25. Found: C, 53.66; H, 6.07; N, 6.33.

Example 4 trans-4-{[4-({[4-(2,2,2-Trifluoroethoxy)-1,2-benzisoxazol-3-yl]oxy}methyl)-piperidin-1-yl]methyl}cyclohexanecarboxylic acid

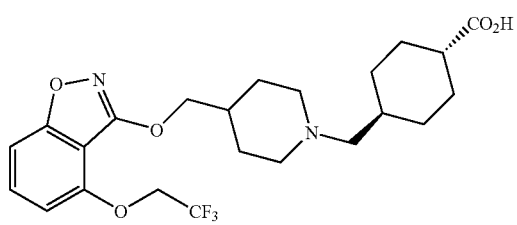 [SMILES: O=C(O)[C@H]1CC[C@H](CN2CCC(COc3noc4cccc(OCC(F)(F)F)c34)CC2)CC1]

Step 1

Methyl trans-4-{[4-({[4-(2,2,2-trifluoroethoxy)-1,2-benzisoxazol-3-yl]oxy}methyl)-piperidin-1-yl]methyl}cyclohexanecarboxylate The title compound was prepared according to the procedure described of Step 3 in the EXAMPLE 2 using methyl trans-4-formylcyclohexanecarboxylate (0.24 g, 1.4 mmol, JP 490-48639) instead of methyl 1-formylcyclobutanecarboxylate.

$^1$H-NMR (CDCl$_3$) δ: 7.44 (1H, dd, J=7.9, 8.4 Hz), 7.12 (1H, d, J=8.4 Hz), 6.61 (1H, d, J=7.9 Hz), 4.49 (2H, q, J=8.1 Hz), 4.26 (2H, d, J=6.6 Hz), 3.66 (3H, s), 3.02-2.84 (2H, m), 2.36-1.33 (17H, m), 1.11-1.82 (2H, m).

Step 2 trans-4-{[4-({[4-(2,2,2-Trifluoroethoxy)-1,2-benzisoxazol-3-yl]oxy}methyl)-piperidin-1-yl]methyl}cyclohexanecarboxylic acid The title compound was prepared according to the procedure described of Step 6 in the EXAMPLE 1 using methyl trans-4-{[4-({[4-(2,2,2-trifluoroethoxy)-1,2-benzisoxazol-3-yl]oxy}methyl)-piperidin-1-yl]methyl}cyclohexanecarboxylate (1.0 mmol, EXAMPLE 4, Step 1) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

$^1$H-NMR (DMSO-d$_6$) δ: 7.59 (1H, dd, J=8.1, 8.4 Hz), 7.25 (1H, d, J=8.4 Hz), 6.94 (1H, d, J=8.1 Hz), 4.93 (2H, q, J=8.7 Hz), 4.20 (2H, d, J=5.8 Hz), 2.91-2.75 (2H, m), 2.17-1.99 (3H, m), 1.95-1.65 (9H, m), 1.56-1.16 (5H, m), 0.95-0.72 (2H, m).

A signal due to CO$_2$H was not observed.
MS (ESI) m/z: 471 (M+H)$^+$, 469 (M−H)$^−$.
m.p.: 158.0° C.
IR (KBr) ν: 3422, 2934, 1617, 1534, 1161, 1114 cm$^{-1}$.
Anal. Calcd for C$_{23}$H$_{29}$N$_2$O$_5$F$_3$: C, 58.27; H, 6.25; N, 5.91. Found: C, 58.00; H, 6.21; N, 5.84.

Example 5

4-{2-[4-({[4-(2,2,2-Trifluoroethoxy)-1,2-benzisoxazol-3-yl]oxy}methyl)piperidin-1-yl]ethyl}tetrahydro-2H-pyran-4-carboxylic acid

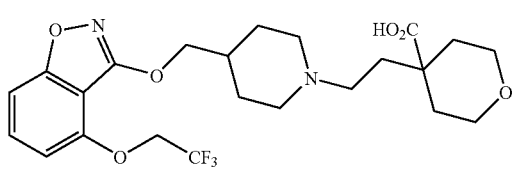 [SMILES: O=C(O)C1(CCN2CCC(COc3noc4cccc(OCC(F)(F)F)c34)CC2)CCOCC1]

Step 1

Methyl 4-{2-[4-({[4-(2,2,2-trifluoroethoxy)-1,2-benzisoxazol-3-yl]oxy}methyl)piperidin-1-yl]ethyl}tetrahydro-2H-pyran-4-carboxylate The title compound was prepared according to the procedure described of Step 3 in the EXAMPLE 2 using methyl 4-(2-oxoethyl)tetrahydro-2H-pyran-4-carboxylate (0.29 g, 1.6 mmol, WO 2004/043958) instead of methyl 1-formylcyclobutanecarboxylate.

$^1$H-NMR (CDCl$_3$) δ: 7.43 (1H, dd, J=7.9, 8.4 Hz), 7.12 (1H, d, J=8.4 Hz), 6.61 (1H, d, J=7.9 Hz), 4.49 (2H, q, J=8.1 Hz), 4.25 (2H, d, J=7.8 Hz), 3.92-3.70 (5H, m), 3.55-3.38 (2H, m), 3.05-2.89 (2H, m), 2.38-1.34 (15H, m).

Step 2

4-{2-[4-({[4-(2,2,2-Trifluoroethoxy)-1,2-benzisoxazol-3-yl]oxy}methyl)piperidin-1-yl]ethyl}-tetrahydro-2H-pyran-4-carboxylic acid The title compound was prepared according to the procedure described of Step 6 in the EXAMPLE 1 using methyl 4-{2-[4-({[4-(2,2,2-trifluoroethoxy)-1,2-benzisoxazol-3-yl]oxy}methyl)piperidin-1-yl]ethyl}tetrahydro-2H-pyran-4-carboxylate (1.0 mmol, EXAMPLE 5, Step 1) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

¹H-NMR (DMSO-$d_6$) δ: 7.59 (1H, dd, J=8.1, 8.4 Hz), 7.25 (1H, d, J=8.4 Hz), 6.94 (1H, d, J=8.1 Hz), 4.93 (2H, q, J=8.7 Hz), 4.20 (2H, d, J=6.3 Hz), 3.78-3.60 (2H, m), 3.45-3.30 (2H, m), 3.00-2.86 (2H, m), 2.38-2.23 (2H, m), 2.08-1.60 (9H, m), 1.52-1.21 (4H, m).

A signal due to CO$_2$H was not observed.

MS (ESI) m/z: 487 (M+H)⁺, 485 (M−H)⁻.

m.p.: 220.5° C.

IR (KBr) ν: 3414, 2934, 1617, 1560, 1160, 1118 cm⁻¹.

Anal. Calcd for $C_{23}H_{29}N_2O_6F_3$: C, 56.78; H, 6.01; N, 5.76. Found: C, 56.64; H, 6.02; N, 5.69.

Example 6

2,2-Difluoro-3-[4-({[4-(2,2,2-trifluoroethoxy)-1,2-benzisoxazol-3-yl]oxy}methyl)-piperidin-1-yl]propanoic acid

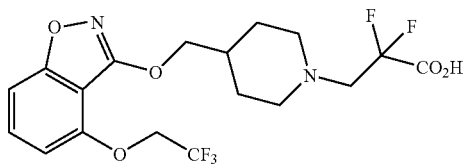 [SMILES: O=C(O)C(F)(F)CN1CCC(COc2noc3cccc(OCC(F)(F)F)c23)CC1]

Step 1

Ethyl 2,2-difluoro-3-[4-({[4-(2,2,2-trifluoroethoxy)-1,2-benzisoxazol-3-yl]oxy}methyl)piperidin-1-yl]propanoate A mixture of 3-(piperidin-4-ylmethoxy)-4-(2,2,2-trifluoroethoxy)-1,2-benzisoxazole (0.51 g, 1.5 mmol, EXAMPLE 2, Step 2) and 1H-benztriazole-1-methanol (0.22 g, 1.5 mmol) in ethanol (6 mL) was stirred at 50° C. for 20 min. The mixture was concentrated in vacuo to give a solid. The residual solid was dissolved with tetrahydrofuran (2 mL) and this solution was added to a mixture of zinc powder (0.20 g, 3.0 mmol), trimethylsilylchloride (0.19 mL, 1.5 mmol), and ethyl bromodifluoroacetate (0.46 g, 2.3 mmol) in tetrahydrofuran (6 mL) at room temperature. The mixture was refluxed for 2 h and then cooled to room temperature. The mixture was filtered and the filtrate was diluted with ethyl acetate and sat. aq. sodium hydrogencarbonate (30 mL). The mixture was extracted with ethyl acetate (50 mL×2) and washed with brine. The combined extract was dried over magnesium sulfate and concentrated in vacuo to give an oil. The residual oil was purified by silica gel column chromatography (hexane/ethyl acetate 4:1) to give 0.34 g (49%) of the title compound as a colorless oil.

¹H-NMR (CDCl$_3$) δ: 7.44 (1H, dd, J=7.9, 8.4 Hz), 7.12 (1H, d, J=8.4 Hz), 6.61 (1H, d, J=7.9 Hz), 4.48 (2H, q, J=7.9 Hz), 4.35 (2H, q, J=7.1 Hz), 4.23 (2H, d, J=6.6 Hz), 3.08-2.92 (4H, m), 2.39-2.24 (2H, m), 2.00-1.74 (3H, m), 1.46-1.22 (5H, m).

MS (ESI) m/z: 467 (M+H)⁺.

Step 2

2,2-Difluoro-3-[4-({[4-(2,2,2-trifluoroethoxy)-1,2-benzisoxazol-3-yl]oxy}methyl)piperidin-1-yl]propanoic acid The title compound was prepared according to the procedure described of Step 6 in the EXAMPLE 1 using ethyl 2,2-difluoro-3-[4-({[4-(2,2,2-trifluoroethoxy)-1,2-benzisoxazol-3-yl]oxy}methyl)-piperidin-1-yl]propanoate (0.43 g, 0.92 mmol, EXAMPLE 6, Step 1) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

¹H-NMR (DMSO-$d_6$) δ: 7.60 (1H, dd, J=8.1, 8.4 Hz), 7.26 (1H, d, J=8.4 Hz), 6.95 (1H, d, J=8.1 Hz), 4.95 (2H, q, J=8.7 Hz), 4.24 (2H, d, J=6.6 Hz), 3.46-3.19 (4H, m), 2.83-2.67 (2H, m), 2.09-1.79 (3H, m), 1.58-1.35 (2H, m).

A signal due to CO$_2$H was not observed.

MS (ESI) m/z: 439 (M+H)⁺, 437 (M−H)⁻.

m.p.: 227.1° C.

IR (KBr) ν: 3414, 2969, 1669, 1540, 1189, 1154 cm⁻¹.

Anal. Calcd for $C_{18}H_{19}N_2O_5F_5$: C, 49.32; H, 4.37; N, 6.39. Found: C, 48.93; H, 4.32; N, 6.23.

Example 7

4-{[4-(2-{[4-(2,2,2-Trifluoroethoxy)-1,2-benzisoxazol-3-yl]oxy}ethyl)piperidin-1-yl]methyl}tetrahydro-2H-pyran-4-carboxylic acid

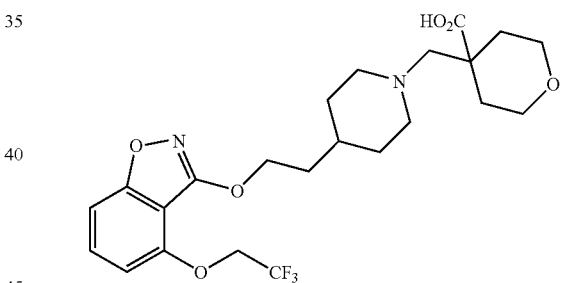

Step 1

4-(Benzyloxy)-1,2-benzisoxazol-3-ol

The title compound was prepared according to the procedure described in Step 2 of EXAMPLE 1 using methyl 2-(benzyloxy)-6-hydroxybenzoate instead of methyl 2-hydroxyl-6-(2,2,2-trifluoroethoxy)-benzoate.

¹H-NMR (DMSO $d_6$) δ: 12.19 (1H, br), 7.3-7.6 (6H, m), 7.10 (1H, d, J=8.4 Hz), 6.90 (1H, t, J=8.4 Hz), 5.28 (2H, s).

MS (ESI) m/z: 240 (M−H)⁺.

Step 2 tert-Butyl 4-(2-{[4-(benzyloxy)-1,2-benzisoxazol-3-yl]oxy}ethyl)piperidine-1-carboxylate Diisopropyl azodicarboxylate (3.2 mL, 17 mmol) was added to a mixture of 4-(benzyloxy)-1,2-benzisoxazol-3-ol (2.7 g, 11 mmol, EXAMPLE 7, Step 1), tert-butyl 4-(2-hydroxyethyl)piperidine-1-carboxylate (3.1 g, 14 mmol), and triphenylphosphine (4.3 g, 17 mmol) in toluene (11 mL) at 0° C. The mixture was stirred at room temperature for 16 h, and concentrated in vacuo to give a yellow oil. The residual oil was purified by silica gel column chromatography (hexane/ethyl acetate 4:1) to give 3.8 g (76%) of the title compound as a colorless oil.

$^1$H-NMR (CDCl$_3$) δ: 7.55-7.30 (6H, m), 7.02 (1H, d, J=8.6 Hz), 6.68 (1H, d, J=7.9 Hz), 5.21 (2H, s), 4.47 (2H, t, J=5.9 Hz), 4.20-3.95 (2H, m), 2.72-2.54 (2H, m), 1.88-1.61 (5H, m), 1.46 (9H, s), 1.34-1.05 (2H, m).

Step 3

4-(Benzyloxy)-3-(2-piperidin-4-ylethoxy)-1,2-benzisoxazole

The title compound was prepared according to the procedure described in Step 2 of EXAMPLE 2 using tert-Butyl 4-(2-{[4-(benzyloxy)-1,2-benzisoxazol-3-yl]oxy}ethyl)piperidine-1-carboxylate instead of tert-butyl 4-({[4-(2,2,2-trifluoroethoxy)-1,2-benzisoxazol-3-yl]oxy}methyl)piperidine-1-carboxylate.

$^1$H-NMR (CDCl$_3$) δ: 7.55-7.30 (6H, m), 7.02 (1H, d, J=8.6 Hz), 6.68 (1H, d, J=7.9 Hz), 5.20 (2H, s), 4.47 (2H, t, J=5.9 Hz), 3.20-3.08 (2H, m), 2.67-2.52 (2H, m), 1.90-1.61 (5H, m), 1.43-1.22 (2H, m).

A signal due to N$\underline{H}$ was not observed.
MS (ESI) m/z: 353 (M+H)$^+$.

Step 4

4-(Benzyloxy)-3-{2-[1-(ethoxymethyl)piperidin-4-yl]ethoxy}-1,2-benzisoxazole

To a stirred mixture of 4-(benzyloxy)-3-(2-piperidin-4-ylethoxy)-1,2-benzisoxazole (3.1 g, 8.4 mmol, EXAMPLE 7, Step 3) and potassium carbonate (1.2 g, 8.4 mmol) in ethanol (16.0 mL) was added paraformaldehyde (0.28 g, 9.2 mmol) at ambient temperature. After being stirred at room temperature for 14 h, the mixture was filtered. The filtrate was concentrated in vacuo to give 3.4 g (quant.) of the title compound as a colorless oil.

$^1$H-NMR (CDCl$_3$) δ: 7.54-7.30 (6H, m), 7.02 (1H, d, J=8.8 Hz), 6.67 (1H, d, J=8.1 Hz), 5.22 (2H, s), 4.47 (2H, t, J=5.9 Hz), 4.07 (2H, s), 3.50 (2H, q, J=7.3 Hz), 2.95-2.83 (2H, m), 2.50-2.35 (2H, m), 1.96-1.48 (5H, m), 1.38-1.10 (5H, m).

Step 5

Methyl 4-{[4-(2-{[4-(benzyloxy)-1,2-benzisoxazol-3-yl]oxy}ethyl)piperidin-1-yl]methyl}tetrahydro-2H-pyran-4-carboxylate

[Methoxy(tetrahydro-4H-pyran-4-ylidene)methoxy](trimethyl)silane (2.2 g, 10.0 mmol, EXAMPLE 1, step 3) was added to the mixture of 4-(benzyloxy)-3-{2-[1-(ethoxymethyl)piperidin-4-yl]ethoxy}-1,2-benzisoxazole (3.4 g, 8.4 mmol, EXAMPLE 7, step 4) and magnesium chloride (40 mg, 0.42 mmol) in acetonitrile (16.0 mL) at ambient temperature. After being stirred at room temperature for 3 h, the mixture was concentrated in vacuo to give an oil. The residual oil was purified by silica gel column chromatography (ethyl acetate/hexane 2:3) to give 3.2 g (75%) of the title compound as a colorless oil.

$^1$H-NMR (CDCl$_3$) δ: 7.53-7.28 (6H, m), 7.02 (1H, d, J=8.6 Hz), 6.67 (1H, d, J=7.9 Hz), 5.22 (2H, s), 4.45 (2H, t, J=6.6 Hz), 3.87-3.76 (2H, m), 3.70 (3H, s), 3.54-3.39 (2H, m), 2.73-2.63 (2H, m), 2.46 (2H, s), 2.20-1.97 (4H, m), 1.86-1.17 (9H, m).
MS (ESI) m/z: 509 (M+H)$^+$.

Step 6

Methyl 4-[(4-{2-[(4-hydroxy-1,2-benzisoxazol-3-yl)oxy]ethyl}piperidin-1-yl)methyl]tetrahydro-2H-pyran-4-carboxylate A mixture of methyl 4-{[4-(2-{[4-(benzyloxy)-1,2-benzisoxazol-3-yl]oxy}ethyl)piperidin-1-yl]methyl}tetrahydro-2H-pyran-4-carboxylate (3.2 g, 6.3 mmol, EXAMPLE 7, step 5) and 10% Pd—C (0.30 g) in tetrahydrofuran (20 mL) and methanol (40 mL) was stirred at room temperature for 10 min under hydrogen atmosphere. The mixture was filtered through a pad of celite and the filtrate was concentrated in vacuo to give an oil. The residual oil was purified by silica gel column chromatography (hexane/ethyl acetate 3:1 to 3:2) to give 2.2 g (83%) of the title compound as a pale yellow solid.

$^1$H-NMR (CDCl$_3$) δ: 7.39 (1H, t, J=7.9 Hz), 6.96 (1H, d, J=7.9 Hz), 6.65 (1H, d, J=7.9 Hz), 4.50 (2H, t, J=6.9 Hz), 3.89-3.76 (2H, m), 3.72 (3H, s), 3.55-3.40 (2H, m), 2.78-2.65 (2H, m), 2.48 (2H, s), 2.27-1.97 (4H, m), 1.89-1.17 (9H, m).

A signal due to O$\underline{H}$ was not observed.
MS (ESI) m/z: 419 (M+H)$^+$, 417 (M−H)$^-$.

Step 7

Methyl 4-{[4-(2-{[4-(2,2,2-trifluoroethoxy)-1,2-benzisoxazol-3-yl]oxy}ethyl)piperidin-1-yl]methyl}-tetrahydro-2H-pyran-4-carboxylate To a stirred mixture of methyl 4-[(4-{2-[(4-hydroxy-1,2-benzisoxazol-3-yl)oxy]ethyl}piperidin-1-yl)-methyl]tetrahydro-2H-pyran-4-carboxylate (0.63 g, 1.5 mmol, EXAMPLE 7, step 6) and potassium carbonate in N,N-dimethylformamide (3.0 mL) was added 2,2,2-trifluoroethyl trifluoromethanesulfonate (0.26 mL, 1.8 mmol) at 70° C. After being stirred at 70° C. for 3 h, the mixture was cooled to room temperature. The mixture was extracted with ethyl acetate (50 mL×2) and washed with water and brine. The extracts were combined and dried over magnesium sulfate and concentrated in vacuo to give a yellow oil. The residual oil was purified by silica gel column chromatography (hexane/ethyl acetate 2:1) to give 0.69 g (92%) of the title compound as a colorless viscous oil.

$^1$H-NMR (CDCl$_3$) δ: 7.44 (1H, dd, J=7.9, 8.6 Hz), 7.12 (1H, d, J=8.6 Hz), 6.61 (1H, d, J=7.9 Hz), 4.57-4.40 (4H, m), 3.89-3.77 (2H, m), 3.71 (3H, s), 3.54-3.39 (2H, m), 2.77-2.65 (2H, m), 2.48 (2H, s), 2.26-1.99 (4H, m), 1.84-1.18 (9H, m).
MS (ESI) m/z: 501 (M+H)$^+$.

Step 8

4-{[4-(2-{[4-(2,2,2-Trifluoroethoxy)-1,2-benzisoxazol-3-yl]oxy}ethyl)piperidin-1-yl]methyl}-tetrahydro-2H-pyran-4-carboxylic acid The title compound was prepared according to the procedure described in Step 6 of EXAMPLE 1 using methyl 4-{[4-(2-{[4-(2,2,2-trifluoroethoxy)-1,2-benzisoxazol-3-yl]oxy}ethyl)piperidin-1-yl]methyl}-tetrahydro-2H-pyran-4-carboxylate (0.69 g, 1.4 mmol, EXAMPLE 7, Step 7) instead of methyl 4-{[4-({[4-(2,2,2-trifluoroethoxy)-1,2-benzisox-azol-3-yl]oxy}methyl)piperidin-1-yl]methyl}tetrahydro-2H-pyran-4-carboxylate.

$^1$H-NMR (DMSO-$d_6$) δ: 7.59 (1H, dd, J=7.9, 8.6 Hz), 7.25 (1H, d, J=8.6 Hz), 6.94 (1H, d, J=8.1 Hz), 4.93 (2H, q, J=8.6 Hz), 4.38 (2H, t, J=6.6 Hz), 3.75-3.61 (2H, m), 3.47-3.32 (2H, m), 2.86-2.73 (2H, m), 2.47 (2H, s), 2.23-2.07 (2H, m), 1.90-1.11 (11H, m).

A signal due to CO$_2$H was not observed.
MS (ESI) m/z: 487 (M+H)$^+$, 485 (M−H)$^-$.
m.p.: 176.6° C.
IR (KBr) ν: 2954, 1617, 1536, 1262 1108 cm$^{-1}$.
Anal. Calcd for $C_{23}H_{29}N_2O_6F_3$: C, 56.78; H, 6.01; N, 5.76. Found: C, 56.69; H, 6.07; N, 5.83.

Example 8

1-[(4-Hydroxytetrahydro-2H-pyran-4-yl)methyl]-4-{[(4-isobutoxy-1,2-benzisoxazol-3-yl)oxy]methyl}-piperidinium and its p-toluenesulfonate salt

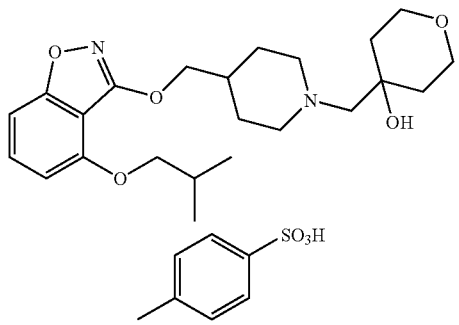

Step 1

Methyl 2-hydroxy-6-isobutoxybenzoate

A mixture of 5-hydroxy-2,2-dimethyl-4H-1,3-benzo-dioxin-4-one (880 mg, 4.53 mmol), potassium carbonate (1.89 g, 13.7 mmol) and isobutyl iodide (0.52 mL, 4.6 mmol) in N,N-dimethylformamide (5 mL) in a sealed tube was stirred at 80° C. After being stirred for 8 h, additional reagents (potassium carbonate: 2.0 g, 14 mmol; isobutyl bromide: 1.0 mL, 9.2 mmol) were added to the mixture, and the mixture was stirred at 130° C. for 10 h. After cooling to 80° C., methanol (3 mL) was added to the mixture, and the mixture was stirred further 15 h. Then the mixture was cooled to room temperature, diluted with ethyl acetate and washed with brine. The organic layer was dried over magnesium sulfate and concentrated in vacuo to give 836 mg (82%) of the title compound as a solid.

$^1$H-NMR (CDCl$_3$) δ: 11.50 (1H, s), 7.30 (1H, t, J=8.3 Hz), 6.57 (1H, dd, J=8.3, 0.9 Hz), 6.38 (1H, d, J=8.3 Hz), 3.94 (3H, s), 3.76 (2H, d, J=6.3 Hz), 2.12 (1H, nonatet, J=6.6 Hz), 1.06 (6H, d, J=6.8 Hz). TLC (silica gel, ethyl acetate/hexane 1:4) Rf: 0.67.

Step 2

4-Isobutoxy-1,2-benzisoxazol-3-ol

To a solution of methyl 2-hydroxy-6-isobutoxybenzoate (836 mg, 3.73 mmol, EXAMPLE 8, step 1) and hydroxy-lamine hydrochloride (412 mg, 5.93 mmol) in methanol (10 mL) was added potassium hydroxide (1.03 g, 18.4 mmol) at room temperature. After overnight stirring, additional reagents (hydroxylamine hydrochloride: 506 mg, 7.28 mmol; potassium hydroxide: 442 mg, 7.88 mmol) were added to the mixture, and stirring was continued for 2 days. Solvent was evaporated, and residual solid was acidified with 2N hydrochloric acid. The mixture was extracted three times with ethyl acetate. Combined organic layers were washed with brine, dried over magnesium sulfate and concentrated in vacuo to give 850 mg of crude product, which was used for the next step without further purification.

To a solution of the foregoing crude product (850 mg, 3.77 mmol) in tetrahydrofuran (10 mL) was added 1,1'-carbonyl-diimidazole (1.32 g, 8.14 mmol) as a suspension in tetrahydrofuran (4 mL) at 70° C. After being stirred for 5 h, reaction mixture was cooled to room temperature. Solvent was evaporated, and the residual solid was dissolved in ethyl acetate. Product was extracted five times with an aqueous solution of 5% potassium carbonate and 5% sodium hydrogencarbonate. Combined aqueous solution was acidified with 2N hydrochloric acid, and the mixture was extracted twice with ethyl acetate. Combined organic layers were washed with brine, dried over magnesium sulfate and concentrated in vacuo to give the title compound (327 mg, 42%) as a pale yellow solid.

$^1$H-NMR (CDCl$_3$) δ: 7.45 (1H, t, J=8.2 Hz), 6.96 (1H, d, J=8.4 Hz), 6.61 (1H, d, J=7.9 Hz), 3.91 (2H, d, J=6.6 Hz), 2.23 (1H, nonatet, J=6.6 Hz), 1.09 (6H, d, J=6.6 Hz).

A signal due to OH was not observed.
TLC (silica gel, ethyl acetate/hexane 1:2) Rf: 0.36.

Step 3 tert-Butyl 4-{[(4-isobutoxy-1,2-benzisoxazol-3-yl)oxy]methyl}piperidine-1-carboxylate The title compound was prepared according to the procedure described in Step 2 of EXAMPLE 7 using 4-isobutoxy-1,2-benzisoxazol-3-ol (EXAMPLE 8, Step 2) and tert-butyl 4-(hydroxymethyl)piperidine-1-carboxylate instead of 4-(benzyloxy)-1,2-benzisoxazol-3-ol and tert-butyl 4-(2-hydroxyethyl)piperidine-1-carboxylate.

$^1$H-NMR (CDCl$_3$) δ: 7.39 (1H, t, J=8.2 Hz), 6.97 (1H, d, J=8.4 Hz), 6.56 (1H, d, J=7.9 Hz), 4.28 (2H, d, J=6.3 Hz), 4.17 (2H, brd, J=12.2 Hz), 3.85 (2H, d, J=6.3 Hz), 2.76 (2H, brt, J=12.4 Hz), 2.20-1.95 (2H, m), 1.85 (2H, brd, J=12.2 Hz), 1.47 (9H, s), 1.40 (2H, m), 1.07 (6H, d, J=6.8 Hz). TLC (silica gel, ethyl acetate/hexane 1:2) Rf: 0.71.

Step 4

4-{[(Isobutoxy-1,2-benzisoxazol-3-yl)oxy]methyl}Piperidinium chloride

To a flask containing tert-butyl 4-{[(4-isobutyoxy-1,2-benzisoxazol-3-yl)oxy]methyl}piperidine-1-carboxylate (98.2 mg, 0.24 mmol, EXAMPLE 1, step 3) was added 4N solution of hydrogen chloride in ethyl acetate (1 mL) at room temperature. After being stirred for 2 h, solvent was evaporated and the residual solid was washed with ethyl acetate to give the title compound (62.4 mg, 75%) as a white solid.

$^1$H-NMR (CDCl$_3$) δ: 7.40 (1H, t, J=8.2 Hz), 6.97 (1H, d, J=8.4 Hz), 6.56 (1H, d, J=7.9 Hz), 4.32 (2H, d, J=7.1 Hz), 3.85 (2H, d, J=6.4 Hz), 3.57 (2H, brd, J=12.7 Hz), 2.94 (2H, dt, J=12.5 Hz, 2.5 Hz), 2.35-2.05 (4H, m), 1.82 (2H, m), 1.06 (6H, d, J=6.8 Hz).

Signals due to NH and HCl were not observed.

MS (ESI) m/z: 305 (M−Cl)⁺.

IR (KBr) v: 2963, 1612, 1533, 1433, 1369, 1286, 1096, 1082, 995 cm⁻¹.

Anal. Calcd for C₁₇H₂₄N₂O₃·HCl·0.2H₂O: C, 59.28; H, 7.43; N, 8.13. Found: C, 59.14; H, 7.24; N, 7.98.

Step 5

4-[(4-{[(4-Isobutoxy-1,2-benzisoxazol-3-yl)oxy]methyl}piperidin-1-yl)methyl]-tetrahydro-2H-pyran-4-ol A solution of 4-{[(isobutoxy-1,2-benzisoxazol-3-yl)oxy]methyl}piperidinium chloride (40.9 mg, 0.120 mmol, EXAMPLE 8, step 4), 1,6-dioxaspiro[2.5]octane (30.4 mg, 0.266 mmol, *Phosphorus and Sulfur and Related Elements* 1984, 19, 113) and N,N-diisopropylethylamine (0.10 mL, 0.58 mmol) in ethanol (1 mL) was stirred overnight at room temperature. Solvent was evaporated, and the residual oil was purified by NH gel column chromatography (hexane/ethyl acetate 4:1) to give 34.0 mg (68%) of the title compound as a colorless oil.

¹H-NMR (CDCl₃) δ: 7.39 (1H, t, J=8.2 Hz), 6.97 (1H, d, J=8.2 Hz), 6.56 (1H, d, J=8.1 Hz), 4.27 (2H, d, J=5.9 Hz), 3.86 (2H, d, J=6.3 Hz), 3.82-3.72 (4H, m), 2.93 (2H, brd, J=11.4 Hz), 2.42 (2H, td, J=11.5 Hz, 1.5 Hz), 2.34 (2H, s), 2.15 (1H, nonatet, J=6.6 Hz), 2.00-1.75 (3H, m), 1.65-1.40 (6H, m), 1.09 (6H, d, J=6.6 Hz).

Step 6

1-[(4-Hydroxytetrahydro-2H-pyran-4-yl)methyl]-4-{[(4-isobutoxy-1,2-benzisoxazol-3-yl)oxy]methyl}piperidinium p-toluenesulfonate 4-[(4-{[(4-Isobutoxy-1,2-benzisoxazol-3-yl)oxy]methyl}piperidin-1-yl)methyl]tetrahydro-2H-pyran-4-ol (34.0 mg, 0.0812 mmol, EXAMPLE 8, step 5) was dissolved in ethyl acetate (approximately 0.3 mL). To this solution was added a solution of p-toluenesulfonic acid monohydrate (21.7 mg, 0.11 mmol) in ethyl acetate (2 mL) at room temperature. After being stirred for 30 min, resulting white precipitate was filtered and washed with ethyl acetate to afford 45 mg (93%) of the title compound as a white powdery solid.

¹H-NMR in CDCl₃ showed two sets of signals in approximately 3:1 ratio.

¹H-NMR (CDCl₃) δ: 10.0 (0.2H, brs), 9.80 (0.7H, brs), 7.76 (2H, d, J=8.2 Hz), 7.40 (1H, t, J=8.2 Hz), 7.18 (2H, d, J=8.4H), 6.98 (1H, d, J=8.2 Hz), 6.56 (1H, d, J=8.1 Hz), 5.64 (1H, brs), 4.38 (0.5H, d, J=6.6 Hz), 4.25 (1.5H, d, J=6.8 Hz), 4.00-3.53 (8H, m), 3.32 (0.5H, s), 3.03 (2H, s), 2.90-2.70 (1.5H, m), 2.34 (3H, s), 2.30-1.55 (10H, m), 1.04 (6H, d, J=6.8 Hz).

MS (ESI) m/z: 419 (M-TsO)⁺, 171 (TsO)⁻.

m.p.: 161.8° C.

IR (KBr) v: 3513, 3028, 2959, 1614, 1533, 1435, 1371, 1285, 1094, 1037, 1013, 783 cm⁻¹.

Anal. Calcd for C₂₃H₃₄N₂O₅·C₇H₈O₃S·H₂O: C, 59.19; H, 7.29; N, 4.60. Found: C, 58.89; H, 7.23; N, 4.57.

Example 9

1-[(4-{[(4-Isobutoxy-1,2-benzisoxazol-3-yl)oxy]methyl}piperidin-1-yl)methyl]cyclopentane-carboxylic acid

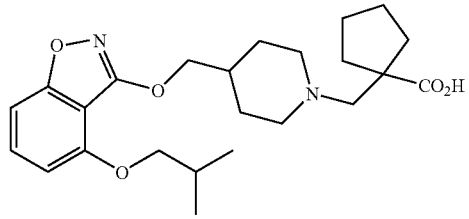 [SMILES: CC(C)COc1cccc2onc(OCC3CCN(CC4(C(=O)O)CCCC4)CC3)c12]

Step 1

Methyl 2-hydroxy-6-[(4-methoxybenzyl)oxy]benzoate

The title compound was prepared according to the procedure described in Step 1 of EXAMPLE 1 using 4-methoxybenzylchloride instead of 2,2,2-trifluoroethyl trifluoromethanesulfonate.

¹H-NMR (CDCl₃) δ: 11.48 (1H, s), 7.39 (2H, d, J=8.9 Hz), 7.33 (1H, t, J=8.4 Hz), 6.93 (2H, d, J=8.7 Hz), 6.61 (1H, dd, J=8.4, 1.0 Hz), 6.49 (1H, d, J=8.2 Hz), 5.05 (2H, s), 3.93 (3H, s), 3.83 (3H, s). TLC (silica gel, ethyl acetate/hexane 1:4) Rf: 0.44.

Step 2

4-[(4-Methoxybenzyl)oxy]-1,2-benzisoxazol-3-ol

The title compound was prepared according to the procedure described in Step 2 of EXAMPLE 8 using methyl 2-hydroxy-6-[(4-methoxybenzyl)oxy]benzoate (EXAMPLE 9, Step 1) instead of methyl 2-hydroxy-6-isobutoxybenzoate.

¹H-NMR (DMSO-d₆) δ: 7.48 (1H, t, J=8.2 Hz), 7.43 (2H, d, J=8.7 Hz), 7.06 (1H, d, J=8.4 Hz), 6.97 (2H, d, J=8.6 Hz), 6.85 (1H, d, J=8.1 Hz), 5.18 (2H, s), 3.76 (3H, s).

A signal due to OH was not observed.

TLC (silica gel, ethyl acetate/hexane 1:1) Rf: 0.28.

Step 3. Methyl 1-{[4-(hydroxymethyl)piperidin-1-yl]methyl}cyclopentanecarboxylate The title compound was prepared according to the procedure described in Step 3 of EXAMPLE 2 using piperidin-4-ylmethanol and methyl 1-formylcyclopentanecarboxylate (*Synthesis*, 1997, 32) instead of 3-(piperidin-4-ylmethoxy)-4-(2,2,2-trifluoroethoxy)-1,2-benzisoxazole and methyl 1-formylcyclobutanecarboxylate.

¹H-NMR (CDCl₃) δ: 3.66 (3H, s), 3.46 (2H, d, J=6.4 Hz), 2.81-2.77 (2H, m), 2.56 (2H, s), 2.11-2.02 (4H, m), 1.71-1.51 (8H, m), 1.50-1.11 (3H, m).

A signal due to OH was not observed.

MS (ESI) m/z: 256 (M+H)⁺.

Step 4

Methyl 1-({4-[({4-[(4-methoxybenzyl)oxy]-1,2-benzisoxazol-3-yl]oxy)methyl}piperidin-1-yl]methyl)-cyclopentanecarboxylate To a solution of 4-[(4-methoxybenzyl)oxy]-1,2-benzisoxazol-3-ol (100 mg, 0.369 mmol, EXAMPLE 9, step 2) and methyl 1-{[4-(hydroxymethyl)piperidin-1-yl]methyl}cyclopentanecarboxylate (141 mg, 0.553 mmol, EXAMPLE 9, step 3) in toluene (2.5 mL) was added cyanomethylenetributylphosphorane (178 mg, 0.737 mmol) at room temperature. The reaction mixture was heated at 100° C. for 20 h. After cooling, the mixture was concentrated in vacuo to give a dark brown oil. The residual oil was purified by silica gel column chromatography (hexane/ethyl acetate 5:2 to 3:2) to give 116 mg (62%) of the title compound as a white solid.

$^1$H-NMR (CDCl$_3$) δ: 7.42-7.37 (3H, m), 7.00 (1H, d, J=8.4 Hz), 6.94-6.89 (2H, m), 6.66 (1H, d, J=8.1 Hz), 4.21 (2H, d, J=7.0 Hz), 3.84 (3H, s), 3.67 (3H, s), 2.82-2.78 (2H, m), 2.58 (2H, s), 2.13-2.05 (4H, m), 1.93-1.70 (4H, m), 1.65-1.53 (7H, m), 1.38-1.24 (2H, m). TLC (silica gel, ethyl acetate/hexane 1:3) Rf: 0.35.

Step 5

Methyl 1-[(4-{[(4-hydroxy-1,2-benzisoxazol-3-yl)oxy]methyl}piperidin-1-yl)methyl]cyclopentanecarboxylate The title compound was prepared according to the procedure described in Step 6 of EXAMPLE 7 using methyl 1-({4-[({4-[(4-methoxybenzyl)oxy]-1,2-benzisoxazol-3-yl]oxy)methyl]piperidin-1-yl}methyl)cyclopentanecarboxylate (EXAMPLE 9, Step 4) instead of methyl 4-{[4-(2-{[4-(benzyloxy)-1,2-benzisoxazol-3-yl]oxy}ethyl)piperidin-1-yl]methyl}tetrahydro-2H-pyran-4-carbo xylate.

$^1$H-NMR (CDCl$_3$) δ: 7.39 (1H, dd, J=7.9, 8.4 Hz), 6.96 (1H, d, J=8.4 Hz), 6.56 (1H, d, J=7.9 Hz), 4.30 (2H, d, J=6.8 Hz), 3.67 (3H, s), 2.89-2.78 (2H, m), 2.59 (2H, s), 2.20-1.22 (15H, m).

A signal due to OH was not observed.

Step 6

Methyl 1-[(4-{[(4-isobutoxy-1,2-benzisoxazol-3-yl)oxy]methyl}piperidin-1-yl)methyl]cyclopentanecarboxylate The title compound was prepared according to the procedure described in Step 4 of EXAMPLE 9 using methyl 1-[(4-{[(4-hydroxy-1,2-benzisoxazol-3-yl)oxy]methyl}piperidin-1-yl)methyl]cyclopentanecarboxylate (EXAMPLE 9, Step 5) and isobutyl alcohol instead of 4-[(4-methoxybenzyl)oxy]-1,2-benzisoxazol-3-ol and methyl 1-{[4-(hydroxymethyl)piperidin-1-yl]methyl}cyclopentanecarboxylate.

$^1$H-NMR (CDCl$_3$) δ: 7.38 (1H, dd, J=7.9, 8.4 Hz), 6.97 (1H, d, J=8.4 Hz), 6.55 (1H, d, J=7.9 Hz), 4.22 (2H, d, J=6.4 Hz), 3.84 (2H, d, J=6.4 Hz), 3.67 (3H, s), 2.87-2.77 (2H, m), 2.58 (2H, s), 2.21-2.01 (5H, m), 1.95-1.24 (11H, m), 1.08 (6H, d, J=7.3 Hz).

MS (ESI) m/z: 445 (M+H)$^+$.

Step 7

1-[(4-{[(4-Isobutoxy-1,2-benzisoxazol-3-yl)oxy]methyl}piperidin-1-yl)methyl]cyclopentanecarboxylic acid The title compound was prepared according to the procedure described in Step 6 of EXAMPLE 1 using methyl 1-[(4-{[(4-isobutoxy-1,2-benzisoxazol-3-yl)oxy]methyl}piperidin-1-yl)methyl]cyclopentanecarboxylate (EXAMPLE 9, Step 6) instead of methyl 4-{[4-({[4-(2,2,2-trifluoroethoxy)-1,2-benzisoxazol-3-yl]oxy}methyl)piperidin-1-yl]methyl}tetrahydro-2H-pyra n-4-carboxylate.

$^1$H-NMR (DMSO-d$_6$) δ: 7.51 (1H, dd, J=8.1, 8.4 Hz), 7.10 (1H, d, J=8.4 Hz), 6.77 (1H, d, J=8.1 Hz), 4.20 (2H, d, J=5.9 Hz), 3.90 (2H, d, J=6.1 Hz), 2.98-2.87 (2H, m), 2.59 (s, 2H), 2.27-1.20 (16H, m), 1.03 (6H, d, J=6.6 Hz).

A signal due to CO$_2$H was not observed.
MS (ESI) m/z: 431 (M+H)$^+$, 429 (M−H)$^-$.
m.p.: 156.3° C.
IR (KBr) ν: 3449, 2951, 1611, 1529, 1369 cm$^{-1}$.
Anal. Calcd for $C_{24}H_{34}N_2O_5 \cdot H_2O$: C, 64.26; H, 8.09; N, 6.25. Found: C, 64.48; H, 8.31; N, 6.25.

Example 10

4-[(4-{[(4-Isobutoxy-1,2-benzisoxazol-3-yl)oxy]methyl}piperidin-1-yl)methyl]tetrahydro-2H-pyran-4-carboxylic acid

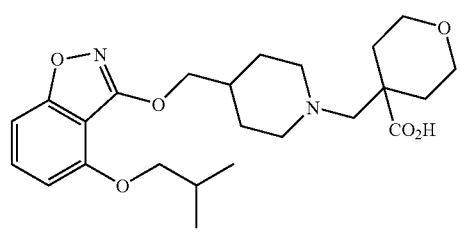 [SMILES: CC(C)COc1cccc2onc(OCC3CCN(CC4(C(=O)O)CCOCC4)CC3)c12]

Step 1

4-Isobutoxy-3-(piperidin-4-ylmethoxy)-1,2-benzisoxazole

The title compound was prepared according to the procedure described in Step 2 of EXAMPLE 2 using tert-butyl 4-{[(4-isobutoxy-1,2-benzisoxazol-3-yl)oxy]methyl}piperidine-1-carboxylate (EXAMPLE 8, Step 3) instead of tert-butyl 4-({[4-(2,2,2-trifluoroethoxy)-1,2-benzisoxazol-3-yl]oxy}methyl)piperidine-1-carboxylate.

$^1$H-NMR (CDCl$_3$) δ: 7.39 (1H, dd, J=7.9, 8.4 Hz), 6.97 (1H, d, J=8.4 Hz), 6.56 (1H, d, J=7.9 Hz), 4.25 (2H, d, J=6.8 Hz), 3.86 (2H, d, J=6.4 Hz), 3.20-3.09 (2H, m), 2.75-2.60 (2H, m), 2.25-1.82 (4H, m), 1.42-1.23 (2H, m), 1.08 (6H, d, J=6.8 Hz).

A signal due to NH was not observed.

Step 2

3-{[1-(Ethoxymethyl)piperidin-4-yl]methoxy}-4-isobutoxy-1,2-benzisoxazole

The title compound was prepared according to the procedure described in Step 4 of EXAMPLE 7 using 4-isobutoxy-3-(piperidin-4-ylmethoxy)-1,2-benzisoxazole (EXAMPLE 10, Step 1) instead of 4-(benzyloxy)-3-(2-piperidin-4-ylethoxy)-1,2-benzisoxazole.

¹H-NMR (CDCl₃) δ: 7.38 (1H, dd, J=7.9, 8.6 Hz), 6.97 (1H, d, J=8.6 Hz), 6.55 (1H, d, J=7.9 Hz), 4.25 (2H, d, J=6.6 Hz), 4.11 (2H, s), 3.85 (2H, d, J=5.9 Hz), 3.52 (2H, q, J=6.6 Hz), 3.03-2.88 (2H, m), 2.60-2.41 (2H, m), 2.23-1.14 (9H, m), 1.08 (6H, d, J=7.3 Hz).

Step 3

Methyl 4-[(4-{[(4-isobutoxy-1,2-benzisoxazol-3-yl)oxy]methyl}piperidin-1-yl)methyl]tetrahydro-2H-pyran-4-carboxylate The title compound was prepared according to the procedure described in Step 5 of EXAMPLE 7 using 3-{[1-(ethoxymethyl)piperidin-4-yl]methoxy}-4-isobutoxy-1,2-benzisoxazole (EXAMPLE 10, Step 2) instead of 4-(benzyloxy)-3-{2-[1-(ethoxymethyl)piperidin-4-yl]ethoxy}-1,2-benzisoxazole.

¹H-NMR (CDCl₃) δ: 7.38 (1H, dd, J=7.9, 8.6 Hz), 6.97 (1H, d, J=8.6 Hz), 6.55 (1H, d, J=7.9 Hz), 4.22 (2H, d, J=5.9 Hz), 3.89-3.78 (4H, m), 3.72 (3H, s), 3.54-3.40 (2H, m), 2.82-2.70 (2H, m), 2.51 (2H, s), 2.30-2.00 (5H, m), 1.93-1.30 (7H, m), 1.08 (6H, d, J=7.3 Hz).

Step 4

4-[(4-{[(4-Isobutoxy-1,2-benzisoxazol-3-yl)oxy]methyl}piperidin-1-yl)methyl]tetrahydro-2H-pyran-4-carboxylic acid The title compound was prepared according to the procedure described in Step 6 of EXAMPLE 1 using methyl 4-[(4-{[(4-isobutoxy-1,2-benzisoxazol-3-yl)oxy]methyl}piperidin-1-yl)methyl]tetrahydro-2H-pyran-4-carboxylate (EXAMPLE 10, Step 3) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

¹H-NMR (DMSO-d₆) δ: 7.51 (1H, dd, J=7.9, 8.6 Hz), 7.10 (1H, d, J=8.6 Hz), 6.77 (1H, d, J=7.9 Hz), 4.18 (2H, d, J=5.9 Hz), 3.89 (2H, d, J=5.9 Hz), 3.76-3.74 (2H, m), 3.50-3.25 (2H, m), 2.89-2.77 (2H, m), 2.50 (2H, s), 2.28-1.29 (12H, m), 1.03 (6H, d, J=6.6 Hz).

A signal due to CO₂H was not observed.

MS (ESI) m/z: 447 (M+H)⁻, 445 (M−H)⁺.

m.p.: 153.4° C.

IR (KBr) ν: 2951, 1617, 1526, 1376 cm⁻¹.

Anal. Calcd for C₂₄H₃₄N₂O₆: C, 64.55; H, 7.67; N, 6.27. Found: C, 64.50; H, 7.82; N, 6.16.

Example 11

3-(4-{[(4-Isobutoxy-1,2-benzisoxazol-3-yl)oxy]methyl}piperidin-1-yl)-2,2-dimethylpropanoic acid

Step 1

Methyl 3-(4-{[(4-isobutoxy-1,2-benzisoxazol-3-yl)oxy]methyl}piperidin-1-yl)-2,2-dimethylpropanoate The title compound was prepared according to the procedure described in Step 3 of EXAMPLE 2 using 4-isobutoxy-3-(piperidin-4-ylmethoxy)-1,2-benzisoxazole (EXAMPLE 10, Step 1) and methyl 2,2-dimethyl-3-oxopropanoate (0.96 mg, 0.74 mmol, *Tetrahedron Asymmetry* 2003, 14, 3371-3378) instead of 3-(piperidin-4-ylmethoxy)-4-(2,2,2-trifluoroethoxy)-1,2-benzisoxazole and methyl 1-formylcyclobutanecarboxylate.

¹H-NMR (CDCl₃) δ: 7.38 (1H, dd, J=7.9, 8.4 Hz), 6.97 (1H, d, J=8.4 Hz), 6.55 (1H, d, J=7.9 Hz), 4.23 (2H, d, J=6.2 Hz), 3.85 (2H, d, J=6.4 Hz), 3.66 (3H, s), 2.86-2.76 (2H, m), 2.49 (2H, s), 2.28-2.08 (3H, m), 1.94-1.68 (3H, m), 1.52-1.33 (2H, m), 1.17 (6H, s), 1.08 (6H, d, J=6.8 Hz).

MS (ESI) m/z: 419 (M+H)⁺.

Step 2

3-(4-{[(4-Isobutoxy-1,2-benzisoxazol-3-yl)oxy]methyl}piperidin-1-yl)-2,2-dimethylpropanoic acid The title compound was prepared according to the procedure described in Step 6 of EXAMPLE 1 using methyl 3-(4-{[(4-isobutoxy-1,2-benzisoxazol-3-yl)oxy]methyl}piperidin-1-yl)-2,2-dimethylpropanoate (EXAMPLE 11, Step 1) instead of methyl 4-{[4-({[4-(2,2,2-trifluoroethoxy)-1,2-benzisoxazol-3-yl]oxy}-methyl)piperidin-1-yl]methyl}tetrahydro-2H-pyran-4-carboxylate.

¹H-NMR (DMSO-d₆) δ: 7.51 (1H, dd, J=8.1, 8.4 Hz), 7.10 (1H, d, J=8.4 Hz), 6.78 (1H, d, J=8.1 Hz), 4.19 (2H, d, J=5.4 Hz), 3.89 (2H, d, J=6.1 Hz), 2.94-2.82 (2H, m), 2.46 (2H, s), 2.30-1.98 (3H, m), 1.87-1.64 (3H, m), 1.54-1.31 (2H, m), 1.07 (6H, s), 1.03 (6H, d, J=6.8 Hz).

A signal due to CO₂H was not observed.

MS (ESI) m/z: 405 (M+H)⁺, 403 (M−H)⁻.

m.p.: 123.7° C.

IR (KBr) ν: 3414, 2966, 1612, 1535, 1350 cm⁻¹.

Anal. Calcd for C₂₂H₃₂N₂O₅.0.37H₂O: C, 64.27; H, 8.03; N, 6.81. Found: C, 64.65; H, 8.43; N, 6.68.

Example 12

1-[(4-{[(4-Isobutoxy-1,2-benzisoxazol-3-yl)oxy]methyl}piperidin-1-yl)methyl]cyclobutanecarboxylic acid

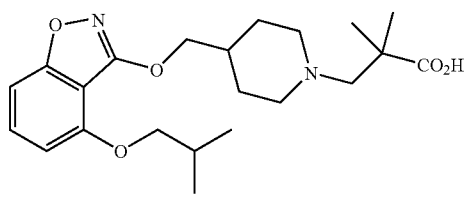 [SMILES: CC(C)COc1cccc2onc(OCC3CCN(CC(C)(C)C(=O)O)CC3)c12]

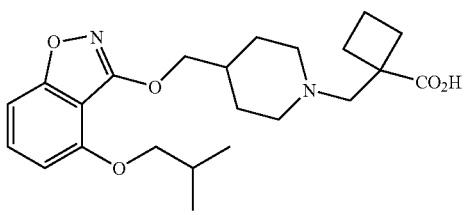 [SMILES: CC(C)COc1cccc2onc(OCC3CCN(CC4(C(=O)O)CCC4)CC3)c12]

Step 1

Methyl 1-[(4-{[(4-isobutoxy-1,2-benzisoxazol-3-yl)oxy]methyl}piperidin-1-yl)methyl]cyclobutanecarboxylate The title compound was prepared according to the procedure described in Step 3 of EXAMPLE 2 using 4-isobutoxy-3-(piperidin-4-ylmethoxy)-1,2-benzisoxazole (EXAMPLE 10, Step 1) instead of 3-(piperidin-4-ylmethoxy)-4-(2,2,2-trifluoroethoxy)-1,2-benzisoxazole.

$^1$H-NMR (CDCl$_3$) δ: 7.38 (1H, dd, J=7.9, 8.4 Hz), 6.97 (1H, d, J=8.4 Hz), 6.55 (1H, d, J=7.9 Hz), 4.22 (2H, d, J=6.6 Hz), 3.85 (2H, d, J=6.4 Hz), 3.71 (3H, s), 2.86-2.75 (2H, m), 2.71 (2H, s), 2.50-2.36 (2H, m), 2.23-1.70 (10H, m), 1.46-1.25 (2H, m), 1.07 (6H, d, J=6.8 Hz).

MS (ESI) m/z: 431 (M+H)$^+$.

Step 2

1-[(4-{[(4-Isobutoxy-1,2-benzisoxazol-3-yl)oxy]methyl}piperidin-1-yl)methyl]cyclobutanecarboxylic acid The title compound was prepared according to the procedure described in Step 6 of EXAMPLE 1 using methyl 1-[(4-{[(4-isobutoxy-1,2-benzisoxazol-3-yl)oxy]methyl}piperidin-1-yl)methyl]cyclobutane-carboxylate (EXAMPLE 12, Step 1) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

$^1$H-NMR (DMSO-d$_6$) δ: 7.51 (1H, dd, J=8.1, 8.4 Hz), 7.10 (1H, d, J=8.4 Hz), 6.78 (1H, d, J=8.1 Hz), 4.19 (2H, d, J=5.9 Hz), 3.89 (2H, d, J=6.1 Hz), 2.96-2.83 (2H, m), 2.73 (2H, s), 2.36-1.70 (12H, m), 1.47-1.26 (2H, m), 1.02 (6H, d, J=6.8 Hz).

A signal due to CO$_2$H was not observed.

MS (ESI) m/z: 417 (M+H)$^+$, 415 (M−H)$^-$.

m.p.: 168.8° C.

IR (KBr) ν: 3423, 2938, 1603, 1530, 1341 cm$^{-1}$.

Anal. Calcd for C$_{23}$H$_{32}$N$_2$O$_5$·1.1H$_2$O: C, 63.31; H, 7.90; N, 6.42. Found: C, 63.49; H, 8.30; N, 6.35.

Example 13

4-[2-(4-{[(4-Isobutoxy-1,2-benzisoxazol-3-yl)oxy]methyl}piperidin-1-yl)ethyl]tetrahydro-2H-pyran-4-carboxylic acid

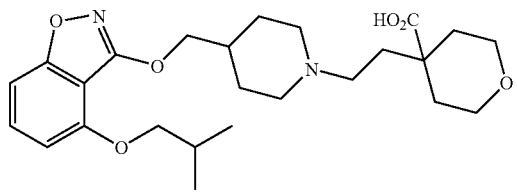 [SMILES: CC(C)COc1cccc2onc(OCC3CCN(CCC4(C(=O)O)CCOCC4)CC3)c12]

Step 1

Methyl 4-[2-(4-{[(4-isobutoxy-1,2-benzisoxazol-3-yl)oxy]methyl}piperidin-1-yl)ethyl]tetrahydro-2H-pyran-4-carboxylate The title compound was prepared according to the procedure described in Step 3 of EXAMPLE 2 using 4-isobutoxy-3-(piperidin-4-ylmethoxy)-1,2-benzisoxazole (EXAMPLE 10, Step 1) and methyl 4-(2-oxoethyl)tetrahydro-2H-pyran-4-carboxylate (WO 2004/043958) instead of 3-(piperidin-4-ylmethoxy)-4-(2,2,2-trifluoroethoxy)-1,2-benzisoxazole and methyl 1-formylcyclopentanecarboxylate.

$^1$H-NMR (CDCl$_3$) δ: 7.38 (1H, dd, J=8.1, 8.4 Hz), 6.97 (1H, d, J=8.4 Hz), 6.55 (1H, d, J=7.9 Hz), 4.23 (2H, d, J=6.6 Hz), 3.90-3.76 (4H, m), 3.72 (3H, s), 3.52-3.38 (2H, m), 2.99-2.86 (2H, m), 2.33-1.22 (16H, m) 1.07 (6H, d, J=6.8 Hz).

MS (ESI) m/z: 475 (M+H)$^+$.

Step 2

4-[2-(4-{[(4-Isobutoxy-1,2-benzisoxazol-3-yl)oxy]methyl}piperidin-1-yl)ethyl]tetrahydro-2H-pyran-4-carboxylic acid The title compound was prepared according to the procedure described in Step 6 of EXAMPLE 1 using methyl 4-[2-(4-{[(4-isobutoxy-1,2-benzisoxazol-3-yl)oxy]methyl}piperidin-1-yl)ethyl]tetrahydro-2H-pyran-4-carboxylate (EXAMPLE 13, Step 1) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

$^1$H-NMR (DMSO-d$_6$) δ: 7.51 (1H, dd, J=8.1, 8.2 Hz), 7.10 (1H, d, J=8.2 Hz), 6.77 (1H, d, J=8.1 Hz), 4.18 (2H, d, J=6.1 Hz), 3.90 (2H, d, J=6.1 Hz), 3.76-3.61 (2H, m), 3.45-3.29 (2H, m), 3.00-2.85 (2H, m), 2.38-2.23 (2H, m), 2.14-1.61 (10H, m), 1.50-1.23 (4H, m), 1.03 (6H, d, J=6.8 Hz).

A signal due to CO$_2$H was not observed.

MS (ESI) m/z: 461 (M+H)$^+$, 459 (M−H)

m.p.: 213.8° C.

IR (KBr) ν: 3431, 2930, 1611, 1529, 1433, 1287 cm$^{-1}$.

Anal. Calcd for C$_{25}$H$_{36}$N$_2$O$_6$: C, 65.20; H, 7.88; N, 6.08. Found: C, 64.82; H, 7.81; N, 6.01.

Example 14 trans-4-[(4-{[(4-Isobutoxy-1,2-benzisoxazol-3-yl)oxy]methyl}piperidin-1-yl)methyl]cyclohexanecarboxylic acid

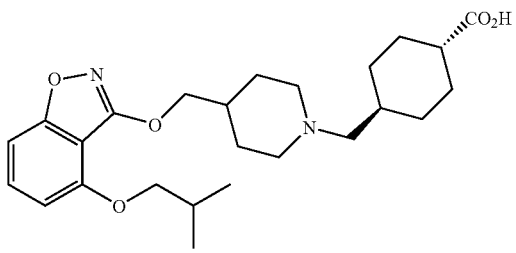 [SMILES: CC(C)COc1cccc2onc(OCC3CCN(C[C@H]4CC[C@H](C(=O)O)CC4)CC3)c12]

Step 1

Methyl trans-4-[(4-{[(4-isobutoxy-1,2-benzisoxazol-3-yl)oxy]methyl}piperidin-1-yl)methyl]-cyclohexanecarboxylate The title compound was prepared according to the procedure described in Step 3 of EXAMPLE 2 using 4-isobutoxy-3-(piperidin-4-ylmethoxy)-1,2-benzisoxazole (EXAMPLE 10, Step 1) and methyl trans-4-formylcyclohexanecarboxylate (JP 49048639) instead of 3-(piperidin-4-ylmethoxy)-4-(2,2,2-trifluoroethoxy)-1,2-benzisoxazole and methyl 1-formylcyclopentanecarboxylate.

$^1$H-NMR (CDCl$_3$) δ: 7.38 (1H, t, J=7.9 Hz), 6.97 (1H, d, J=7.9 Hz), 6.55 (1H, d, J=7.9 Hz), 4.25 (2H, d, J=5.9 Hz), 3.85 (2H, d, J=5.9 Hz), 3.67 (3H, s), 2.95-2.81 (2H, m), 2.33-1.77 (13H, m), 1.57-1.32 (5H, m), 1.08 (6H, d, J=6.6 Hz), 1.03-0.80 (2H, m).

Step 2 trans-4-[(4-{[(4-Isobutoxy-1,2-benzisoxazol-3-yl)oxy]methyl}piperidin-1-yl)methyl]cyclo-hexanecarboxylic acid The title compound was prepared according to the procedure described in Step 6 of EXAMPLE 1 using methyl trans-4-[(4-{[(4-isobutoxy-1,2-benzisoxazol-3-yl)oxy]methyl}piperidin-1-yl)methyl]-cyclohexanecarboxylate (EXAMPLE 14, Step 1) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

$^1$H-NMR (DMSO-d$_6$) δ: 7.51 (1H, dd, J=7.9, 8.6 Hz), 7.10 (1H, d, J=8.6 Hz), 6.77 (1H, d, J=7.9 Hz), 4.19 (2H, d, J=5.3 Hz), 3.89 (2H, d, J=6.6 Hz), 2.91-2.78 (2H, m), 2.20-1.65 (13H, m), 1.55-1.17 (5H, m), 1.03 (6H, d, J=6.6 Hz), 0.96-0.74 (2H, m).

A signal due to CO$_2$H was not observed.
MS (ESI) m/z: 445 (M+H)$^+$, 443 (M−H)$^−$.
m.p.: 103.3° C.
IR (KBr) ν: 3368, 2928, 1613, 1531, 1375 cm$^{-1}$.
Anal. Calcd for C$_{25}$H$_{36}$N$_2$O$_5$·2.5H$_2$O: C, 61.33; H, 8.44; N, 5.72. Found: C, 61.72; H, 8.18; N, 5.68.

Example 15

4-[(4-{2-[(4-isobutoxy-1,2-benzisoxazol-3-yl)oxy]ethyl}piperidin-1-yl)methyl]tetrahydro-2H-pyran-4-carboxylic acid

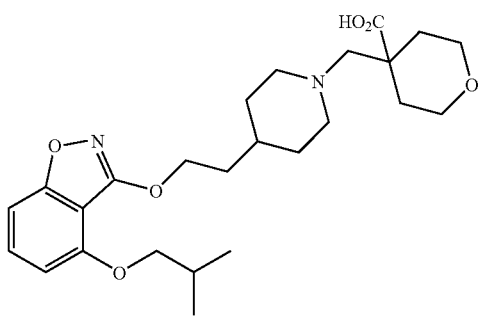 [SMILES: CC(C)COc1cccc2onc(OCCC3CCN(CC4(C(=O)O)CCOCC4)CC3)c12]

Step 1

Methyl 4-[(4-{2-[(4-isobutoxy-1,2-benzisoxazol-3-yl)oxy]ethyl}piperidin-1-yl)methyl]tetrahydro-2H-pyran-4-carboxylate The title compound was prepared according to the procedure described in Step 7 of EXAMPLE 7 using isobutyl bromide instead of 2,2,2-trifluoroethyl trifluoromethanesulfonate.

$^1$H-NMR (CDCl$_3$) δ: 7.39 (1H, dd, J=8.6, 7.9 Hz), 6.97 (1H, d, J=8.6 Hz), 6.56 (1H, d, J=7.9 Hz), 4.42 (2H, t, J=5.9 Hz), 3.89-3.77 (4H, m), 3.71 (3H, s), 3.53-3.39 (2H, m), 2.76-2.65 (2H, m), 2.48 (2H, s), 2.23-1.99 (5H, m), 1.83-1.44 (7H, m), 1.36-1.17 (2H, m), 1.08 (6H, d, J=6.6 Hz).

MS (ESI) m/z: 475 (M+H)$^+$.

Step 2

4-[(4-{2-[(4-Isobutoxy-1,2-benzisoxazol-3-yl)oxy]ethyl}piperidin-1-yl)methyl]tetrahydro-2H-pyran-4-carboxylic acid The title compound was prepared according to the procedure described in Step 6 of EXAMPLE 1 using methyl 4-[(4-{2-[(4-isobutoxy-1,2-benzisoxazol-3-yl)oxy]ethyl}piperidin-1-yl)methyl]tetrahydro-2H-pyran-4-carboxy late (EXAMPLE 15, Step 1) instead of methyl 4-{[4-({[4-(2,2,2-trifluoroethoxy)-1,2-benzisoxazol-3-yl]oxy}methyl)piperidin-1-yl]methyl}tetrahydro-2H-pyra n-4-carboxylate.

$^1$H-NMR (DMSO-d$_6$) δ: 7.51 (1H, dd, J=7.9, 8.6 Hz), 7.10 (1H, d, J=8.6 Hz), 6.77 (1H, d, J=7.9 Hz), 4.36 (2H, t, J=5.9 Hz), 3.90 (2H, d, J=6.6 Hz), 3.74-3.61 (2H, m), 3.48-3.31 (2H, m), 2.86-2.72 (2H, m), 2.47 (2H, s), 2.22-1.10 (14H, m), 1.03 (6H, d, J=6.6 Hz).

A signal due to CO$_2$H was not observed.
MS (ESI) m/z: 461 (M+H)$^+$, 459 (M−H)$^−$.
m.p.: 117.8° C.
IR (KBr) ν: 3431, 2912, 1612, 1534, 1433, 1355 cm$^{-1}$.
Anal. Calcd for C$_{25}$H$_{36}$N$_2$O$_6$: C, 65.20; H, 7.88; N, 6.08. Found: C, 65.19; H, 7.83; N, 6.02.

Example 16

4-[(4-{[(4-Isobutoxy-1,2-benzisoxazol-3-yl)amino]methyl}piperidin-1-yl)methyl]tetrahydro-2H-pyran-4-carboxylic acid

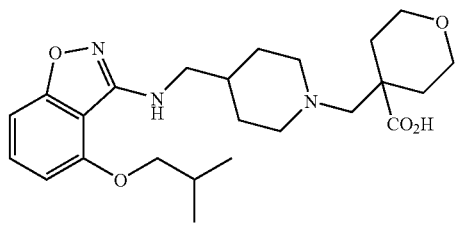 [SMILES: CC(C)COc1cccc2onc(NCC3CCN(CC4(C(=O)O)CCOCC4)CC3)c12]

Step 1

1-Fluoro-3-isobutoxybenzene

The title compound was prepared according to the procedure described in Step 7 of EXAMPLE 7 using 3-fluorophenol and isobutyl bromide instead of methyl 4-[(4-{2-[(4-hydroxy-1,2-benzisoxazol-3-yl)oxy]ethyl}piperidin-1-yl)methyl]tetrahydro-2H-pyran-4-carboxylate and 2,2,2-trifluoroethyl trifluoromethanesulfonate.

$^1$H-NMR (CDCl$_3$) δ: 7.25-7.15 (1H, m), 6.71-6.57 (3H, m), 3.70 (2H, d, J=6.6 Hz), 2.15-2.00 (1H, m), 1.02 (6H, d, J=6.8 Hz).

b.p: 80-85° C./15 mmHg

Step 2

2-Fluoro-6-isobutoxybenzaldehyde

To a solution of 1-fluoro-3-isobutoxybenzene (1.7 g, 10 mmol, EXAMPLE 16, Step 1) in tetrahydrofuran (15 mL) was added dropwise s-BuLi (0.99 M in cyclohexane, 12 mL, 12 mmol) at −78° C. under nitrogen atmosphere, and the mixture was stirred for 1 h. N,N-dimethylformamide (1.2 mL, 15 mmol) was added to the mixture, and the mixture was warm to −20° C. After being stirred at −20° C. for 1 h, the mixture was quenched with aq. sodium hydrogencarbonate (30 mL). The mixture was extracted with ethyl acetate (60 mL) and washed with water (30 mL). The extract was dried over magnesium sulfate and concentrated in vacuo to give an oil. The residual oil was purified by silica gel column chromatography (hexane/ethyl acetate 30:1) to give 1.2 g (61%) of the title compound as a colorless oil.

$^1$H-NMR (CDCl$_3$) δ: 10.50 (1H, s), 7.52-7.40 (1H, m), 6.79-6.66 (2H, m), 3.84 (2H, d, J=5.9 Hz), 2.25-2.08 (1H, m), 1.06 (6H, d, J=6.6 Hz).

Step 3

2-Fluoro-6-isobutoxybenzaldehyde oxime

50% aq. Sodium hydroxide (1.2 mL, 15.0 mmol) was added to a mixture of 2-fluoro-6-isobutoxybenzaldehyde (1.2 g, 6.1 mmol, EXAMPLE 16, Step 2) and hydroxylamine hydrochloride (0.47 g, 6.7 mmol) in ethanol (24 mL) and water (48 mL) at 0° C. The mixture was warmed to room temperature and stirred for 3 h. The mixture was neutrized with 2N hydrochloric acid and extracted with dichloromethane (100 mL×2). The combined extracts were dried over magnesium sulfate and concentrated in vacuo to give a solid. The residual solid was purified by silica gel column chromatography (hexane/ethyl acetate 9:1 to 6:1) to give 0.99 g (77%) of the title compound as a white solid.

$^1$H-NMR (DMSO-d$_6$) δ: 11.45 (1H, s), 8.21 (1H, s), 7.41-7.29 (1H, m), 6.95-6.80 (2H, m), 3.83 (2H, d, J=5.9 Hz), 2.15-1.95 (1H, m), 0.99 (6H, d, J=6.6 Hz).

Step 4

2-Fluoro-N-hydroxy-6-isobutoxybenzenecarboximidoyl chloride

To a solution of 2-fluoro-6-isobutoxybenzaldehyde oxime (0.99 g, 6.1 mmol, EXAMPLE 16, Step 3) in N,N-dimethylformamide (20 mL) was added N-chlorosuccinimide (0.63 g, 4.7 mmol) at 0° C. The mixture was heated at 50° C. for 1 h and cooled to room temperature. The mixture was diluted with ethylacetate (30 mL) and hexane (30 mL). The organic layer was washed with water (30 mL×2), dried over magnesium sulfate and concentrated in vacuo to give an oil. The residual oil was purified by silica gel column chromatography (hexane/ethyl acetate 9:1 to 4:1) to give 1.04 g (90%) of the title compound as a pale yellow oil.

$^1$H-NMR (CDCl$_3$) δ: 8.13-8.04 (1H, m), 7.43-7.28 (1H, m), 6.81-6.63 (2H, m), 3.86-3.73 (2H, m), 2.25-2.02 (1H, m), 1.12-0.97 (6H, m).

Step 5 tert-Butyl {[1-(ethoxymethyl)piperidin-4-yl]methyl}carbamate

The title compound was prepared according to the procedure described in Step 4 of EXAMPLE 7 using tert-butyl (piperidin-4-ylmethyl)carbamate instead of 4-(benzyloxy)-3-(2-piperidin-4-ylethoxy)-1,2-benzisoxazole.

$^1$H-NMR (CDCl$_3$) δ: 4.60 (1H, brs), 4.07 (2H, s), 3.49 (2H, q, J=7.1 Hz), 3.08-2.83 (4H, m), 2.50-2.36 (2H, m), 1.75-1.60 (2H, m), 1.44 (9H, s), 1.52-1.35 (1H, m), 1.19 (3H, t, J=7.1 Hz), 1.31-1.12 (2H, m).

Step 6

Methy 4-[(4-{[(tert-butoxycarbonyl)amino]methyl}piperidin-1-yl)methyl]tetrahydro-2H-pyran-4-carboxylate The title compound was prepared according to the procedure described in Step 5 of EXAMPLE 7 using tert-butyl {[1-(ethoxymethyl)piperidin-4-yl]methyl}carbamate (EXAMPLE 16, Step 5) instead of 4-(benzyloxy)-3-{2-[1-(ethoxymethyl)piperidin-4-yl]ethoxy}-1,2-benzisoxazole.

$^1$H-NMR (CDCl$_3$) δ: 4.57 (1H, br s), 3.84-3.78 (2H, m), 3.70 (3H, s), 3.49-3.41 (2H, m), 2.99-2.95 (2H, m), 2.73-2.68 (2H, m), 2.47 (2H, s), 2.19-2.11 (2H, m), 2.06-2.01 (2H, m), 1.61-1.51 (5H, m), 1.44 (9H, s), 1.24-1.11 (2H, m).

MS (ESI) m/z: 371 (M+H)$^+$.

Step 7

Methyl 4-{[4-(aminomethyl)piperidin-1-yl]methyl}tetrahydro-2H-pyran-4-carboxylate The title compound was prepared according to the procedure described in Step 2 of EXAMPLE 2 using methy 4-[(4-{[(tert-butoxycarbonyl)amino]methyl}piperidin-1-yl)methyl]tetrahydro-2H-pyran-4-carboxylate (EXAMPLE 16, Step 6) instead of tert-butyl 4-({[4-(2,2,2-trifluoroethoxy)-1,2-benzisoxazol-3-yl]oxy}methyl)piperidine-1-carboxylate.

$^1$H-NMR (CDCl$_3$) δ: 3.88-3.75 (2H, m), 3.71 (3H, s), 3.54-3.88 (2H, m), 2.78-2.65 (2H, m), 2.57-2.45 (2H, m), 2.24-1.98 (4H, m), 1.66-1.07 (9H, m). A signal due to NH$_2$ was not observed.

Step 8

Methyl 4-{[4-({[(2-fluoro-6-isobutoxyphenyl)hydroxyimino)methyl]amino}methyl)piperidin-1-yl]methyl}tetrahydro-2H-pyran-4-carboxylate To a solution of methyl 4-{[4-(aminomethyl)piperidin-1-yl]methyl}tetrahydro-2H-pyran-4-carboxylate (1.3 g, 4.8 mmol, EXAMPLE 16, Step 7) and triethylamine (0.67 mL, 4.8 mmol) in ethanol (10 mL) was added 2-fluoro-N-hydroxy-6-isobutoxybenzenecarboximidoyl chloride (0.77 g, 3.1 mmol, EXAMPLE 16, Step 4) at room temperature. After being stirred for 1.5 h, aq. sodium hydrogencarbonate (30 mL) was added to the mixture. The mixture was extracted with dichloromethane (50 mL×2). The combined extracts were dried over magnesium sulfate and concentrated in vacuo to give an oil. The residual oil was purified by silica gel column chromatography (hexane/ethyl acetate 3:2 to 1:4) to give 0.84 g (57%) of the title compound as a colorless viscous oil.

$^1$H-NMR (CDCl$_3$) δ: 7.37-7.23 (1H, m), 6.78-6.62 (2H, m), 5.43-5.28 (1H, m), 3.87-3.70 (4H, m), 3.68 (3H, s), 3.51-3.37 (2H, m), 2.77-2.58 (4H, m), 2.45 (2H, s), 2.18-1.94 (6H, m), 1.62-0.90 (12H, m). A signal due to OH was not observed.

Step 9

Methyl 4-[(4-{[(4-isobutoxy-1,2-benzisoxazol-3-yl)amino]methyl}piperidin-1-yl)methyl]tetrahydro-2H-pyran-4-carboxylate To a solution of methyl 4-{[4-({[(2-fluoro-6-isobutoxyphenyl)(hydroxyimino)methyl]amino}methyl)-piperidin-1-yl]methyl}tetrahydro-2H-pyran-4-carboxylate (0.84 g, 1.8 mmol, EXAMPLE 16, Step 8) in N-methylpyrrolidone (9.0 mL) was added potassium tert-butoxide (0.22 g, 2.0 mmol) at room temperature. The mixture was heated at 100° C. for 5 h and cooled to room temperature. The mixture was diluted with water (50 mL) and extracted with ethyl acetate (50 mL×2) and washed with water (50 mL). The combined extracts were dried over magnesium sulfate and concentrated in vacuo to give an oil. The residual oil was purified by silica gel column chromatography (hexane/ethyl acetate 1:1 to 1:2) to give 0.30 g (36%) of the title compound as a colorless viscous oil.

$^1$H-NMR (CDCl$_3$) δ: 7.33 (1H, dd, J=7.9, 8.6 Hz), 6.94 (1H, d, J=8.6 Hz), 6.50 (1H, d, J=7.9 Hz), 5.11-4.99 (1H, m), 3.97-3.65 (7H, m), 3.56-3.38 (2H, m), 3.33-3.19 (2H, m), 2.83-2.65 (2H, m), 2.49 (2H, s), 2.31-0.95 (18H, m).

Step 10

4-[(4-{[(4-Isobutoxy-1,2-benzisoxazol-3-yl)amino]methyl}piperidin-1-yl)methyl]tetrahydro-2H-pyran-4-carboxylic acid The title compound was prepared according to the procedure described in Step 6 of EXAMPLE 1 using methyl 4-[(4-{[(4-isobutoxy-1,2-benzisoxazol-3-yl)amino]methyl}piperidin-1-yl)methyl]tetrahydro-2H-pyran-4-carboxylate (EXAMPLE 16, Step 9) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

$^1$H-NMR (DMSO-d$_6$) δ: 7.42 (1H, t, J=8.2 Hz), 6.99 (1H, d, J=8.2 Hz), 6.72 (1H, d, J=8.2 Hz), 5.46 (1H, t, J=5.9 Hz), 3.93 (2H, d, J=6.6 Hz), 3.74-3.62 (2H, m), 3.47-3.30 (2H, m), 3.19-3.10 (2H, m), 2.86-2.74 (2H, m), 2.50 (2H, s), 2.27-2.06 (3H, m), 1.93-1.10 (9H, m), 1.01 (6H, d, J=6.6 Hz).

A signal due to CO$_2$H was not observed.

MS (ESI) m/z: 446 (M+H)$^+$, 444 (M–H)$^-$.

m.p.: 178.2° C.

IR (KBr) ν: 3421, 2951, 1603, 1091 cm$^{-1}$.

Anal. Calcd for C$_{24}$H$_{35}$N$_3$O$_5$.0.2H$_2$O: C, 64.18; H, 7.94; N, 9.36. Found: C, 64.28; H, 7.88; N, 9.36.

Example 17

1-{[4-({[4-(Cyclobutylmethoxy)-1,2-benzisoxazol-3-yl]oxy}methyl)piperidin-1-yl]methyl}cyclo-pentanecarboxylic acid

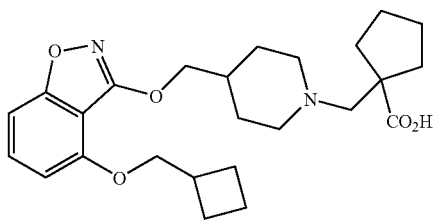 [SMILES: O=C(O)C1(CN2CCC(COc3noc4cccc(OCC5CCC5)c34)CC2)CCCC1]

Step 1 tert-Butyl 4-({[4-(benzyloxy)-1,2-benzisoxazol-3-yl]oxy}methyl)piperidine-1-carboxylate The title compound was prepared according to the procedure described in Step 3 of EXAMPLE 8 using 4-(benzyloxy)-1,2-benzisoxazol-3-ol (EXAMPLE 7, Step 1) and tert-butyl 4-(hydroxymethyl)-piperidine-1-carboxylate instead of 4-(benzyloxy)-1,2-benzisoxazol-3-ol and tert-butyl 4-(2-hydroxyethyl)-piperidine-1-carboxylate.

$^1$H-NMR (CDCl$_3$) δ: 7.50-7.30 (6H, m), 7.03 (1H, d, J=8.5 Hz), 6.68 (1H, d, J=7.9 Hz), 5.20 (2H, s), 4.26 (2H, brd, J=6.1 Hz), 4.14 (2H, br), 2.72 (2H, m), 2.05 (1H, m), 1.81 (2H, m), 1.47 (9H, s), 1.20-1.40 (2H, m).

MS (ESI) m/z: 339 (M+H—CO$_2$But)$^+$.

TLC (silica gel, hexane/ethyl acetate 3:1) Rf: 0.7.

Step 2 tert-Butyl 4-{[(4-hydroxy-1,2-benzisoxazol-3-yl)oxy]methyl}piperidine-1-carboxylate The title compound was prepared according to the procedure described in Step 6 of EXAMPLE 7 using tert-butyl 4-({[4-(benzyloxy)-1,2-benzisoxazol-3-yl]oxy}methyl)piperidine-1-carboxylate (EXAMPLE 17, Step 1) instead of methyl 4-{[4-(2-{[4-(benzyloxy)-1,2-benzisoxazol-3-yl]oxy}ethyl)piperidin-1-yl]methyl}tetrahydro-2H-pyran-4-carboxylate.

$^1$H-NMR (DMSO-d$_6$) δ: 7.38 (1H, t, J=8.3 Hz), 6.94 (1H, d, J=7.9 Hz), 6.64 (1H, d, J=8.3 Hz), 4.21 (2H, brd, J=6.6 Hz), 3.99 (2H, m), 2.76 (2H, br), 2.05 (1H, br), 1.76 (2H, m), 1.40 (9H, s), 1.05-1.30 (2H, m).

A signal due to OH was not observed.

MS (ESI) m/z: 347 (M–H)$^-$.

Step 3 tert-Butyl 4-({[4-(cyclobutylmethoxy)-1,2-benzisoxazol-3-yl]oxy}methyl)piperidine-1-carboxylate The title compound was prepared according to the procedure described in Step 7 of EXAMPLE 7 using tert-butyl 4-{[(4-hydroxy-1,2-benzisoxazol-3-yl)oxy]methyl}piperidine-1-carboxylate (EXAMPLE 17, Step 2) and (bromomethyl)cyclobutane instead of methyl 4-[(4-{2-[(4-hydroxy-1,2-benzisoxazol-3-yl)oxy]ethyl}piperidin-1-yl)methyl]tetrahydro-2H-pyran-4-carboxylate and 2,2,2-trifluoroethyl trifluoromethanesulfonate (Step 7 of EXAMPLE 7).

$^1$H-NMR (CDCl$_3$) δ: 7.39 (1H, t, J=8.2 Hz), 6.98 (1H, d, J=8.2 Hz), 6.57 (1H, d, J=8.2 Hz), 4.27 (2H, d, J=6.2 Hz), 4.03 (2H, d, J=5.9 Hz), 2.91-2.65 (3H, m) 2.17-1.91 (8H, m), 1.91-1.78 (2H, m), 1.47 (9H, s), 1.44-1.30 (2H, m).

MS (ESI) m/z: 417 (M+H)$^+$.

Step 4

4-(Cyclobutylmethoxy)-3-(Piperidin-4-ylmethoxy)-1,2-benzisoxazole

The title compound was prepared according to the procedure described in Step 2 of EXAMPLE 2 using tert-butyl 4-({[4-(cyclobutylmethoxy)-1,2-benzisoxazol-3-yl]oxy}methyl)piperidine-1-carboxylate (EXAMPLE 17, Step 3) instead of tert-butyl 4-({[4-(2,2,2-trifluoroethoxy)-1,2-benzisoxazol-3-yl]-oxy}methyl)piperidine-1-carboxylate.

$^1$H-NMR (CDCl$_3$) δ: 7.38 (1H, t, J=8.2 Hz), 6.97 (1H, d, J=8.2 Hz), 6.56 (1H, d, J=8.2 Hz), 4.24 (2H, d, J=6.6 Hz), 4.03 (2H, d, J=5.9 Hz), 3.24-3.03 (2H, m) 2.92-2.74 (1H, m), 2.74-2.58 (2H, m), 2.20-1.80 (9H, m), 1.40-1.23 (2H, m).

A signal due to NH was not observed.

MS (ESI) m/z: 317 (M+H)$^+$.

Step 5

Methyl 1-{[4-({[4-(cyclobutylmethoxy)-1,2-benzisoxazol-3-yl]oxy}methyl piperidin-1-yl]methyl}-cyclopentanecarboxylate The title compound was prepared according to the procedure described in Step 3 of EXAMPLE 2 using 4-(cyclobutylmethoxy)-3-(piperidin-4-ylmethoxy)-1,2-benzisoxazole (EXAMPLE 17, Step 4) and methyl 1-formylcyclopentanecarboxylate (*Synthesis* 1997, 32-34) instead of 3-(piperidin-4-ylmethoxy)-4-(2,2,2-trifluoroethoxy)-1,2-benzisoxazole and methyl 1-formylcyclobutanecarboxylate.

$^1$H-NMR (CDCl$_3$) δ: 7.38 (1H, t, J=8.3 Hz), 6.97 (1H, d, J=8.4 Hz), 6.56 (1H, d, J=8.1 Hz), 4.22 (2H, d, J=6.4 Hz), 4.02 (2H, d, J=5.9 Hz), 3.67 (3H, s), 2.85-2.80 (3H, m), 2.16-1.54 (21H, m), 1.45-1.31 (2H, m).

MS (ESI) m/z: 457 (M+H)$^+$.

Step 6

1-{[4-({[4-(Cyclobutylmethoxy)-1,2-benzisoxazol-3-yl]oxy}methyl)piperidin-1-yl]methyl}cyclopentanecarboxylic acid The title compound was prepared according to the procedure described in Step 6 of EXAMPLE 1 using methyl 1-{[4-({[4-(cyclobutylmethoxy)-1,2-benzisoxazol-3-yl]oxy}methyl)piperidin-1-yl]methyl}-cyclopentanecarboxylate (EXAMPLE 17, Step 5) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

$^1$H-NMR (DMSO-d$_6$) δ: 7.51 (1H, t, J=8.3 Hz), 7.10 (1H, d, J=8.4 Hz), 6.78 (1H, d, J=8.1 Hz), 4.19 (2H, d, J=5.5 Hz), 4.05 (2H, d, J=5.7 Hz), 2.96-2.88 (2H, m), 2.82-2.72 (1H, m), 2.58 (2H, s), 2.22-1.70 (13H, m), 1.60-1.31 (8H, m).

A signal due to CO$_2$H was not observed.

MS (ESI) m/z: 443 (M+H)$^+$, 441 (M−H)$^−$.

m.p.: 173.8° C.

IR (KBr) v: 2942, 1612, 1532, 1434, 1369, 1292 cm$^{-1}$.

Anal. Calcd for C$_{25}$H$_{34}$N$_2$O$_5$·1.1H$_2$O: C, 64.94; H, 7.89; N, 6.06. Found: C, 64.58; H, 7.71; N, 5.99.

Example 18

4-{[4-({[4-(Cyclobutylmethoxy)-1,2-benzisoxazol-3-yl]oxy}methyl)piperidin-1-yl]methyl}tetrahydro-2H-pyran-4-carboxylic acid

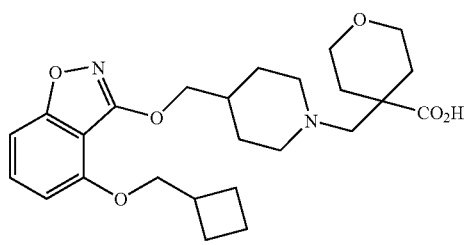 [SMILES: O=C(O)C1(CN2CCC(COc3noc4cccc(OCC5CCC5)c34)CC2)CCOCC1]

Step 1

Methyl 4-formyltetrahydro-2H-pyran-4-carboxylate

To a solution of dimethyl tetrahydro-4H-pyran-4,4-dicarboxylate (3.9 g, 19.3 mmol) in dichloromethane (38 mL) was added dropwise a 1.01 M solution of diisobutylalminium hydride in toluene (38.2 mL, 38.6 mmol) at −78° C. over 30 min period. After being stirred at this temperature for 3 h, the mixture was quenched with followed by addition of aq. ammonium chloride and 2N hydrochloric acid. The mixture was allowed to warm to room temperature and filtered through a pad of celite. The filtrate was washed with water and dried over sodium sulfate and concentrated in vacuo to give an oil. The residual oil was purified by silica gel column chromatography (hexane/ethylacetate 5:1) to afforded 2.14 g (64%) of the title compound as a colorless oil.

$^1$H-NMR (CDCl$_3$) δ: 9.57 (1H, s), 3.80 (3H, s), 3.69 (4H, t, J=5.1 Hz), 2.19-2.11 (2H, m), 2.07-1.98 (2H, m).

Step 2

Methyl 4-{[4-({[4-(cyclobutylmethoxy)-1,2-benzisoxazol-3-yl]oxy}methyl)piperidin-1-yl]methyl}tetrahydro-2H-pyran-4-carboxylate The title compound was prepared according to the procedure described in Step 3 of EXAMPLE 2 using 4-(cyclobutylmethoxy)-3-(piperidin-4-ylmethoxy)-1,2-benzisoxazole (EXAMPLE 17, Step 4) and methyl 4-formyltetrahydro-2H-pyran-4-carboxylate (EXAMPLE 18, Step 1) instead of 3-(piperidin-4-ylmethoxy)-4-(2,2,2-trifluoroethoxy)-1,2-benzisoxazole and methyl 1-formylcyclobutanecarboxylate.

$^1$H-NMR (CDCl$_3$) δ: 7.38 (1H, t, J=8.2 Hz), 6.97 (1H, d, J=8.2 Hz), 6.56 (1H, d, J=8.2 Hz), 4.22 (2H, d, J=6.4 Hz), 4.03 (2H, d, J=5.7 Hz) 3.82 (2H, dt, J=11.6, 3.3, 3.3 Hz), 3.72 (3H, s), 3.47 (2H, td, 11.6, 11.6, 2.2 Hz), 2.89-2.70 (3H, m), 2.51 (2H, s), 2.30-2.16 (2H, m), 2.15-1.70 (11H, m), 1.66-1.50 (2H, m), 1.48-1.30 (2H, m).

MS (ESI) m/z: 473 (M+H)$^+$.

Step 3

4-{[4-({[4-(Cyclobutylmethoxy)-1,2-benzisoxazol-3-yl]oxy}methyl)piperidin-1-yl]-methyl}tetrahydro-2H-pyran-4-carboxylic acid The title compound was prepared according to the procedure described in Step 6 of EXAMPLE 1 using methyl 4-{[4-({[4-(cyclobutylmethoxy)-1,2-benzisoxazol-3-yl]oxy}methyl)piperidin-1-yl]methyl}-tetrahydro-2H-pyran-4-carboxylate (EXAMPLE 18, Step 2) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

$^1$H-NMR (CDCl$_3$) δ: 7.40 (1H, t, J=8.1 Hz), 6.98 (1H, d, J=8.1 Hz), 6.58 (1H, d, J=8.1 Hz), 4.29 (2H, d, J=6.1 Hz), 4.04 (2H, d, J=5.9 Hz) 3.96-3.74 (4H, m), 3.22-3.07 (2H, m), 2.94-2.74 (1H, m), 2.66-2.48 (2H, m), 2.60 (2H, s), 2.21-1.84 (11H, m), 1.72-1.40 (4H, m).

A signal due to CO$_2$H was not observed.

MS (ESI) m/z: 459 (M+H)$^+$, 457 (M−H)$^−$.

m.p.: 175.5° C.

IR (KBr) v: 2942, 1611, 1533, 1431, 1368, 1284, 1096, 976, 787 cm$^{-1}$

Anal. Calcd for C$_{25}$H$_{34}$N$_2$O$_6$: C, 65.48; H, 7.47; N, 6.11. Found: C, 65.55; H, 7.57; N, 6.01.

Example 19

3-[4-({[4-(Cyclobutylmethoxy)-1,2-benzisoxazol-3-yl]oxy}methyl)piperidin-1-yl]-2,2-dimethyl-propanoic acid

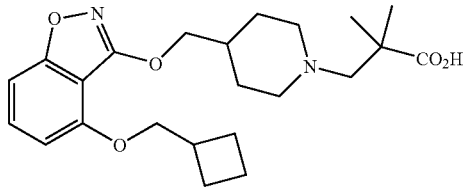 [SMILES: CC(C)(CN1CCC(COc2noc3cccc(OCC4CCC4)c23)CC1)C(=O)O]

Step 1

Methyl 3-[4-({[4-(cyclobutylmethoxy)-1,2-benzisoxazol-3-yl]oxy}methyl)piperidin-1-yl]-2,2-dimethyl-propanoate The title compound was prepared according to the procedure described in Step 3 of EXAMPLE 2 using 4-(cyclobutylmethoxy)-3-(piperidin-4-ylmethoxy)-1,2-benzisoxazole (EXAMPLE 17, Step 4) and methyl 2,2-dimethyl-3-oxopropanoate (*Tetrahedron Asymmetry* 2003, 14, 3371-3378) instead of 3-(piperidin-4-ylmethoxy)-4-(2,2,2-trifluoroethoxy)-1,2-benzisoxazole and methyl 1-formylcyclobutancarboxylate.

$^1$H-NMR (CDCl$_3$) δ: 7.38 (1H, t, J=8.2 Hz), 6.97 (1H, d, J=8.2 Hz), 6.56 (1H, d, J=8.2 Hz), 4.23 (2H, d, J=6.4 Hz), 4.03 (2H, d, J=5.9 Hz), 3.66 (3H, s), 2.90-2.74 (3H, m) 2.49 (2H, s), 2.30-1.68 (11H, m), 1.60-1.31 (2H, m), 1.17 (6H, s).

MS (ESI) m/z: 431 (M+H)$^+$.

Step 2

3-[4-({[4-(Cyclobutylmethoxy)-1,2-benzisoxazol-3-yl]oxy}methyl)piperidin-1-yl]-2,2-dimethylpropanoic acid The title compound was prepared according to the procedure described in Step 6 of EXAMPLE 1 using methyl 3-[4-({[4-(cyclobutylmethoxy)-1,2-benzisoxazol-3-yl]oxy}methyl)piperidin-1-yl]-2,2-dimethylpropanoate (EXAMPLE 19, Step 1) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

$^1$H-NMR (CDCl$_3$) δ: 7.40 (1H, t, J=8.3 Hz), 6.98 (1H, d, J=8.3 Hz), 6.58 (1H, d, J=8.3 Hz), 4.29 (2H, d, J=6.6 Hz), 4.04 (2H, d, J=6.1 Hz) 3.25-3.10 (2H, m), 2.95-2.75 (1H, m), 2.58 (2H, s), 2.65-2.40 (2H, m), 2.20-1.80 (9H, m), 1.70-1.45 (2H, m), 1.25 (6H, s).

A signal due to CO$_2$H was not observed.

MS (ESI) m/z: 417 (M+H)$^+$, 415 (M+H)$^-$.

m.p.: 139.8° C.

IR (KBr) v: 2930, 1600, 1531, 1436, 1374, 1343, 1291, 1114, 1089, 786 cm$^{-1}$

Anal. Calcd for C$_{23}$H$_{32}$N$_2$O$_5$.0.4H$_2$O: C, 65.20; H, 7.80; N, 6.61. Found: C, 65.00; H, 7.95; N, 6.48.

Example 20

1-{[4-({[4-(Cyclobutylmethoxy)-1,2-benzisoxazol-3-yl]oxy}methyl)piperidin-1-yl]methyl}cyclo-butanecarboxylic acid

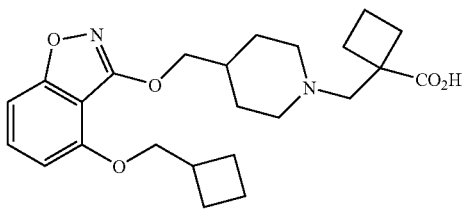 [SMILES: O=C(O)C1(CN2CCC(COc3noc4cccc(OCC5CCC5)c34)CC2)CCC1]

Step 1

Methyl 1-{[4-({[4-(cyclobutylmethoxy)-1,2-benzisoxazol-3-yl]oxy}methyl)piperidin-1-yl]methyl}-cyclobutanecarboxylate The title compound was prepared according to the procedure described in Step 3 of EXAMPLE 2 using 4-(cyclobutylmethoxy)-3-(piperidin-4-ylmethoxy)-1,2-benzisoxazole (EXAMPLE 17, Step 4) instead of 3-(piperidin-4-ylmethoxy)-4-(2,2,2-trifluoroethoxy)-1,2-benzisoxazole.

$^1$H-NMR (CDCl$_3$) δ: 7.38 (1H, t, J=8.2 Hz), 6.97 (1H, d, J=8.2 Hz), 6.56 (1H, d, J=8.2 Hz), 4.21 (2H, d, J=6.4 Hz), 4.02 (2H, d, J=5.8 Hz), 3.71 (3H, s), 2.87-2.73 (3H, m) 2.71 (2H, s), 2.55-2.35 (3H, m), 2.20-1.65 (14H, m), 1.46-1.23 (2H, m).

MS (ESI) m/z: 443 (M+H)$^+$.

Step 2

1-{[4-({[4-(Cyclobutylmethoxy)-1,2-benzisoxazol-3-yl]oxy}methyl)piperidin-1-yl]methyl}cyclo-butanecarboxylic acid The title compound was prepared according to the procedure described in Step 6 of EXAMPLE 1 using methyl 1-{[4-({[4-(cyclobutylmethoxy)-1,2-benzisoxazol-3-yl]oxy}methyl)piperidin-1-yl]methyl}-cyclobutanecarboxylate (EXAMPLE 20, Step 1) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

$^1$H-NMR (CDCl$_3$) δ: 7.40 (1H, t, J=8.4 Hz), 6.98 (1H, d, J=8.4 Hz), 6.57 (1H, d, J=8.4 Hz), 4.28 (2H, d, J=6.2 Hz), 4.04 (2H, d, J=6.1 Hz) 3.14-3.00 (2H, m), 2.90-2.73 (1H, m), 2.79 (2H, s), 2.61-2.52 (2H, m), 2.46-2.25 (2H, m), 2.20-1.83 (13H, m), 1.67-1.43 (2H, m). A signal due to CO$_2$H was not observed.

MS (ESI) m/z: 429 (M+H)$^+$, 427 (M-H)$^-$.

m.p.: 176.9° C.

IR (KBr) v: 2942, 1614, 1533, 1436, 1369, 1295, 1118, 1080, 787 cm$^{-1}$

Anal. Calcd for C$_{24}$H$_{32}$N$_2$O$_5$.0.35H$_2$CO$_3$.0.2H$_2$O: C, 64.44; H, 7.35; N, 6.17. Found: C, 64.16; H, 7.20; N, 6.18.

Example 21

4-{2-[4-({[4-(cyclobutylmethoxy)-1,2-benzisoxazol-3-yl]oxy}methyl)piperidin-1-yl]ethyl}tetrahydro-2H-pyran-4-carboxylic acid

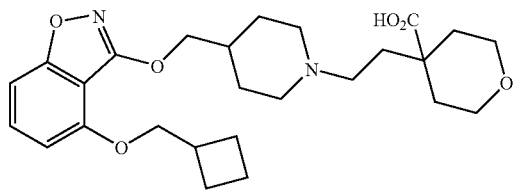 [SMILES: O=C(O)C1(CCN2CCC(COc3noc4cccc(OCC5CCC5)c34)CC2)CCOCC1]

Step 1

Methyl 4-{2-[4-({[4-(cyclobutylmethoxy)-1,2-benzisoxazol-3-yl]oxy}methyl)piperidin-1-yl]ethyl}-tetrahydro-2H-pyran-4-carboxylate The title compound was prepared according to the procedure described in Step 3 of EXAMPLE 2 using 4-(cyclobutylmethoxy)-3-(piperidin-4-ylmethoxy)-1,2-benzisoxazole (EXAMPLE 17, Step 4) and methyl 4-(2-oxoethyl)tetrahydro-2H-pyran-4-carboxylate (WO 2004/043958) instead of 3-(piperidin-4-ylmethoxy)-4-(2,2,2-trifluoroethoxy)-1,2-benzisoxazole and methyl 1-formylcyclobutanecarboxylate.

$^1$H-NMR (CDCl$_3$)) δ: 7.39 (1H, dd, J=8.4, 7.9 Hz), 6.97 (1H, d, J=8.4 Hz), 6.56 (1H, d, J=7.9 Hz), 4.23 (2H, d, J=6.4 Hz), 4.03 (2H, d, J=5.6 Hz), 3.89-3.77 (2H, m), 3.72 (3H, s), 3.52-3.38 (2H, m), 3.00-2.75 (2H, m), 2.34-1.29 (22H, m).

MS (ESI) m/z: 475 (M+H)$^+$.

Step 2

4-{2-[4-({[4-(cyclobutylmethoxy)-1,2-benzisoxazol-3-yl]oxy}methyl)piperidin-1-yl]ethyl}-tetrahydro-2H-pyran-4-carboxylic acid The title compound was prepared according to the procedure described in Step 6 of EXAMPLE 1 using methyl 4-{2-[4-({[4-(cyclobutylmethoxy)-1,2-benzisoxazol-3-yl]oxy}methyl)piperidin-1-yl]ethyl}-tetrahydro-2H-pyran-4-carboxylate (EXAMPLE 21, Step 1) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

$^1$H-NMR (DMSO-d$_6$): 7.51 (1H, dd, J=8.1, 8.4 Hz), 7.10 (1H, d, J=8.4 Hz), 6.77 (1H, d, J=8.1 Hz), 4.18 (2H, d, J=5.9 Hz), 4.05 (2H, d, J=5.6 Hz), 3.75-3.63 (2H, m), 3.44-3.30 (2H, m), 2.99-2.71 (2H, m), 2.35-2.24 (2H, m), 2.14-1.61 (16H, m), 1.49-1.26 (4H, m).

A signal due to CO$_2$H was not observed.

MS (ESI) m/z: 473 (M+H)$^+$, 471 (M−H)$^−$.

m.p.: 223.2° C.

IR (KBr) ν: 3431, 2939, 1613, 1528, 1434, 1374 cm$^{-1}$.

Anal. Calcd for C$_{26}$H$_{36}$N$_2$O$_6$: C, 66.08; H, 7.68; N, 5.93. Found: C, 66.00; H, 7.73; N, 5.83.

Example 22

4-{[4-({[4-(Cyclopentylmethoxy)-1,2-benzisoxazol-3-yl]oxy}methyl)piperidin-1-yl]methyl}tetrahydro-2H-pyran-4-carboxylic acid

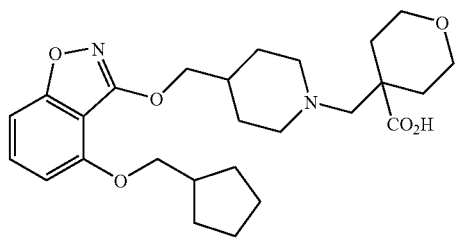 [SMILES: O=C(O)C1(CN2CCC(COc3noc4cccc(OCC5CCCC5)c34)CC2)CCOCC1]

Step 1 tert-Butyl 4-({[4-(cyclopentylmethoxy)-1,2-benzisoxazol-3-yl]oxy}methyl)piperidine-1-carboxylate The title compound was prepared according to the procedure described in Step 4 of EXAMPLE 9 using tert-butyl 4-{[(4-hydroxy-1,2-benzisoxazol-3-yl)oxy]methyl}piperidine-1-carboxylate (EXAMPLE 17, Step 2) and cyclopentylmethanol instead of 4-[(4-methoxybenzyl)oxy]-1,2-benzisoxazol-3-ol and methyl 1-{[4-(hydroxymethyl)piperidin-1-yl]methyl}cyclopentanecarboxylate.

$^1$H-NMR (CDCl$_3$) δ: 7.42-7.36 (1H, m), 6.97 (1H, d, J=8.4 Hz), 6.57 (1H, d, J=7.9 Hz), 4.28-4.05 (4H, m), 3.97 (2H, d, J=6.4 Hz), 2.82-2.71 (2H, m), 2.47-2.36 (1H, m), 2.14-2.01 (1H, m), 1.93-1.76 (4H, m), 1.71-1.56 (5H, m), 1.47 (9H, s), 1.43-1.23 (3H, m). TLC (silica gel, ethyl acetate/hexane 1:1) Rf: 0.67.

Step 2

4-(Cyclopentylmethoxy)-3-(piperidin-4-ylmethoxy)-1,2-benzisoxazole

The title compound was prepared according to the procedure described in Step 2 of EXAMPLE 2 using tert-butyl 4-({[4-(cyclopentylmethoxy)-1,2-benzisoxazol-3-yl]oxy}methyl)piperidine-1-carboxylate (EXAMPLE 22, Step 1) instead of tert-butyl 4-({[4-(2,2,2-trifluoroethoxy)-1,2-benzisoxazol-3-yl]oxy}methyl)piperidine-1-carboxylate.

$^1$H-NMR (CDCl$_3$) δ: 7.41-7.36 (1H, m), 6.97 (1H, d, J=8.4 Hz), 6.57 (1H, d, J=8.1 Hz), 4.24 (2H, d, J=6.8 Hz), 3.98 (2H, d, J=6.4 Hz), 3.17-3.12 (2H, m), 2.71-2.62 (2H, m), 2.47-2.36 (1H, m), 2.16-1.98 (1H, m), 1.96-1.79 (4H, m), 1.77-1.56 (6H, m), 1.38-1.24 (2H, m).

A signal due to N$\underline{H}$ was not observed.

TLC (silica gel, ethyl acetate/hexane 1:1) Rf: 0.1.

Step 3

Methyl 4-{[4-({[4-(cyclopentylmethoxy)-1,2-benzisoxazol-3-yl]oxy}methyl)piperidin-1-yl]methyl}tetrahydro-2H-pyran-4-carboxylate The title compound was prepared according to the procedure described in Step 3 of EXAMPLE 2 using 4-(cyclopentylmethoxy)-3-(piperidin-4-ylmethoxy)-1,2-benzisoxazole (EXAMPLE 22, Step 2) and methyl 4-formyltetrahydro-2H-pyran-4-carboxylate (EXAMPLE 18, Step 1) instead of 3-(piperidin-4-ylmethoxy)-4-(2,2,2-trifluoroethoxy)-1,2-benzisoxazole and methyl 1-formylcyclobutanecarboxylate.

$^1$H-NMR (CDCl$_3$) δ: 7.40-7.35 (1H, m), 6.96 (1H, d, J=8.4 Hz), 6.56 (1H, d, J=8.1 Hz), 4.21 (2H, d, J=6.6 Hz), 3.97 (2H, d, J=6.4 Hz), 3.85-3.66 (4H, m), 3.72 (3H, s), 3.51-3.43 (2H, m), 2.79-2.75 (2H, m), 2.52 (2H, s), 2.46-2.04 (5H, m), 1.89-1.31 (13H, m). TLC (silica gel, ethyl acetate/hexane 1:1) Rf: 0.52.

Step 4

4-{[4-({[4-(Cyclopentylmethoxy)-1,2-benzisoxazol-3-yl]oxy}methyl)piperidin-1-yl]methyl}-tetrahydro-2H-pyran-4-carboxylic acid The title compound was prepared according to the procedure described in Step 6 of EXAMPLE 1 using methyl 4-{[4-({[4-(cyclopentylmethoxy)-1,2-benzisoxazol-3-yl]oxy}methyl)piperidin-1-yl]methyl}-tetrahydro-2H-pyran-4-carboxylate (EXAMPLE 22, Step 3) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

$^1$H-NMR (CDCl$_3$) δ: 7.43-7.37 (1H, m), 6.98 (1H, d, J=8.4 Hz), 6.58 (1H, d, J=8.1 Hz), 4.28 (2H, d, J=6.4 Hz), 3.98-3.93 (2H, m), 3.91-3.77 (4H, m), 3.18-3.11 (2H, m), 2.59-2.38 (5H, m), 2.14-1.76 (7H, m), 1.71-1.36 (10H, m).

A signal due to CO$_2$H was not observed.
MS (ESI) m/z: 473 (M+H)$^+$, 471 (M−H)$^−$.
m.p.: 185.6° C.
IR (KBr) ν: 2942, 1734, 1611, 1533, 1504, 1435, 1342, 1285, 1217, 1200, 1177, 1096, 1057, 1030, 991, 918, 868, 829, 787, 745, 658 cm$^{−1}$.
Anal. Calcd for C$_{26}$H$_{36}$N$_2$O$_6$·0.5H$_2$O: C, 64.84; H, 7.74; N, 5.82. Found: C, 64.49; H, 7.62; N, 5.47.

Example 23

4-{2-[4-({[4-(Cyclopentylmethoxy)-1,2-benzisoxazol-3-yl]oxy}methyl)piperidin-1-yl]ethyl}tetrahydro-2H-pyran-4-carboxylic acid

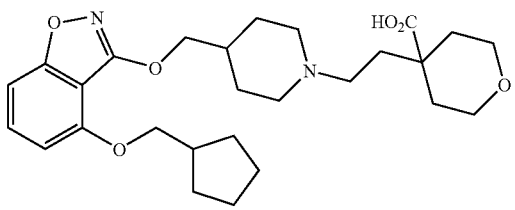 [SMILES: O=C(O)C1(CCN2CCC(COc3noc4cccc(OCC5CCCC5)c34)CC2)CCOCC1]

Step 1

Methyl 4-{2-[4-({[4-(cyclopentylmethoxy)-1,2-benzisoxazol-3-yl]oxy}methyl)piperidin-1-yl]ethyl}-tetrahydro-2H-pyran-4-carboxylate The title compound was prepared according to the procedure described in Step 3 of EXAMPLE 2 using 4-(cyclopentylmethoxy)-3-(piperidin-4-ylmethoxy)-1,2-benzisoxazole (EXAMPLE 22, Step 2) and methyl 4-(2-oxoethyl)tetrahydro-2H-pyran-4-carboxylate (WO 2004/043958) instead of 3-(piperidin-4-ylmethoxy)-4-(2,2,2-trifluoroethoxy)-1,2-benzisoxazole and methyl 1-formylcyclobutanecarboxylate.

$^1$H-NMR (CDCl$_3$) δ: 7.38 (1H, dd, J=7.9, 8.4 Hz), 6.96 (1H, d, J=8.4 Hz), 6.56 (1H, d, J=7.9 Hz), 4.23 (2H, d, J=6.6 Hz), 3.98 (2H, d, J=6.4 Hz), 3.89-3.77 (2H, m), 3.72 (s, 3H), 3.52-3.38 (2H, m), 3.00-2.83 (2H, m), 2.52-1.22 (24H, m).

Step 2

4-{2-[4-({[4-(Cyclopentylmethoxy)-1,2-benzisoxazol-3-yl]oxy}methyl)piperidin-1-yl]ethyl}-tetrahydro-2H-pyran-4-carboxylic acid The title compound was prepared according to the procedure described in Step 6 of EXAMPLE 1 using methyl 4-{2-[4-({[4-(cyclopentylmethoxy)-1,2-benzisoxazol-3-yl]oxy}methyl)piperidin-1-yl]ethyl}-tetrahydro-2H-pyran-4-carboxylate (EXAMPLE 23, Step 1) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

$^1$H-NMR (DMSO-d$_6$) δ: 7.51 (1H, dd, J=8.1, 8.4 Hz), 7.10 (1H, d, J=8.4 Hz), 6.79 (1H, d, J=8.1 Hz), 4.17 (2H, d, J=5.6 Hz), 4.01 (2H, d, J=5.9 Hz), 3.75-3.62 (2H, m), 3.45-3.27 (2H, m), 2.98-2.85 (2H, m), 2.41-2.22 (3H, m), 2.04-1.26 (21H, m).

A signal due to CO$_2$H was not observed.
MS (ESI) m/z: 487 (M+H)$^+$, 485 (M−H)$^−$.
m.p.: 212.5° C.
IR (KBr) ν: 3404, 2951, 1612, 1094 cm$^{−1}$.
Anal. Calcd for C$_{26}$H$_{36}$N$_2$O$_6$: C, 66.64; H, 7.87; N, 5.76. Found: C, 66.67; H, 7.78; N, 5.49.

Example 24

4-{[4-({[4-(Cyclopentyloxy)-1,2-benzisoxazol-3-yl]oxy}methyl)piperidin-1-yl]methyl}tetrahydro-2H-pyran-4-carboxylic acid

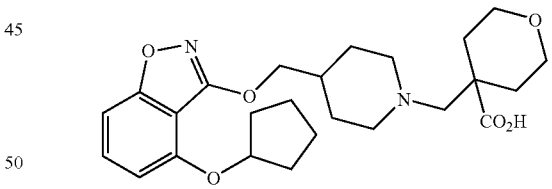

Step 1 tert-Butyl 4-({[4-(cyclopentyloxy)-1,2-benzisoxazol-3-yl]oxy}methyl)piperidine-1-carboxylate The title compound was prepared according to the procedure described in Step 2 of EXAMPLE 7 using tert-butyl 4-{[(4-hydroxy-1,2-benzisoxazol-3-yl)oxy]methyl}piperidine-1-carboxylate (EXAMPLE 17, step 2) and cyclopentanol instead of 4-(benzyloxy)-1,2-benzisoxazol-3-ol and tert-butyl 4-(2-hydroxyethyl)piperidine-1-carboxylate.

$^1$H-NMR (CDCl$_3$) δ: 7.38 (1H, t, J=8.2 Hz), 6.95 (1H, d, J=8.4 Hz), 6.57 (1H, d, J=7.9 Hz), 4.90 (1H, quint, J=3.8 Hz), 4.26 (2H, d, J=6.3 Hz), 4.18 (2H, brm), 2.77 (2H, brt, J=12.0 Hz), 2.10-1.30 (22H, m, including singlet at 1.47 ppm).

Step 2

4-(Cyclopentyloxy)-3-(piperidin-4-ylmethoxy)-1,2-benzisoxazole

The title compound was prepared according to the procedure described in Step 2 of EXAMPLE 2 using tert-Butyl 4-({[4-(cyclopentyloxy)-1,2-benzisoxazol-3-yl]oxy}methyl)piperidine-1-carboxylate (EXAMPLE 24, Step 1) instead of tert-butyl 4-({[4-(2,2,2-trifluoroethoxy)-1,2-benzisoxazol-3-yl]oxy}methyl)piperidine-1-carboxylate.

¹H-NMR (CDCl₃) δ: 7.38 (1H, t, J=8.2 Hz), 6.95 (1H, d, J=8.4 Hz), 6.57 (1H, d, J=7.9 Hz), 4.90 (1H, quint, J=3.9 Hz), 4.25 (2H, d, J=6.8 Hz), 3.67 (1H, br), 3.25 (2H, dt, J=12.5, 3.0 Hz), 2.74 (2H, td, J=12.4, 2.6 Hz), 2.10 (1H, m), 2.00-1.59 (10H, m), 1.44 (2H, qd, J=12.5, 3.9 Hz).

Step 3

Methyl 4-{[4-({[4-(cyclopentyloxy)-1,2-benzisoxazol-3-yl]oxy}methyl)piperidin-1-yl]methyl}tetrahydro-2H-pyran-4-carboxylate The title compound was prepared according to the procedure described in Step 3 of EXAMPLE 2 using 4-(cyclopentyloxy)-3-(piperidin-4-ylmethoxy)-1,2-benzisoxazole (EXAMPLE 24, Step 2) and methyl 4-formyltetrahydro-2H-pyran-4-carboxylate (EXAMPLE 18, Step 1) instead of 3-(piperidin-4-ylmethoxy)-4-(2,2,2-trifluoroethoxy)-1,2-benzisoxazole and methyl 1-formylcyclobutanecarboxylate.

¹H-NMR (CDCl₃) δ: 7.37 (1H, t, J=8.2 Hz), 6.94 (1H, d, J=8.4 Hz), 6.56 (1H, d, J=7.9 Hz), 4.90 (1H, quint, J=3.9 Hz), 4.21 (2H, d, J=6.2 Hz), 3.82 (2H, brd, J=11.5 Hz), 3.71 (3H, s), 3.47 (2H, t, J=11.6 Hz), 2.77 (2H, brd, J=11.4 Hz), 2.52 (2H, s), 2.24 (2H, t, J=11.6 Hz), 2.08 (2H, m), 1.94-1.41 (15H, m).

TLC (silica gel, ethyl acetate/hexane 1:4) Rf: 0.15.

Step 4

4-{[4-({[4-(cyclopentyloxy)-1,2-benzisoxazol-3-yl]oxy}methyl)piperidin-1-yl]methyl}tetrahydro-2H-pyran-4-carboxylic acid The title compound was prepared according to the procedure described in Step 6 of EXAMPLE 1 using methyl 4-{[4-({[4-(cyclopentyloxy)-1,2-benzisoxazol-3-yl]oxy}methyl)piperidin-1-yl]methyl}tetrahydro-2H-pyran-4-carboxylate (EXAMPLE 24, Step 3) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

¹H-NMR (CDCl₃) δ: 7.38 (1H, t, J=8.2 Hz), 6.95 (1H, dd, J=8.4, 0.5 Hz), 6.57 (1H, d, J=7.9 Hz), 4.90 (1H, quint, J=4.0 Hz), 4.28 (2H, d, J=6.3 Hz), 3.93-3.84 (4H, m), 3.15 (2H, brd, J=12.2 Hz), 2.59-2.53 (4H, m), 2.05-1.46 (17H, m).

MS (ESI) m/z: 459 (M+H)⁺, 457 (M−H)⁻.

m.p.: 177.7° C.

IR (KBr) ν: 2950, 1609, 1533, 1433, 1367, 1283, 1088 cm⁻¹.

Anal. Calcd for C₂₅H₃₄N₂O₆·0.5H₂O: C, 64.22; H, 7.55; N, 5.99. Found: C, 64.52; H, 7.50; N, 5.99.

Example 25

4-{2-[4-({[4-(Cyclopentyloxy)-1,2-benzisoxazol-3-yl]oxy}methyl)piperidin-1-yl]ethyl}tetrahydro-2H-Pyran-4-carboxylic acid

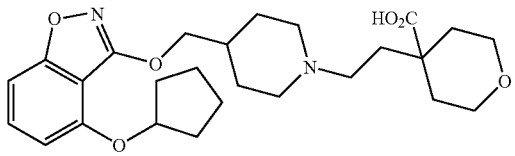 [SMILES: O=C(O)C1(CCN2CCC(COc3noc4cccc(OC5CCCC5)c34)CC2)CCOCC1]

Step 1

Methyl 4-{2-[4-({[4-(cyclopentyloxy)-1,2-benzisoxazol-3-yl]oxy}methyl)piperidin-1-yl]ethyl}-tetrahydro-2H-pyran-4-carboxylate The title compound was prepared according to the procedure described in Step 3 of EXAMPLE 2 using 4-(cyclopentyloxy)-3-(piperidin-4-ylmethoxy)-1,2-benzisoxazole (EXAMPLE 24, Step 2) and methyl 4-(2-oxoethyl)tetrahydro-2H-pyran-4-carboxylate (WO 2004/043958) instead of 3-(piperidin-4-ylmethoxy)-4-(2,2,2-trifluoroethoxy)-1,2-benzisoxazole and methyl 1-formylcyclobutanecarboxylate.

¹H-NMR (CDCl₃) δ 7.37 (1H, dd, J=8.1, 8.4 Hz), 6.95 (1H, d, J=8.4 Hz), 6.56 (1H, d, J=8.1 Hz), 4.96-4.86 (1H, m), 4.22 (2H, d, J=6.6 Hz), 3.89-3.77 (2H, m), 3.72 (s, 3H), 3.53-3.39 (2H, m), 3.00-2.88 (2H, m), 2.34-1.29 (23H, m).

Step 2

4-{2-[4-({[4-(Cyclopentyloxy)-1,2-benzisoxazol-3-yl]oxy}methyl)piperidin-1-yl]ethyl}tetrahydro-2H-pyran-4-carboxylic acid The title compound was prepared according to the procedure described in Step 6 of EXAMPLE 1 using methyl 4-{2-[4-({[4-(cyclopentyloxy)-1,2-benzisoxazol-3-yl]oxy}methyl)piperidin-1-yl]ethyl}-tetrahydro-2H-pyran-4-carboxylate (EXAMPLE 25, Step 1) instead of methyl 4-{[4-({[4-(2,2,2-rifluoroethoxy)-1,2-benzisoxazol-3-yl]oxy}methyl)piperidin-1-yl]methyl}tetrahydro-2H-pyran-4-carboxylate.

¹H-NMR (DMSO-d₆) δ: 7.50 (1H, dd, J=8.1, 8.4 Hz), 7.07 (1H, d, J=8.4 Hz), 6.78 (1H, d, J=8.1 Hz), 5.04-4.95 (1H, m), 4.17 (2H, d, J=6.1 Hz), 3.75-3.63 (2H, m), 3.45-3.27 (2H, m), 2.98-2.87 (2H, m), 2.36-2.24 (2H, m), 2.06-1.25 (21H, m).

A signal due to CO₂H was not observed.

MS (ESI) m/z: 473 (M+H)⁺, 471 (M−H)⁻.

IR (KBr) ν: 3422, 2942, 1610, 1084 cm⁻¹.

Example 26

4-{[4-({[4-(Tetrahydro-2H-pyran-4-yloxy)-1,2-benzisoxazol-3-yl]oxy}methyl)piperidin-1-yl]methyl}-tetrahydro-2H-pyran-4-ol

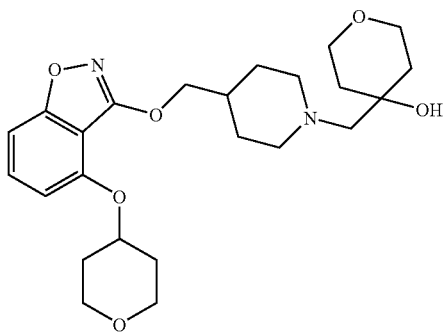 [SMILES: OC1(CN2CCC(COc3noc4cccc(OC5CCOCC5)c34)CC2)CCOCC1]

Step 1 tert-Butyl 4-({[4-(tetrahydro-2H-pyran-4-yloxy)-1,2-benzisoxazol-3-yl]oxy}methyl)piperidine-1-carboxylate The title compound was prepared according to the procedure described in Step 2 of EXAMPLE 7 using tert-butyl 4-{[(4-hydroxy-1,2-benzisoxazol-3-yl)oxy]methyl}piperidine-1-carboxylate (EXAMPLE 17, step 2) and tetrahydro-2H-pyran-4-ol instead of 4-(benzyloxy)-1,2-benzisoxazol-3-ol and tert-butyl 4-(2-hydroxyethyl)piperidine-1-carboxylate.

$^1$H-NMR (CDCl3) δ: 7.39 (1H, t, J=8.4 Hz), 7.00 (1H, d, J=8.4 Hz), 6.61 (1H, d, J=8.4 Hz), 4.76-4.62 (1H, m), 4.28 (2H, d, J=6.2 Hz), 4.25-3.85 (3H, m), 3.71-3.54 (2H, m), 2.90-2.60 (2H, m), 2.20-1.94 (4H, m), 1.93-1.75 (4H, m), 1.47 (9H, s), 1.45-1.25 (2H, m).

Step 2

3-(Piperidin-4-ylmethoxy)-4-(tetrahydro-2H-pyran-4-yloxy)-1,2-benzisoxazole hydrochloride The title compound was prepared according to the procedure described in Step 4 of EXAMPLE 8 using tert-butyl 4-({[4-(tetrahydro-2H-pyran-4-yloxy)-1,2-benzisoxazol-3-yl]oxy}methyl)piperidine-1-carboxylate (EXAMPLE 26, Step 1) instead of tert-butyl 4-{[(4-isobutyoxy-1,2-benzisoxazol-3-yl)-oxy]methyl}piperidine-1-carboxylate.

$^1$H-NMR (CDCl3) δ: 7.40 (1H, t, J=8.4 Hz), 7.00 (1H, d, J=8.4 Hz), 6.62 (1H, d, J=8.4 Hz), 4.76-4.65 (1H, m), 4.34 (2H, d, J=6.9 Hz) 4.05-3.91 (2H, m), 3.71-3.50 (4H, m), 3.05-2.85 (2H, m), 2.37-1.99 (5H, m), 1.95-1.75 (4H, m).

Signals due to N$\underline{H}$ and $\underline{H}$Cl were not observed.
MS (ESI) m/z: 333 (M−Cl)$^+$.

Step 3

4-{[4-({[4-(Tetrahydro-2H-pyran-4-yloxy)-1,2-benzisoxazol-3-yl]oxy}methyl)piperidin-1-yl]methyl}-tetrahydro-2H-pyran-4-ol The title compound was prepared according to the procedure described in Step 5 of EXAMPLE 8 using 3-(piperidin-4-ylmethoxy)-4-(tetrahydro-2H-pyran-4-ylmethoxy)-4-(tetrahydro-2H-pyran-4-yloxy)-1,2-benzisoxazole hydrochloride (EXAMPLE 26, Step 2) instead of 4-{[(isobutoxy-1,2-benzisoxazol-3-yl)oxy]methyl}piperidinium chloride.

$^1$H-NMR (CDCl$_3$) δ: 7.39 (1H, t, J=8.2 Hz), 7.00 (1H, d, J=8.2 Hz), 6.62 (1H, d, J=8.2 Hz), 4.79-4.68 (1H, m), 4.28 (2H, d, J=5.9 Hz), 4.08-3.96 (2H, m), 3.88-3.73 (4H, m), 3.71-3.60 (2H, m), 3.01-2.88 (2H, m), 2.42 (2H, dt, J=11.7, 2.1 Hz), 2.35 (2H, s), 2.14-1.98 (2H, m), 1.96-1.75 (5H, m), 1.72-1.41 (7H, m).

MS (ESI) m/z: 447 (M+H)$^+$.
IR (KBr) ν: 3445, 2943, 1611, 1535, 1433, 1286, 1088, 984, 783 cm$^{-1}$
Anal. Calcd for $C_{24}H_{34}N_2O_6 \cdot 0.2H_2O$: C, 64.04; H, 7.70; N, 6.22. Found: C, 63.71; H, 7.30; N, 6.13.
m.p.: 107.4° C.

Example 27

4-{[4-({[4-(Tetrahydro-2H-pyran-4-yloxy)-1,2-benzisoxazol-3-yl]oxy}methyl)piperidin-1-yl]methyl}-tetrahydro-2H-pyran-4-carboxylic acid

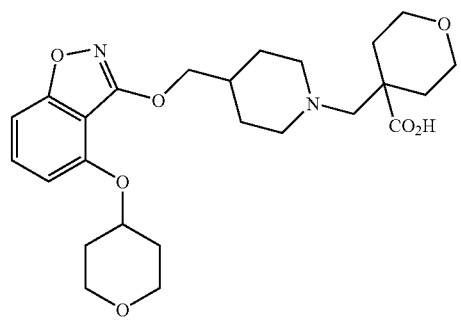 [SMILES: O=C(O)C1(CN2CCC(COc3noc4cccc(OC5CCOCC5)c34)CC2)CCOCC1]

Step 1

3-(Piperidin-4-ylmethoxy)-4-(tetrahydro-2H-pyran-4-yloxy)-1,2-benzisoxazole

The title compound was prepared according to the procedure described in Step 2 of EXAMPLE 2 using tert-butyl 4-({[4-(tetrahydro-2H-pyran-4-yloxy)-1,2-benzisoxazol-3-yl]oxy}methyl)piperidine-1-carboxylate (EXAMPLE 26, Step 1) instead of tert-butyl 4-({[4-(2,2,2-trifluoroethoxy)-1,2-benzisoxazol-3-yl]oxy}methyl)piperidine-1-carboxylate.

$^1$H-NMR (CDCl$_3$) δ: 7.42-7.36 (1H, m), 7.00 (1H, d, J=8.4 Hz), 6.62 (1H, d, J=7.9 Hz), 4.75-4.69 (1H, m), 4.26 (2H, d, J=6.8 Hz), 4.05-3.98 (2H, m), 3.69-3.62 (2H, m), 3.18-3.12 (2H, m), 2.68 (2H, dt, J=12.1, 2.8 Hz), 2.10-2.01 (3H, m), 1.93-1.84 (4H, m), 1.39-1.25 (2H, m).

A signal due to N$\underline{H}$ was not observed.
TLC (silica gel, ethyl acetate/hexane 1:1) Rf: 0.1.

Step 2

Methyl 4-{[4-({[4-(tetrahydro-2H-pyran-4-yloxy)-1,2-benzisoxazol-3-yl]oxy}methyl)piperidin-1-yl]methyl}tetrahydro-2H-pyran-4-carboxylate The title compound was prepared according to the procedure described in Step 3 of EXAMPLE 2 using 3-(piperidin-4-ylmethoxy)-4-(tetrahydro-2H-pyran-4-yloxy)-1,2-benzisoxazole (EXAMPLE 27, Step 1) and methyl 4-formyltetrahydro-2H-pyran-4-carboxylate (EXAMPLE 18, Step 1) instead of 3-(piperidin-4-ylmethoxy)-4-(2,2,2-trifluoroethoxy)-1,2-benzisoxazole and methyl 1-formylcyclobutanecarboxylate.

$^1$H-NMR (CDCl$_3$) δ: 7.41-7.36 (1H, m), 6.99 (1H, d, J=8.4 Hz), 6.62 (1H, d, J=8.1 Hz), 4.75-4.68 (1H, m), 4.24 (2H, d, J=6.2 Hz), 4.04-3.96 (2H, m), 3.87-3.78 (3H, m), 3.72 (3H, s), 3.69-3.61 (3H, m), 3.58-3.42 (3H, m), 2.79-2.76 (2H, m), 2.52 (2H, s), 2.29-1.36 (12H, m).

TLC (silica gel, ethyl acetate/hexane 1:1) Rf: 0.45.

Step 3

4-{[4-({[4-(Tetrahydro-2H-pyran-4-yloxy)-1,2-benzisoxazol-3-yl]oxy}methyl)piperidin-1-yl]methyl}tetrahydro-2H-pyran-4-carboxylic acid The title compound was prepared according to the procedure described in Step 6 of EXAMPLE 1 using methyl 4-{[4-({[4-(tetrahydro-2H-pyran-4-yloxy)-1,2-benzisoxazol-3-yl]oxy}methyl)piperidin-1-yl]-methyl}tetrahydro-2H-pyran-4-carboxylate (EXAMPLE 27, Step 2) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

$^1$H-NMR (CDCl$_3$) δ: 7.43-7.37 (1H, m), 7.01 (1H, d, J=8.4 Hz), 6.63 (1H, d, J=8.1 Hz), 4.76-4.68 (1H, m), 4.31 (2H, d, J=6.3 Hz), 4.05-3.96 (2H, m), 3.91-3.78 (4H, m), 3.70-3.62 (2H, m), 3.18-3.14 (2H, m), 2.59 (2H, s), 2.58-2.51 (2H, m), 2.12-1.81 (9H, m), 1.71-1.46 (4H, m).

A signal due to CO$_2$H was not observed.

TLC (silica gel, dichloromethane/methanol/25% ammonium hydroxide 10:1:0.2) Rf: 0.25.

MS (ESI) m/z: 475 (M+H)$^+$, 473 (M−H)$^-$.

Anal. Calcd for C$_{25}$H$_{34}$N$_2$O$_7$·1.0H$_2$O: C, 60.96; H, 7.37; N, 5.69. Found: C, 61.19; H, 7.24; N, 5.62.

Example 28

1-{[4-({[4-(Tetrahydro-2H-pyran-4-yloxy)-1,2-benzisoxazol-3-yl]oxy}methyl)piperidin-1-yl]methyl}-cyclopentanecarboxylic acid

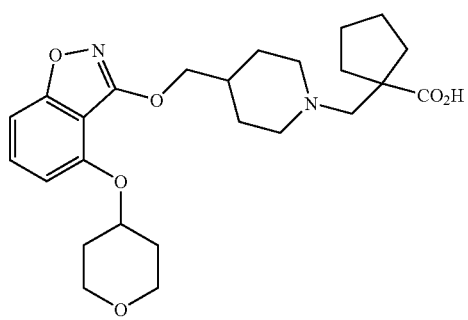 [SMILES: O=C(O)C1(CN2CCC(COc3noc4cccc(OC5CCOCC5)c34)CC2)CCCC1]

Step 1

Methyl 1-{[4-({[4-(tetrahydro-2H-pyran-4-yloxy)-1,2-benzisoxazol-3-yl]oxy}methyl)piperidin-1-yl]-methyl}cyclopentanecarboxylate The title compound was prepared according to the procedure described in Step 3 of EXAMPLE 2 using 3-(piperidin-4-ylmethoxy)-4-(tetrahydro-2H-pyran-4-yloxy)-1,2-benzisoxazole (EXAMPLE 27, Step 1) and methyl 1-formylcyclopentanecarboxylate (*Synthesis*, 1997, 32) instead of 3-(piperidin-4-ylmethoxy)-4-(2,2,2-trifluoroethoxy)-1,2-benzisoxazole and methyl 1-formylcyclobutanecarboxylate.

$^1$H-NMR (CDCl$_3$): 7.38 (1H, dd, J=8.1, 8.4 Hz), 6.99 (1H, d, J=8.4 Hz), 6.61 (1H, d, J=8.1 Hz), 4.76-4.67 (1H, m), 4.23 (2H, d, J=6.4 Hz), 4.06-3.95 (2H, m), 3.70-3.60 (5H, m), 2.89-2.77 (2H, m), 2.59 (2H, s), 2.20-1.30 (19H, m).

Step 2

1-{[4-({[4-(Tetrahydro-2H-pyran-4-yloxy)-1,2-benzisoxazol-3-yl]oxy}methyl)piperidin-1-yl]methyl}cyclopentanecarboxylic acid The title compound was prepared according to the procedure described in Step 6 of EXAMPLE 1 using methyl 1-{[4-({[4-(tetrahydro-2H-pyran-4-yloxy)-1,2-benzisoxazol-3-yl]oxy}methyl)piperidin-1-yl]methyl}cyclopentanecarboxylate (EXAMPLE 28, Step 1) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

$^1$H-NMR (DMSO-d$_6$): 7.51 (1H, t, J=8.2 Hz), 7.10 (1H, d, J=8.2 Hz), 6.90 (1H, d, J=8.2 Hz), 4.87-4.76 (1H, m), 4.20 (2H, d, J=5.7 Hz), 3.90-3.70 (2H, m), 3.60-3.49 (2H, m), 2.98-2.85 (2H, m), 2.59 (2H, s), 2.27-2.13 (2H, m), 2.05-1.30 (17H, m).

A signal due to CO$_2$H was not observed.

MS (ESI) m/z: 459 (M+H)$^+$, 457 (M−H)$^-$.

m.p.: 172.9° C.

IR (KBr) ν: 3414, 2932, 1612 cm$^{-1}$.

Anal. Calcd for C$_{25}$H$_{34}$N$_2$O$_6$·0.1H$_2$O: C, 65.23; H, 7.49; N, 6.09. Found: C, 64.83; H, 7.44; N, 5.93.

Example 29 trans-4-{[4-({[4-(Tetrahydro-2H-pyran-4-yloxy)-1,2-benzisoxazol-3-yl]oxy}methyl)piperidin-1-yl]methyl}cyclohexanecarboxylic acid

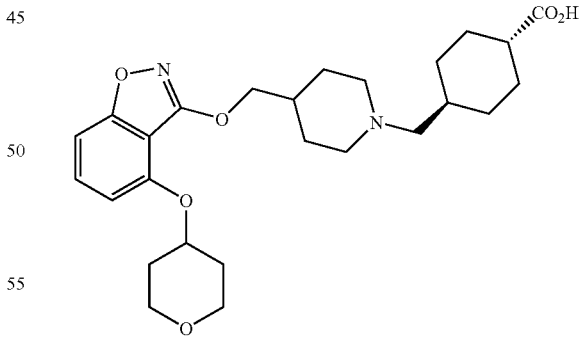

Step 1

Methyl trans-4-{[4-({[4-(tetrahydro-2H-pyran-4-yloxy)-1,2-benzisoxazol-3-yl]oxy}methyl)piperidin-1-yl]methyl}cyclohexanecarboxylate The title compound was prepared according to the procedure described in Step 3 of EXAMPLE 2 using 3-(piperidin- 4-ylmethoxy)-4-(tetrahydro-2H-pyran-4-yloxy)-1,2-benzisoxazole (EXAMPLE 27, Step 1) and methyl trans-4-formylcyclohexanecarboxylate (JP 49-48639) instead of 3-(piperidin-4-ylmethoxy)-4-(2,2,2-trifluoroethoxy)-1,2-benzisoxazole and methyl 1-formylcyclobutanecarboxylate.

$^1$H-NMR (CDCl$_3$) δ: 7.39 (1H, dd, J=8.1, 8.4 Hz), 7.00 (1H, d, J=8.4 Hz), 6.61 (1H, d, J=8.1 Hz), 4.77-4.68 (1H, m), 4.26 (2H, d, J=6.4 Hz), 4.06-3.95 (2H, m), 3.73-3.59 (5H, m), 2.96-2.83 (2H, m), 2.33-0.80 (23H, m).

Step 2 trans-4-{[4-({[4-(Tetrahydro-2H-pyran-4-yloxy)-1,2-benzisoxazol-3-yl]oxy}methyl)piperidin-1-yl]methyl}cyclohexanecarboxylic acid The title compound was prepared according to the procedure described in Step 6 of EXAMPLE 1 using methyl trans-4-{[4-({[4-(tetrahydro-2H-pyran-4-yloxy)-1,2-benzisoxazol-3-yl]oxy}methyl)piperidin-1-yl]methyl}cyclohexanecarboxylate (EXAMPLE 29, Step 1) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

$^1$H-NMR (DMSO-d$_6$) δ: 7.51 (1H, dd, J=8.1, 8.4 Hz), 7.11 (1H, d, J=8.4 Hz), 6.89 (1H, d, J=8.1 Hz), 4.87-4.77 (1H, m), 4.20 (2H, d, J=5.5 Hz), 3.90-3.78 (2H, m), 3.60-3.49 (2H, m), 2.90-2.79 (2H, m), 2.18-1.19 (21H, m), 0.93-0.75 (2H, m).

A signal due to CO$_2$H was not observed.
MS (ESI) m/z: 473 (M+H)$^+$, 471 (M−H)$^-$.
m.p.: 154.6° C.
IR (KBr) ν: 3414, 2932, 1612 cm$^{-1}$.
Anal. Calcd for C$_{26}$H$_{36}$N$_2$O$_6$.1.5H$_2$O: C, 62.51; H, 7.87; N, 5.61. Found: C, 62.60; H, 8.02; N, 5.37.

Example 30

1-{[4-({[4-(Tetrahydro-2H-pyran-4-yloxy)-1,2-benzisoxazol-3-yl]oxy}methyl)piperidin-1-yl]methyl}-cyclohexanecarboxylic acid

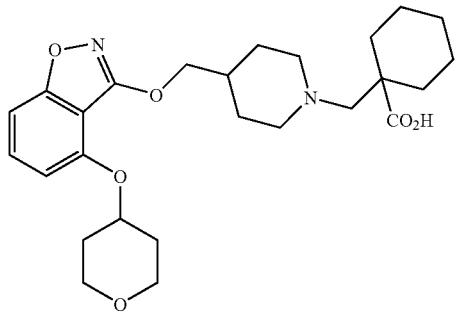

Step 1

3-{[1-(Ethoxymethyl)piperidin-4-yl]methoxy}-4-(tetrahydro-2H-pyran-4-yloxy)-1,2-benzisoxazole The title compound was prepared according to the procedure described in Step 4 of EXAMPLE 7 using 3-(piperidin-4-ylmethoxy)-4-(tetrahydro-2H-pyran-4-yloxy)-1,2-benzisoxazole (EXAMPLE 27, Step 1) instead of 4-(benzyloxy)-3-(2-piperidin-4-ylethoxy)-1,2-benzisoxazole.

$^1$H-NMR (CDCl$_3$) δ: 7.39 (1H, dd, J=7.9, 8.4 Hz), 6.99 (1H, d, J=8.4 Hz), 6.61 (1H, d, J=7.9 Hz), 4.76-4.67 (1H, m), 4.27 (2H, d, J=6.3 Hz), 4.11 (2H, s), 4.07-3.93 (2H, m), 3.75-3.45 (4H, m), 3.07-2.90 (2H, m), 2.61-2.44 (2H, m), 2.13-1.78 (7H, m), 1.52-1.14 (5H, m).

Step 2

Methyl 1-{[4-({[4-(tetrahydro-2H-pyran-4-yloxy)-1,2-benzisoxazol-3-yl]oxy}methyl)piperidin-1-yl]methyl}cyclohexanecarboxylate The title compound was prepared according to the procedure described in Step 5 of EXAMPLE 7 using 3-{[1-(ethoxymethyl)piperidin-4-yl]methoxy}-4-(tetrahydro-2H-pyran-4-yloxy)-1,2-benzisoxazole (EXAMPLE 30, Step 1) and [cyclohexylidene(methoxy)methoxy](trimethyl)silane (*Tetrahedron* 2004, 60, 8957-8966) instead of 4-(benzyloxy)-3-{2-[1-(ethoxymethyl)piperidin-4-yl]ethoxy}-1,2-benzisoxazole and [methoxy(tetrahydro-4H-pyran-4-ylidene)methoxy](trimethyl)silane.

$^1$H-NMR (CDCl$_3$) δ: 7.38 (1H, dd, J=7.9, 8.4 Hz), 6.99 (1H, d, J=8.4 Hz), 6.61 (1H, d, J=7.9 Hz), 4.77-4.66 (1H, m), 4.24 (2H, d, J=6.4 Hz), 4.07-3.95 (2H, m), 3.70-3.60 (5H, m), 2.84-2.72 (2H, m), 2.47 (2H, s), 2.29-1.18 (21H, m).

Step 3

1-{[4-({[4-(Tetrahydro-2H-pyran-4-yloxy)-1,2-benzisoxazol-3-yl]oxy}methyl)piperidin-1-yl]methyl}cyclohexanecarboxylic acid The title compound was prepared according to the procedure described in Step 6 of EXAMPLE 1 using methyl 1-{[4-({[4-(tetrahydro-2H-pyran-4-yloxy)-1,2-benzisoxazol-3-yl]oxy}methyl)piperidin-1-yl]methyl}cyclohexanecarboxylate (EXAMPLE 30, Step 2) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

$^1$H-NMR (DMSO-d$_6$) δ: 7.51 (1H, dd, J=8.1, 8.4 Hz), 7.11 (1H, d, J=8.4 Hz), 6.90 (1H, d, J=8.1 Hz), 4.87-4.77 (1H, m), 4.19 (2H, d, J=5.7 Hz), 3.91-3.79 (2H, m), 3.61-3.49 (2H, m), 2.89-2.77 (2H, m), 2.45 (2H, s), 2.26-2.12 (2H, m), 2.05-1.14 (19H, m).

A signal due to CO$_2$H was not observed.
MS (ESI) m/z: 473 (M+H)$^+$, 471 (M−H)$^-$.
m.p.: 157.1° C.
IR (KBr) ν: 3429, 2926, 1611, 1528 cm$^{-1}$.
Anal. Calcd for C$_{26}$H$_{36}$N$_2$O$_6$.0.5H$_2$O: C, 64.84; H, 7.74; N, 5.82. Found: C, 64.86; H, 7.77; N, 5.69.

Example 31

4-({4-[{(4-[(1-Hydroxycyclopentyl)methoxy]-1,2-benzisoxazol-3-yl}oxy)methyl]piperidin-1-yl}-methyl)tetrahydro-2H-pyran-4-ol

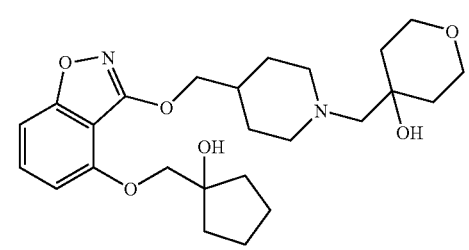 [SMILES: OC1(COc2cccc3onc(OCC4CCN(CC5(O)CCOCC5)CC4)c23)CCCC1]

Step 1 tert-Butyl 4-[({4-[(1-hydroxycyclopentyl)methoxy]-1,2-benzisoxazol-3-yl]oxy)methyl}piperidine-1-carboxylate A mixture of tert-butyl 4-{[(4-hydroxy-1,2-benzisoxazol-3-yl)oxy]methyl}piperidine-1-carboxylate (100 mg, 0.287 mmol, EXAMPLE 17, step 2), 1-oxaspiro[2.4]heptane (59.7 mg, 0.609 mmol), and potassium carbonate (156 mg, 1.13 mmol) in ethanol (2 mL) was heated at 80° C. for 5 h. After cooling to room temperature, the mixture was diluted with ethyl acetate (3 mL) and 5% aq. sodium chloride was added to the mixture. Organic layer was separated, washed with brine, dried over magnesium sulfate and concentrated in vacuo to give a solid. The residual solid was purified by NH gel column chromatography (ethyl acetate/hexane 1:2) to give 95 mg (74%) of the title compound as a white solid.

$^1$H-NMR (CDCl$_3$) δ: 7.41 (1H, t, J=8.2 Hz), 7.02 (1H, d, 8.6 Hz), 6.60 (1H, d, J=7.9 Hz), 4.27 (2H, d, J=6.6 Hz), 4.16 (2H, brm), 4.05 (2H, s), 2.76 (2H, brt, J=12.5 Hz), 2.36 (1H, s), 2.05 (1H, m), 1.91-1.61 (10H, m), 1.51-1.25 (11H, m, including singlet at 1.47 ppm). TLC(NH gel, ethyl acetate/hexane=1:1) Rf: 0.55.

Step 2

1-({[3-(Piperidin-4-ylmethoxy)-1,2-benzisoxazol-4-yl]oxy}methyl)cyclopentanol hydrochloride The title compound was prepared according to the procedure described in Step 4 of EXAMPLE 8 using tert-butyl 4-[({4-[(1-Hydroxycyclopentyl)methoxy]-1,2-benzisoxazol-3-yl}oxy)methyl]piperidine-1-carboxylate (EXAMPLE 31, Step 1) instead of tert-butyl 4-{[(4-isobutyoxy-1,2-benzisoxazol-3-yl)-oxy]methyl}piperidine-1-carboxylate.

$^1$H-NMR (DMSO-d$_6$) δ: 9.08 (1H, br), 8.70 (1H, br), 7.53 (1H, t, J=8.2 Hz), 7.12 (1H, d, J=8.4 Hz), 6.82 (1H, d, J=7.9 Hz), 4.65 (1H, br), 4.22 (2H, d, J=6.8 Hz), 4.00 (2H, s), 3.31 (2H, m), 2.90 (2H, m), 2.16 (1H, m), 2.00-1.48 (12H, m).

MS (ESI) m/z: 347 (M−Cl)$^+$.

m.p.: 210.8° C.

IR (KBr) ν: 3406, 2953, 1612, 1537, 1431, 1366, 1097 cm$^-$.

Anal. Calcd for C$_{19}$H$_{26}$N$_2$O$_4$·0.1H$_2$O: C, 59.32; H, 7.13; N, 7.28. Found: C, 59.18; H, 7.24; N, 7.22.

Step 3

4-({4-[({4-[(1-Hydroxycyclopentyl)methoxy]-1,2-benzisoxazol-3-yl}oxy)methyl}piperidin-1-yl}methyl)tetrahydro-2H-pyran-4-ol The title compound was prepared according to the procedure described in Step 5 of EXAMPLE 8 using 1-({[3-(piperidin-4-ylmethoxy)-1,2-benzisoxazol-4-yl]oxy}methyl)cyclopentanol hydrochloride (EXAMPLE 31, Step 2) instead of 4-{[(isobutoxy-1,2-benzisoxazol-3-yl)oxy]methyl}piperidinium chloride.

$^1$H-NMR (CDCl$_3$) δ: 7.41 (1H, t, J=8.1 Hz), 7.02 (1H, d, J=8.6 Hz), 6.59 (1H, d, J=7.9 Hz), 4.29 (2H, d, J=5.1 Hz), 4.04 (2H, s), 3.85-3.76 (4H, m), 2.94 (2H, brd, J=11.5 Hz), 2.62 (1H, brs), 2.39 (2H, m), 2.33 (2H, s), 1.92-1.47 (17H, m).

MS (ESI) m/z: 461 (M+H)$^+$.

m.p.: 136.5° C.

IR (KBr) δ: 3456, 3406, 2949, 1612, 1531, 1433, 1103 cm$^{-1}$.

Anal. Calcd for C$_{25}$H$_{36}$N$_2$O$_6$: C, 65.20; H, 7.88; N, 6.08. Found: C, 64.97; H, 7.71; N, 5.79.

Example 32

4-({4-[({4-[(trans-2-Hydroxycyclopentyl)oxy]-1,2-benzisoxazol-3-yl}oxy)methyl]piperidin-1-yl}-methyl)tetrahydro-2H-pyran-4-ol

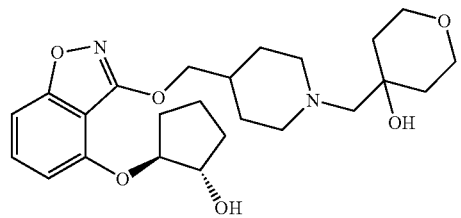 [SMILES: O[C@H]1CCC[C@@H]1Oc1cccc2onc(OCC3CCN(CC4(O)CCOCC4)CC3)c12]

Step 1 tert-Butyl 4-[({4-[(trans-2-hydroxycyclopentyl)oxy]-1,2-benzisoxazole-3-yl}oxy)methyl]-piperidine-1-carboxylate The title compound was prepared according to the procedure described in Step 1 of EXAMPLE 31 using cyclopenten oxide instead of 1-oxaspiro[2.4]heptane.

$^1$H-NMR (CDCl$_3$) δ: 7.39 (1H, t, J=8.2 Hz), 6.98 (1H, d, J=8.4 Hz), 6.66 (1H, d, J=8.0 Hz), 4.66 (1H, m), 4.37 (1H, m), 4.26 (2H, d, J=6.1 Hz), 4.16 (2H, br), 2.77 (2H, brt, J=12.8 Hz), 2.23-2.07 (2H, m), 1.85-1.62 (7H, m), 1.47 (9H, s), 1.41 (2H, m).

TLC (NH gel, ethyl acetate/hexane=1:1) Rf: 0.63.

Step 2 trans-2-{[3-(Piperidin-4-ylmethoxy)-1,2-benzisoxazol-4-yl]oxy}cyclopentanol hydrochloride The title compound was prepared according to the procedure described in Step 4 of EXAMPLE 8 using tert-butyl 4-[({4-[(trans-2-hydroxycyclopentyl)oxy]-1,2-benzisoxazole-3-yl}oxy)methyl]piperidine-1-carboxylate (EXAMPLE 32, Step 1) instead of tert-butyl 4-{[(4-isobutyoxy-1,2-benzisoxazol-3-yl)oxy]-methyl}piperidine-1-carboxylate.

$^1$H-NMR (DMSO-d$_6$) δ: 7.53 (1H, t, J=8.2 Hz), 7.11 (1H, d, J=8.4 Hz), 6.89 (1H, d, J=8.0 Hz), 5.07 (1H, m), 4.64 (1H, m), 4.23 (2H, d, J=6.8 Hz), 4.11 (1H, br), 3.3 (overlapped with water), 2.92 (2H, brt, J=11.7 Hz), 2.15 (2H, m), 1.96-1.48 (9H, m).

MS (ESI) m/z: 333 (M—Cl)$^+$.

IR (KBr) ν: 3410, 2937, 1611, 1533, 1433, 1097 cm$^{-1}$.

Step 3

4-({4-[({4-[(trans-2-Hydroxycyclopentyl)oxy]-1,2-benzisoxazol-3-yl}oxy)methyl]-piperidin-1-yl}methyl)tetrahydro-2H-pyran-4-ol The title compound was prepared according to the procedure described in Step 5 of EXAMPLE 8 using trans-2-{[3-

(piperidin-4-ylmethoxy)-1,2-benzisoxazol-4-yl]oxy}cyclopentanol hydrochloride (EXAMPLE 32, Step 2) instead of 4-{[(isobutoxy-1,2-benzisoxazol-3-yl)oxy]methyl}piperidinium chloride.

$^1$H-NMR (CDCl$_3$) δ: 7.39 (1H, t, J=8.2 Hz), 6.99 (1H, d, J=8.4 Hz), 6.64 (1H, d, J=7.9 Hz), 4.66 (1H, m), 4.41 (1H, m), 4.31 (1H, dd, J=9.9, 4.6 Hz), 4.25 (1H, dd, J=10.1, 5.0 Hz), 3.81 (5H, m), 2.94 (2H, m), 2.40 (2H, m), 2.36 (2H, s), 2.22-2.05 (3H, m), 1.87-1.45 (12H, m).

MS (ESI) m/z: 447 (M+H)$^+$.

IR (KBr) ν: 3379, 2937, 1614, 1533, 1431, 1099 cm$^{-1}$.

Anal. Calcd for C$_{24}$H$_{34}$N$_2$O$_6$: C, 64.55; H, 7.67; N, 6.27. Found: C, 64.85; H, 7.76; N, 5.98.

Example 33

1-({4-[({4-[(trans-2-Hydroxycyclopentyl)oxy]-1,2-benzisoxazol-3-yl}oxy)methyl]piperidin-1-yl}methyl)cyclopentanecarboxylic acid

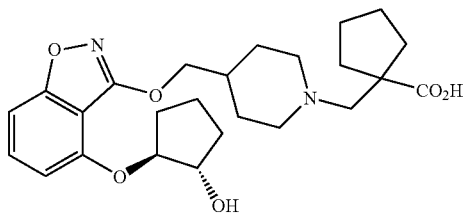 [SMILES: O=C(O)C1(CN2CCC(COc3noc4cccc(O[C@H]5CCC[C@@H]5O)c34)CC2)CCCC1]

Step 1

Methyl 1-(iodomethyl)cyclopentanecarboxylate

To a stirred solution of N,N-diisopropylamine (1.31 mL, 9.36 mmol) in tetrahydrofuran (5 mL) was added n-butyllithium (1.58 M in hexane, 5.43 mL, 8.58 mmol) at −10° C. under nitrogen. After being stirred at −10° C. for 1 h, a solution of methyl cyclopentanecarboxylate (1.00 g, 7.80 mmol) in tetrahydrofuran (3 mL) was added dropwise to the mixture, and the mixture was stirred at 0° C. for 2 h. Diiodomethane (0.628 mL, 7.80 mmol) was added to the mixture and the mixture was warmed to room temperature. After being stirred for 16 h, the mixture was quenched with aq. ammonium chloride (50 mL). The mixture was extracted with diethylether (75 mL×2) and washed with brine (75 mL). The organic layer was combined and dried over sodium sulfate and concentrated in vacuo to give an oil. The residual oil was purified by silica gel column chromatography (hexane/ethyl acetate 20:1 to 10:1) to give 1.085 g (52%) of the title compound as a colorless oil.

$^1$H-NMR (CDCl$_3$) δ: 3.73 (3H, s), 3.42 (2H, s), 2.30-2.15 (2H, m), 1.80-1.55 (6H, m).

Step 2 trans-2-{[3-(Piperidin-4-ylmethoxy)-1,2-benzisoxazol-4-yl]oxy}cyclopentanol

The title compound was prepared according to the procedure described in Step 2 of EXAMPLE 2 using tert-butyl 4-{[(4-{[trans-2-hydroxycyclopentyl]oxy}-1,2-benzisoxazol-3-yl)oxy]methyl}piperidine-1-carboxylate (EXAMPLE 32, Step 1) instead of tert-butyl 4-({[4-(2,2,2-trifluoroethoxy)-1,2-benzisoxazol-3-yl]oxy}-methyl)piperidine-1-carboxylate.

$^1$H-NMR (CDCl$_3$) δ: 7.39 (1H, t, J=8.4 Hz), 7.00 (1H, d, J=8.4 Hz), 6.62 (1H, J=7.9 Hz), 4.64 (1H, m), 4.46-4.39 (1H, m), 4.37 (1H, dd, J=10.1, 4.6 Hz), 4.29 (2H, dd, J=10.1, 4.6 Hz), 3.25-3.05 (2H, m), 2.72-2.60 (2H, m), 2.50-1.50 (13H, m).

MS (ESI) m/z: 333 (M+H)$^+$.

Step 3

Methyl 1-({4-[({4-[(trans-2-Hydroxycyclopentyl)oxy]-1,2-benzisoxazol-3-yl}oxy)methyl]piperidin-1-yl}methyl)cyclopentanecarboxylate A mixture of trans-2-{[3-(piperidin-4-ylmethoxy)-1,2-benzisoxazol-4-yl]oxy}cyclopentanol (77 mg, 0.23 mmol, EXAMPLE 33, Step 2), methyl 1-(iodomethyl)cyclopentanecarboxylate (75 mg, 0.28 mmol, EXAMPLE 33, Step 1), and N,N-diisopropylethylamine (0.12 mL, 0.70 mmol) in N-methylpyrrolidone (3.0 mL) was heated at 120° C. for 14 h. The mixture was cooled to room temperature and the mixture was diluted with ethyl acetate and water. The mixture was extracted with ethyl acetate (30 mL×2) and washed with brine. The extracts were combined and dried over sodium sulfate and concentrated in vacuo to give a brown solid. The residual solid was purified by silica gel column chromatography (hexane/ethyl acetate 3:2) to give 12 mg (11%) of the title compound as a colorless viscous oil.

$^1$H-NMR (CDCl$_3$) δ: 7.38 (1H, t, J=8.4 Hz), 6.97 (1H, d, J=8.4 Hz), 6.63 (1H, J=8.1 Hz), 4.66 (1H, m), 4.41 (1H, m), 4.24 (2H, m), 3.68 (3H, s), 2.84 (2H, br), 2.59 (2H, qAB, J=13.4 Hz), 2.25-2.20 (7H, m), 1.85 (4H, m), 1.75-1.45 (11H, m).

MS (ESI) m/z: 473 (M+H)$^+$.

Step 4

1-({4-[({4-[(trans-2-Hydroxycyclopentyl)oxy]-1,2-benzisoxazol-3-yl}oxy)methyl]piperidin-1-yl}-methyl)cyclopentanecarboxylic acid The title compound was prepared according to the procedure described in Step 6 of EXAMPLE 1 using methyl 1-({4-[({4-[(trans-2-Hydroxycyclopentyl)oxy]-1,2-benzisoxazol-3-yl}oxy)methyl]piperidin-1-yl}methyl)cyclopentanecarboxylate (EXAMPLE 33, Step 3) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

$^1$H-NMR (DMSO-d$_6$) δ: 7.52 (1H, t, J=8.9 Hz), 7.28 (1H, br), 7.10 (1H, d, J=8.2 Hz), 6.88 (1H, d, J=8.1 Hz), 4.65 (1H, br), 4.18 (2H, br), 4.11 (1H, br), 3.07 (2H, br), 2.79 (2H, br), 2.46 (2H, br), 2.20-1.40 (11H, m).

MS (ESI) m/z: 459 (M+H)$^+$, 457 (M−H)$^-$.

Example 34

1-({4-[({4-[(trans-2-Hydroxycyclopentyl)oxy]-1,2-benzisoxazol-3-yl}oxy)methyl]piperidin-1-yl}-methyl)cyclobutanecarboxylic acid

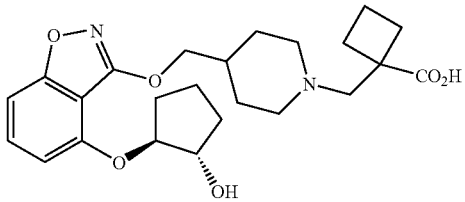 [SMILES: O=C(O)C1(CN2CCC(COc3noc4cccc(O[C@H]5CCC[C@@H]5O)c34)CC2)CCC1]

Step 1

Methyl 1-({4-[({4-[(trans-2-Hydroxycyclopentyl)oxy]-1,2-benzisoxazol-3-yl}oxy)methyl]piperidin-1-yl}methyl)cyclobutanecarboxylate The title compound was prepared according to the procedure described in Step 3 of EXAMPLE 2 using trans-2-{[3-(piperidin-4-ylmethoxy)-1,2-benzisoxazol-4-yl]oxy}cyclopentanol (EXAMPLE 33, Step 2) instead of 3-(piperidin-4-ylmethoxy)-4-(2,2,2-trifluoroethoxy)-1,2-benzisoxazole.

$^1$H-NMR (CDCl$_3$) δ: 7.41-7.35 (1H, m), 6.98 (1H, d, J=8.3 Hz), 6.63 (1H, d, J=7.9 Hz), 4.70-4.61 (1H, m), 4.44-4.35 (1H, m), 4.28-4.19 (2H, m), 3.78-3.72 (1H, m), 3.71 (3H, s), 2.88-2.77 (2H, m), 2.72 (2H, s) 2.51-2.34 (3H, m), 2.23-1.77 (11H, m), 1.75-1.43 (5H, m).

MS (ESI) m/z: 459 (M+H)$^+$.

Step 2

1-({4-[({4-[(trans-2-Hydroxycyclopentyl)oxy]-1,2-benzisoxazol-3-yl}oxy)methyl]piperidin-1-yl}methyl)cyclobutanecarboxylic acid The title compound was prepared according to the procedure described in Step 6 of EXAMPLE 1 using methyl 1-({4-[({4-[(trans-2-Hydroxycyclopentyl)oxy]-1,2-benzisoxazol-3-yl}oxy)methyl]piperidin-1-yl}methyl)cyclobutanecarboxylate (EXAMPLE 34, Step 1) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

$^1$H-NMR (CDCl$_3$) δ: 7.42-7.37 (1H, m), 6.97 (1H, d, J=8.4 Hz), 6.64 (1H, d, J=8.1 Hz), 4.69-4.65 (1H, m), 4.44-4.25 (4H, m), 3.49 (2H, s), 3.16-3.12 (2H, m), 2.83 (2H, s), 2.62-2.04 (7H, m), 2.03-1.65 (9H, m).

A signal due to CO$_2$H was not observed.

MS (ESI) m/z: 445 (M+H)$^+$, 443 (M−H)$^−$.

IR (KBr) ν: 2941, 2883, 1612, 1578, 1533, 1501, 1433, 1375, 1342, 1281, 1244, 1146, 1101, 1086, 1055, 993, 953, 914, 791, 662 cm$^{-1}$.

Anal. Calcd for C$_{24}$H$_{32}$N$_2$O$_6$·1.5H$_2$O: C, 61.13; H, 7.48; N, 5.94. Found: C, 61.30; H, 7.28; N, 5.72.

Example 35

4-({4-[({4-[(trans-2-Methoxycyclopentyl)oxy]-1,2-benzisoxazol-3-yl}oxy)methyl]piperidin-1-yl}-methyl)tetrahydro-2H-pyran-4-ol and its 4-methylbenzenesulfonate

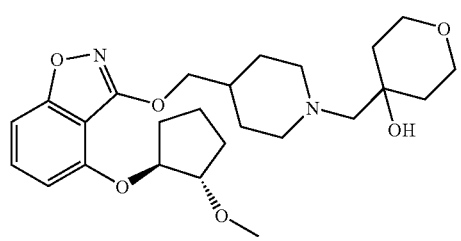

-continued

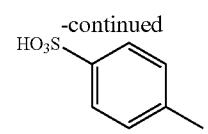

Step 1 tert-Butyl 4-{[(4-{[trans-2-methoxycyclopentyl]oxy}-1,2-benzisoxazol-3-yl)oxy]methyl}piperidine-1-carboxylate To a suspension of sodium hydride (60% oil dispersion 11 mg, 0.277 mmol) in tetrahydrofuran (5.0 mL) was added a solution of tert-butyl 4-{[(4-{[trans-2-hydroxycyclopentyl]oxy}-1,2-benzisoxazol-3-yl)oxy]methyl}piperidine-1-carboxylate (80 mg, 0.185 mmol, EXAMPLE 32, Step 1) in tetrahydrofuran (2.0 mL) at 0° C. under nitrogen. After being stirred at 0° C. for 30 min, methyliodide (14 µL, 0.222 mmol) was added to the mixture. The mixture was stirred at 0° C. for 3 h, water was added to the mixture. The mixture was extracted with ethyl acetate (30 mL×2) and washed with brine. The extracts were combined and dried over sodium sulfate and concentrated in vacuo to give an oil. The residual oil was purified by silica gel column chromatography (hexane/ethyl acetate 5:1 to 4:1) to give 78 mg (94%) of the title compound as a colorless viscous oil.

$^1$H-NMR (CDCl$_3$) δ: 7.40 (1H, t, J=8.4 Hz), 6.99 (1H, d, J=8.4 Hz), 6.66 (1H, d, J=7.9 Hz), 4.73 (1H, m), 4.27 (2H, d, J=6.2 Hz), 4.18 (2H, br), 3.88 (1H, m), 3.37 (3H, s), 2.78 (2H, m), 2.25-1.95 (3H, m), 1.95-1.65 (6H, m), 1.60-1.25 (2H, m), 1.47 (9H, s).

MS (ESI) m/z: 447 (M+H)$^+$, 445 (M−H)$^−$.

Step 2

4-[(trans-2-Methoxycyclopentyl)oxy]-3-(Piperidin-4-ylmethoxy)-1,2-benzisoxazole

The title compound was prepared according to the procedure described in Step 2 of EXAMPLE 2 using tert-butyl 4-{[(4-{[trans-2-methoxycyclopentyl]oxy}-1,2-benzisoxazol-3-yl)oxy]methyl}piperidine-1-carboxylate (EXAMPLE 35, Step 1) instead of tert-butyl 4-({[4-(2,2;2-trifluoroethoxy)-1,2-benzisoxazol-3-yl]oxy}methyl)piperidine-1-carboxylate.

$^1$H-NMR (CDCl$_3$) δ: 7.40 (1H, t, J=8.4 Hz), 6.99 (1H, d, J=8.4 Hz), 6.65 (1H, d, J=7.9 Hz), 4.74 (1H, brd, J=6.0 Hz), 4.23 (2H, d, J=6.6 Hz), 3.90 (1H, m), 3.37 (3H, s), 3.15 (2H, m), 2.67 (2H, m), 2.25-1.95 (3H, m), 1.90-1.60 (7H, m), 1.32 (2H, m).

Step 3

4-({4-[({4-[(trans-2-Methoxycyclopentyl)oxy]-1,2-benzisoxazol-3-yl}oxy)methyl]piperidin-1-yl}-methyl)tetrahydro-2H-pyran-4-ol The title compound was prepared according to the procedure described in Step 5 of EXAMPLE 8 using 4-[(trans-2-methoxycyclopentyl)oxy]-3-(piperidin-4-ylmethoxy)-1,2-benzisoxazole (EXAMPLE 35, Step 2) instead of 4-{[(isobutoxy-1,2-benzisoxazol-3-yl)oxy]methyl}piperidinium chloride.

$^1$H-NMR (CDCl$_3$) δ: 7.40 (1H, t, J=8.2 Hz), 6.99 (1H, d, J=8.4 Hz), 6.66 (1H, d, J=8.0 Hz), 4.74 (1H, brd, J=6.2 Hz), 4.25 (2H, 6.0 Hz), 3.89 (1H, br), 3.85-3.70 (4H, m), 3.37 (3H, s), 2.94 (2H, brd, J=11.5 Hz), 2.42 (2H, m), 2.35 (2H, s), 2.25-1.95 (2H, m), 1.95-1.40 (14H, m).

Step 4

4-({4-[({4-[(trans-2-Methoxycyclopentyl)oxy]-1,2-benzisoxazol-3-yl}oxy)methyl]piperidin-1-yl}-methyl)tetrahydro-2H-pyran-4-ol 4-methylbenzenesulfonate The title compound was prepared according to the procedure described in Step 6 of EXAMPLE 8 using 4-({4-[({4-[(trans-2-methoxycyclopentyl)oxy]-1,2-benzisoxazol-3-yl}oxy)methyl]piperidin-1-yl}-methyl)tetrahydro-2H-pyran-4-ol (EXAMPLE 35, Step 3) instead of 4-[(4-{[(4-Isobutoxy-1,2-benzisoxazol-3-yl)oxy]methyl}piperidin-1-yl)methyl]tetrahydro-2H-pyran-4-ol.

$^1$H-NMR (CDCl$_3$) δ: 7.78 (2H, d, J=8.1 Hz), 7.42 (1H, t, J=8.3 Hz), 7.20 (2H, d, J=7.9 Hz), 7.00 (1H, d, J=8.4 Hz), 6.67 (1H, d, J=7.9 Hz), 4.72 (1H, br), 4.27 (2H, d, J=7.0 Hz), 4.05-3.70 (6H, m), 3.36 (3H, s), 3.04 (2H, d, J=4.8 Hz), 2.80 (2H, m), 2.35 (3H, s), 2.30-1.55 (17H, m).

A signal due to SO$_3$H was not observed.
m.p.: 160.2° C.
Anal. Calcd for C$_{25}$H$_{36}$N$_2$O$_6$·C$_7$H$_8$O$_3$S: C, 60.74; H, 7.01; N, 4.43. Found: C, 60.47; H, 7.21; N, 4.34.

Example 36

4-({4-[({4-[(cis-2-Hydroxycyclopentyl)oxy]-1,2-benzisoxazol-3-yl}oxy)methyl]piperidin-1-yl}methyl)-tetrahydro-2H-pyran-4-ol

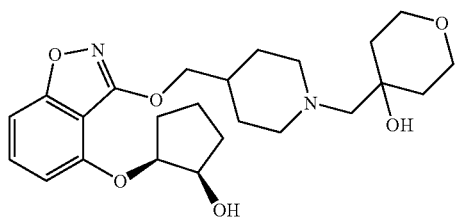 [SMILES: O[C@@H]1CCC[C@@H]1Oc1cccc2onc(OCC3CCN(CC4(O)CCOCC4)CC3)c12]

Step 1 tert-Butyl 4-[({4-[(2-oxocyclopentyl)oxy]-1,2-benzisoxazol-3-yl]oxy)methyl}piperidine-1-carboxylate To a mixture of tert-butyl 4-{[(4-{[trans-2-hydroxycyclopentyl]oxy}-1,2-benzisoxazole-3-yl)oxy]-methyl}piperidine-1-carboxylate (158 mg, 0.365 mmol, EXAMPLE 32, step 1), 2,2,6,6-tetramethyl-1-piperidinyloxy (TEMPO, 2.4 mg, 0.015 mmol), sodium bicarbonate (98.3 mg, 1.17 mmol), and tetra-n-butylammonium bromide (8.2 mg, 0.025 mmol) in dichloromethane (2 mL) and water (0.4 mL) was added N-chlorosuccinimide (60.3 mg, 0.453 mmol) at ambient temperature. After being stirred for 4 h, the mixture was quenched with aq. sodium thiosulfate. The mixture was extracted with ethyl acetate (20 mL) and washed with aq. potassium carbonate and brine. The extract was dried over magnesium sulfate and concentrated in vacuo to give 167 mg (crude mixture) of the title compound.

$^1$H-NMR (CDCl$_3$) δ: 7.39 (1H, t, J=8.2 Hz), 7.03 (1H, d, J=8.6 Hz), 6.73 (1H, d, J=7.9 Hz), 4.74 (1H, t, J=8.0 Hz), 4.26 (2H, d, J=6.4 Hz), 4.19 (2H, m), 2.77 (2H, t, J=12.2 Hz), 2.51 (1H, m), 2.39 (2H, m), 2.15-1.81 (6H, m), 1.47 (9H, s), 1.32 (2H, m).

TLC (NH gel, ethyl acetate/hexane=1:1) Rf: 0.17-0.03 (broad).

Step 2 tert-Butyl 4-[({4-[(cis-2-hydroxycyclopentyl)oxy]-1,2-benzisoxazole-3-yl}oxy)methyl]piperidine-1-carboxylate The product of the foregoing reaction (163 mg, EXAMPLE 36, step 1) was dissolved in tetrahydrofuran (1 mL). To this solution was added LS-selectride® (1 M solution in tetrahydrofuran, 2.0 mL, 2.0 mmol) at −78° C. After 5 h of stirring, the mixture was warmed to −20° C. and kept overnight at the temperature. 2N aq. sodium hydroxide and 30% hydrogen peroxide were added to the mixture, and the mixture was extracted with ethyl acetate (20 mL×2). Combined organic layers were washed with brine, dried over magnesium sulfate, and concentrated in vacuo to give an oil. The residual oil was purified by silica gel column chromatography (ethyl acetate/hexane 1:2 to 2:3) to give 101 mg (61% in two steps) of the title compound as a waxy solid.

$^1$H-NMR (CDCl$_3$) δ: 7.41 (1H, t, J=8.2 Hz), 7.02 (1H, d, J=8.4 Hz), 6.61 (1H, d, J=7.9 Hz), 4.65 (1H, m), 4.28 (2H, d, J=6.8 Hz), 4.24-4.11 (3H, m), 2.82-2.74 (3H, m), 2.13-1.50 (9H, m), 1.47 (9H, s), 1.30 (2H, m).

TLC (silica gel, ethyl acetate/hexane=1:2) Rf: 0.17.

Step 3. cis-2-{[3-(Pieridin-4-ylmethoxy)-1,2-benzisoxazol-4-yl]oxy}cyclopentanol hydrochloride The title compound was prepared according to the procedure described in Step 4 of EXAMPLE 8 using tert-butyl 4-[({4-[(cis-2-hydroxycyclopentyl)oxy]-1,2-benzisoxazole-3-yl}oxy)methyl]piperidine-1-carboxylate (EXAMPLE 36, Step 2) instead of tert-butyl 4-{[(4-isobutyoxy-1,2-benzisoxazol-3-yl)-oxy]methyl}piperidine-1-carboxylate.

$^1$H-NMR (DMSO-d$_6$) δ: 7.49 (1H, t, J=8.2 Hz), 7.08 (1H, d, J=8.4 Hz), 6.87 (1H, d, J=8.0 Hz), 4.72 (1H, m), 4.23 (2H, d, J=6.8 Hz), 4.17 (1H, m), 3.31 (2H, m), 2.91 (2H, m), 2.18?1.49 (11H, m). Three signals due to O$\underline{H}$ and N$\underline{H}$ were not observed.

MS (ESI) m/z: 333 (M—Cl)$^+$.
IR (KBr) ν: 3445, 2934, 1612, 1533, 1433, 1086 cm$^{-1}$.

Step 4

4-({4-[({4-[(cis-2-Hydroxycyclopentyl)oxy]-1,2-benzisoxazol-3-yl}oxy)methyl]piperidin-1-yl}-methyl)tetrahydro-2H-pyran-4-ol The title compound was prepared according to the procedure described in Step 5 of EXAMPLE 8 using cis-2-{[3-(Piperidin-4-ylmethoxy)-1,2-benzisoxazol-4-yl]oxy}cyclopentanol hydrochloride (EXAMPLE 36, Step 3) instead of 4-{[(isobutoxy-1,2-benzisoxazol-3-yl)oxy]methyl}piperidinium chloride.

$^1$H-NMR (CDCl$_3$) δ: 7.41 (1H, t, J=8.1 Hz), 7.01 (1H, d, J=8.4 Hz), 6.59 (1H, d, J=7.9 Hz), 4.66 (1H, q, J=6.4 Hz), 4.35-4.29 (3H, m), 3.86-3.78 (5H, m), 2.93 (2H, d, J=11.5 Hz), 2.40 (2H, td, J=11.4, 2.8 Hz), 2.33 (2H, s), 2.16 (1H, m), 1.94-1.47 (14H, m). A signal due to O$\underline{H}$ was not observed.

MS (ESI) m/z: 447 (M+H)$^+$.
m.p.: 140.8° C.
IR (KBr) v: 3566, 3422, 2945, 1612, 1537, 1356, 1097 cm$^{-1}$.
Anal. Calcd for $C_{24}H_{34}N_2O_6$: C, 64.55; H, 7.67; N, 6.27. Found: C, 64.52; H, 7.79; N, 6.14.

Example 37

4-({4-[({4-[(cis-2-Methoxycyclopentyl)oxy]-1,2-benzisoxazol-3-yl}oxy)methyl]piperidin-1-yl}methyl)-tetrahydro-2H-pyran-4-ol and its oxalate salt

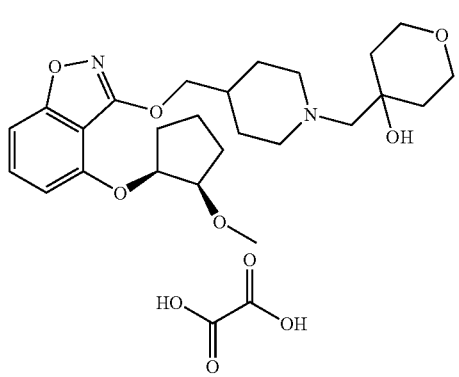

Step 1 tert-Butyl 4-[({4-[(cis-2-methoxycyclopentyl)oxy]-1,2-benzisoxazol-3-yl}oxy)methyl]-piperidine-1-carboxylate The title compound was prepared according to the procedure described in Step 1 of EXAMPLE 35 using tert-butyl 4-[({4-[(cis-2-hydroxycyclopentyl)oxy]-1,2-benzisoxazole-3-yl}oxy)methyl]piperidine-1-carboxylate (EXAMPLE 36, Step 2) instead of tert-butyl 4-{[(4-{[trans-2-hydroxycyclopentyl]oxy}-1,2-benzisoxazole-3-yl)oxy]methyl}piperidine-1-carboxylate.
$^1$H-NMR (CDCl$_3$) δ: 7.38 (1H, t, J=8.3 Hz), 6.97 (1H, d, J=8.3 Hz), 6.63 (1H, d, J=8.3 Hz), 4.85-4.76 (1H, m), 4.26 (2H, d, J=6.4 Hz), 3.88-3.78 (1H, m), 3.41 (3H, s), 2.85-2.65 (2H, m), 2.15-1.80 (7H, m), 1.75-1.20 (6H, m), 1.47 (9H, s).

Step 2

4-[(cis-2-Methoxycyclopentyl)oxy]-3-(piperidin-4-ylmethoxy)-1,2-benzisoxazole hydrochloride The title compound was prepared according to the procedure described in Step 4 of EXAMPLE 8 using tert-butyl 4-[({4-[(cis-2-methoxycyclopentyl)oxy]-1,2-benzisoxazol-3-yl}oxy)methyl]piperidine-1-carboxylate (EXAMPLE 37, Step 1) instead of tert-butyl 4-{[(4-isobutyoxy-1,2-benzisoxazol-3-yl)oxy]-methyl}piperidine-1-carboxylate.
$^1$H-NMR (CDCl$_3$) δ: 7.40 (1H, t, J=8.3 Hz), 6.99 (1H, d, J=8.3 Hz), 6.61 (1H, d, J=8.3 Hz), 4.84-4.76 (1H, m), 4.39-4.24 (2H, m) 3.92-3.75 (1H, m), 3.68-3.45 (2H, m), 3.38 (3H, s), 3.10-2.85 (2H, br), 2.33-2.07 (3H, m), 2.05-1.77 (8H, m).
A signal due to NH was not observed.
MS (ESI) m/z: 347 (M—Cl)$^+$.

Step 3

4-({4-[({4-[(cis-2-Methoxycyclopentyl)oxy]-1,2-benzisoxazol-3-yl}oxy)methyl]piperidin-1-yl}-methyl)tetrahydro-2H-pyran-4-ol The title compound was prepared according to the procedure described in Step 5 of EXAMPLE 8 using 4-[(cis-2-methoxycyclopentyl)oxy]-3-(piperidin-4-ylmethoxy)-1,2-benzisoxazole hydrochloride (EXAMPLE 38, Step 2) instead of 4-{[(isobutoxy-1,2-benzisoxazol-3-yl)oxy]methyl}piperidinium chloride.
$^1$H-NMR (CDCl$_3$) δ: 7.38 (1H, t, J=8.1 Hz), 6.97 (1H, d, J=8.1 Hz), 6.62 (1H, d, J=8.1 Hz), 4.86-4.76 (1H, m), 4.26 (2H, d, J=5.9 Hz), 3.90-3.71 (7H, m), 3.54 (1H, s), 3.40 (3H, s), 2.99-2.86 (2H, m), 2.50-2.32 (2H, m), 2.34 (2H, s), 2.05-1.75 (6H, m), 1.73-1.40 (8H, m).
MS (ESI) m/z: 461 (M+H)$^+$.

Step 3

4-({4-[({4-[(cis-2-Methoxycyclopentyl)oxy]-1,2-benzisoxazol-3-yl}oxy)methyl]piperidin-1-yl}-methyl)tetrahydro-2H-pyran-4-ol oxalate To a solution of 4-({4-[({4-[(cis-2-methoxycyclopentyl)oxy]-1,2-benzisoxazol-3-yl}oxy)methyl]piperidin-1-yl}methyl)-tetrahydro-2H-pyran-4-ol (47 mg, 0.1 mmol, EXAMPLE 37, Step 3) in diethylether (5 mL) was added oxalic acid (14 mg, 0.15 mmol) in diethylether (5 mL). After being stirred at room temperature for 3 hr, the formed precipitate was collected by filtration to give 31 mg (56%) of the title compound as a white solid.
$^1$H-NMR (CDCl$_3$) δ: 7.41 (1H, t, J=8.1 Hz), 6.99 (1H, d, J=8.1 Hz), 6.60 (1H, d, J=8.1 Hz), 4.86-4.74 (1H, m), 4.43-4.20 (2H, m), 4.40-3.70 (7H, m), 3.60-2.60 (6H, m), 3.36 (3H, s), 2.31-1.50 (14H, m).
A signal due to CO$_2$H was not observed.
IR (KBr) v: 3400, 2951, 1612, 1535, 1433, 1373, 1283, 1086, 719 cm$^{-1}$
Anal. Calcd for $C_{25}H_{36}N_2O_6 \cdot 1.5 \ C_2H_2O_4$: C, 56.46; H, 6.60; N, 4.70. Found: C, 56.79; H, 6.71; N, 4.66.

Example 38

2-{[3-({1-[(4-Hydroxytetrahydro-2H-pyran-4-yl)methyl]piperidin-4-yl}methoxy)-1,2-benzisoxazol-4-yl]oxy}cyclopentanone

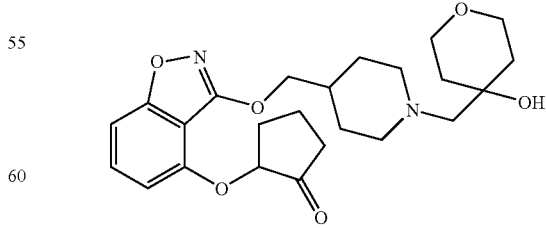

To a solution of oxalyl chloride (9 μL, 0.1 mmol) in dichloromethane (0.5 mL) was added dimethylsulfoxide (9 μM, 0.12 mmol) at −78° C. under nitrogen. The mixture was stirred for 5 min, a solution of 4-({4-[({4-[(trans-2-Hydroxycyclopentyl)oxy]-1,2-benzisoxazol-3-yl}oxy)methyl]-piperidin-1-yl}methyl)tetrahydro-2H-pyran-4-ol (EXAMPLE 32) in dichloromethane (1.5 mL) was added to the mixture. After being stirred for 5 min, triethylamine (45 μL, 0.33 mmol) was added to the mixture. The mixture was allowed to warmed to room temperature and stirred for 3 h. Water was added to the mixture and the mixture was extracted with ethyl acetate and washed with brine. The extract was dried over sodium sulfate and concentrated in vacuo to give an oil. The residual oil was purified by silica gel column chromatography (dichloromethane/methanol 20:1) to give 13 mg (45%) of the title compound as a white solid.

$^1$H-NMR (CDCl$_3$) δ: 7.40 (1H, t, J=8.4 Hz), 7.04 (1H, d, J=8.4 Hz), 6.72 (1H, d, J=8.4 Hz), 4.78-4.69 (1H, m), 4.26 (2H, dd, J=5.7, 2.0 Hz), 3.87-3.70 (4H, m), 3.02-2.85 (2H, m), 2.62-1.40 (19H, m). A signal due to OH was not observed.

MS (ESI) m/z: 445 (M+H)$^+$.

m.p.: 133.1° C.

IR (KBr) ν: 3400, 2947, 1759, 1616, 1533, 1433, 1364, 1283, 1112, 993, 785 cm$^{-1}$

Anal. Calcd for C$_{24}$H$_{32}$N$_2$O$_6$·0.3H$_2$O: C, 64.07; H, 7.30; N, 6.23. Found: C, 63.84; H, 7.29; N, 6.04.

Example 39

4-({4-[({4-[(trans-3-Hydroxycyclopentyl)oxy]-1,2-benzisoxazol-3-yl}oxy)methyl]piperidin-1-yl}methyl)tetrahydro-2H-pyran-4-ol

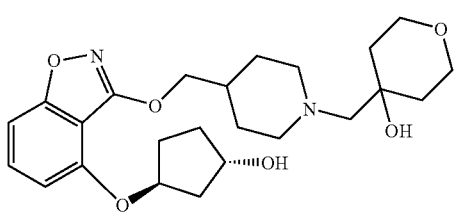 [SMILES: O[C@H]1CC[C@H](Oc2cccc3onc(OCC4CCN(CC5(O)CCOCC5)CC4)c23)C1]

Step 1 tert-Butyl 4-[({4-[(trans-3-hydroxycyclopentyl)oxy]-1,2-benzisoxazol-3-yl}oxy)methyl]piperidine-1-carboxylate The title compound was prepared according to the procedure described in Step 2 of EXAMPLE 7 using tert-butyl 4-{[(4-hydroxy-1,2-benzisoxazol-3-yl)oxy]methyl}piperidine-1-carboxylate (EXAMPLE 17, step 2) and 1,3-cyclopentanediol (mixture of isomers, cis:trans=ca. 5:1) instead of 4-(benzyloxy)-1,2-benzisoxazol-3-ol and tert-butyl 4-(2-hydroxyethyl)piperidine-1-carboxylate.

$^1$H-NMR (CDCl$_3$) δ: 7.41 (1H, t, J=8.2 Hz), 7.00 (1H, d, J=8.4 Hz), 6.61 (1H, d, J=7.9 Hz), 5.08 (1H, m), 4.38 (1H, m), 4.28-4.10 (4H, m), 2.96 (1H, d, J=7.2 Hz), 2.78 (2H, t, J=12.5 Hz), 2.23-1.78 (9H, m), 1.46 (9H, s), 1.30 (m, 2H).

A signal due to OH was not observed.

TLC (silica gel, ethyl acetate/hexane=1:1) Rf: 0.27.

Step 2. trans-3-{[3-(Piperidin-4-ylmethoxy)-1,2-benzisoxazol-4-yl]oxy}cyclopentanol hydrochloride The title compound was prepared according to the procedure described in Step 4 of EXAMPLE 8 using tert-butyl 4-[({4-[(trans-3-hydroxycyclopentyl)oxy]-1,2-benzisoxazol-3-yl}oxy)methyl]piperidine-1-carboxylate (EXAMPLE 39, Step 1) instead of tert-butyl 4-{[(4-isobutyoxy-1,2-benzisoxazol-3-yl)-oxy]methyl}piperidine-1-carboxylate.

$^1$H-NMR (DMSO-d$_6$) δ: 9.05 (1H, br), 8.63 (1H, br), 7.51 (1H, t, J=8.2 Hz), 7.09 (1H, d, J=8.4 Hz), 6.75 (1H, d, J=8.1 Hz), 4.88 (1H, m), 4.23 (2H, d, J=6.8 Hz), 4.15 (1H, quint, J=5.8 Hz), 3.31 (2H, m), 2.91 (2H, q, J=11.5 Hz), 2.18 (1H, m), 1.99-1.49 (10H, m).

A signal due to OH was not observed.

MS (ESI) m/z: 333 (M—Cl)$^+$.

Step 3

4-({4-[({4-[(trans-3-Hydroxycyclopentyl)oxy]-1,2-benzisoxazol-3-yl}oxy)methyl}piperidin-1-yl}-methyl)tetrahydro-2H-pyran-4-ol The title compound was prepared according to the procedure described in Step 5 of EXAMPLE 8 using trans-3-{[3-(piperidin-4-ylmethoxy)-1,2-benzisoxazol-4-yl]oxy}cyclopentanol hydrochloride (EXAMPLE 39, Step 2) instead of 4-{[(isobutoxy-1,2-benzisoxazol-3-yl)oxy]methyl}piperidinium chloride.

$^1$H-NMR (CDCl$_3$) δ: 7.41 (1H, t, J=8.2 Hz), 6.99 (1H, d, J=8.2 Hz), 6.60 (1H, d, J=7.9 Hz), 5.06 (1H, m), 4.39 (1H, m), 4.31-4.25 (2H, m), 3.85-3.77 (4H, m), 3.00 (2H, br), 2.91 (2H, d, J=11.5 Hz), 2.42 (2H, t, J=11.5 Hz), 2.33 (2H, s), 2.21-1.74 (9H, m), 1.64-1.45 (6H, m).

MS (ESI) m/z: 447 (M+H)$^+$.

m.p.: 147.1° C.

IR (KBr) ν: 3346, 3279, 2957, 1614, 1531, 1431, 1090 cm$^{-1}$.

Anal. Calcd for C$_{24}$H$_{34}$N$_2$O$_6$·0.35H$_2$O: C, 63.66; H, 7.72; N, 6.19. Found: C, 63.70; H, 7.85; N, 6.05.

Example 40

4-({4-[({4-[(cis-2-Hydroxycyclohexyloxyl)oxy]-1,2-benzisoxazol-3-yl}oxy)methyl}piperidin-1-yl}-methyl)tetrahydro-2H-pyran-4-ol

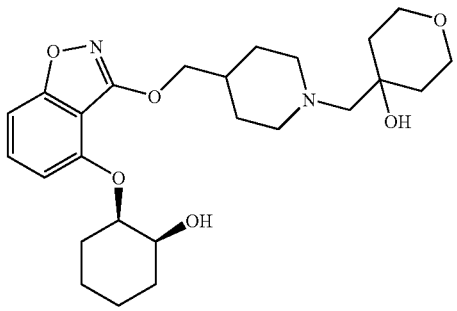 [SMILES: O[C@H]1CCCC[C@H]1Oc1cccc2onc(OCC3CCN(CC4(O)CCOCC4)CC3)c12]

Step 1 tert-Butyl 4-[({4-[(trans-2-hydroxycyclohexyl)oxy]-1,2-benzisoxazole-3-yl}oxy)methyl]piperidine-1-carboxylate The title compound was prepared according to the procedure described in Step 1 of EXAMPLE 31 using tert-butyl 4-{[(4-hydroxy-1,2-benzisoxazol-3-yl)oxy]methyl}piperidine-1-carboxylate (EXAMPLE 17, step 2) and cyclohexene oxide instead of 1-oxaspiro[2.4]heptane.

¹H-NMR (CDCl₃) δ: 7.40 (1H, t, J=8.2 Hz), 7.02 (1H, d, J=8.4 Hz), 6.71 (1H, d, J=8.1 Hz), 4.29 (2H, d, J=6.6 Hz), 4.16 (3H, m), 3.77 (1H, m), 2.75 (3H, m), 2.25 (1H, d, J=12.3 Hz), 2.10 (2H, m), 1.57 (4H, m), 1.47 (9H, s), 1.36 (6H, m).

TLC (silica gel, ethyl acetate/hexane=1:2) Rf: 0.23.

TLC (NH gel, ethyl acetate/hexane=1:1) Rf: 0.37.

Step 2 tert-Butyl 4-[({4-[(2-oxocyclohexyl)oxy]-1,2-benzisoxazol-3-yl}oxy)methyl]piperidine-1-carboxylate The title compound was prepared according to the procedure described in Step 1 of EXAMPLE 36 using tert-butyl 4-[({4-[(trans-2-hydroxycyclohexyl)oxy]-1,2-benzisoxazole-3-yl}oxy)methyl]piperidine-1-carboxylate (EXAMPLE 40, step 1) instead of tert-butyl 4-[({4-[(trans-2-hydroxycyclopentyl)oxy]-1,2-benzisoxazole-3-yl}oxy)methyl]piperidine-1-carboxylate.

¹H-NMR (CDCl₃) δ: 7.34 (1H, t, J=8.2 Hz), 7.01 (1H, d, J=8.4 Hz), 6.46 (1H, d, J=7.9 Hz), 4.74 (1H, dd J=8.2, 4.7 Hz), 4.29 (2H, d, J=6.2 Hz), 4.16 (2H, m), 2.77-2.63 (3H, m), 2.39-1.75 (10H, m), 1.47 (9H, s), 1.38 (2H, m).

TLC (silica gel, ethyl acetate/hexane=1:2) Rf: 0.25.

Step 3 tert-Butyl 4-[({4-[(cis-2-hydroxycyclohexyl)oxy]-1,2-benzisoxazole-3-yl}oxy)methyl]piperidine-1-carboxylate The title compound was prepared according to the procedure described in Step 2 of EXAMPLE 36 using tert-butyl 4-[({4-[(2-oxocyclohexyl)oxy]-1,2-benzisoxazol-3-yl}oxy)methyl]piperidine-1-carboxylate (EXAMPLE 40, step 2) instead of tert-Butyl 4-[({4-[(2-oxocyclopentyl)oxy]-1,2-benzisoxazol-3-yl}oxy)methyl]piperidine-1-carboxylate.

¹H-NMR (CDCl₃) δ: 7.40 (1H, t, J=8.2 Hz), 7.01 (1H, d, J=8.4 Hz), 6.68 (1H, d, J=7.9 Hz), 4.58 (1H, m), 4.29 (2H, d, J=6.4 Hz), 4.16 (2H, m), 3.89 (1H, m), 2.77 (2H, t, J=11.9 Hz), 2.37 (1H, d, J=7.1 Hz), 2.08 (2H, m), 1.94-1.62 (6H, m), 1.47 (9H, s), 1.40-1.23 (5H, m).

TLC (silica gel, ethyl acetate/hexane=1:2) Rf: 0.22.

Step 4 cis-2-{[3-(Piperidin-4-ylmethoxy)-1,2-benzisoxazol-4-yl]oxy}cyclohexanol hydrochloride The title compound was prepared according to the procedure described in Step 4 of EXAMPLE 8 using tert-butyl 4-[({4-[(cis-2-hydroxycyclohexyl)oxy]-1,2-benzisoxazole-3-yl}oxy)methyl]piperidine-1-carboxylate (EXAMPLE 40, Step 3) instead of tert-butyl 4-{[(4-isobutyoxy-1,2-benzisoxazol-3-yl)-oxy]methyl}piperidine-1-carboxylate.

¹H-NMR (DMSO-d₆) δ: 7.49 (1H, t, J=8.2 Hz), 7.07 (1H, d, J=8.4 Hz), 6.90 (1H, d, J=8.1 Hz), 4.69 (1H, dd, J=10.7, 4.6 Hz), 4.23 (2H, d, J=6.9 Hz), 3.77 (1H, br), 3.31 (2H, m), 2.92 (2H, m), 2.17 (1H, m), 2.0-1.34 (12H, m).

Three signals due to OH and NH were not observed.

MS (ESI) m/z: 347 (M—Cl)⁺.

IR (KBr) ν: 3410, 2937, 1611, 1531, 1431, 1082 cm⁻¹.

Step 5

4-({4-[({4-[(cis-2-Hydroxycyclohexyl)oxy]-1,2-benzisoxazol-3-yl}oxy)methyl]piperidin-1-yl}-methyl)tetrahydro-2H-pyran-4-ol The title compound was prepared according to the procedure described in Step 5 of EXAMPLE 8 using trans-3-{[3-(piperidin-4-ylmethoxy)-1,2-benzisoxazol-4-yl]oxy}cyclopentanol hydrochloride (EXAMPLE 40, Step 4) instead of 4-{[(isobutoxy-1,2-benzisoxazol-3-yl)oxy]methyl}piperidinium chloride.

¹H-NMR (CDCl₃) δ: 7.40 (1H, t, J=8.2 Hz), 7.00 (1H, d, J=8.4 Hz), 6.65 (1H, d, J=8.1 Hz), 4.51 (1H, m), 4.29 (2H, d, J=4.8 Hz), 4.02 (1H, m), 3.85-3.77 (5H, m), 2.94 (2H, d, J=11.2 Hz), 2.39 (2H, td, J=11.4, 2.3 Hz), 2.33 (2H, s), 2.05-1.39 (17H, m).

A signal due to OH was not observed.

MS (ESI) m/z: 461 (M+H)⁺.

m.p.: 125.2° C.

IR (KBr) ν: 3420, 2941, 1611, 1533, 1431, 1362, 1092 cm⁻¹.

Anal. Calcd for $C_{25}H_{36}N_2O_6$: C, 65.20; H, 7.88; N, 6.08. Found: C, 65.01; H, 7.99; N, 5.87.

Example 41

4-({4-[({4-[(trans-4-Hydroxycyclohexyl)oxy]-1,2-benzisoxazol-3-yl}oxy)methyl]piperidin-1-yl}-methyl)tetrahydro-2H-pyran-4-ol

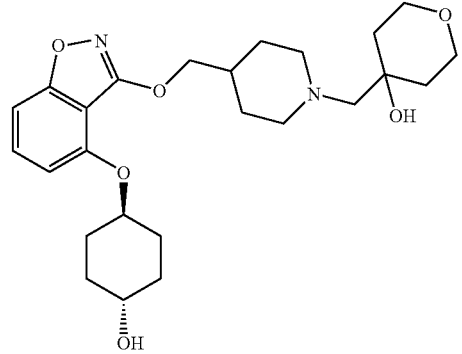 [SMILES: OC1(CN2CCC(COc3noc4cccc(O[C@H]5CC[C@H](O)CC5)c34)CC2)CCOCC1]

Step 1 tert-Butyl 4-[({4-[(trans-4-hydroxycyclohexyl)oxy]-1,2-benzisoxazol-3-yl}oxy)methyl]piperidine-1-carboxylate The title compound was prepared according to the procedure described in Step 2 of EXAMPLE 7 using tert-butyl 4-{[(4-hydroxy-1,2-benzisoxazol-3-yl)oxy]methyl}piperidine-1-carboxylate (EXAMPLE 17, step 2) and 1,4-cyclopentanediol (mixture of isomers, cis: trans=ca. 1:1) instead of 4-(benzyloxy)-1,2-benzisoxazol-3-ol and tert-butyl 4-(2-hydroxyethyl)piperidine-1-carboxylate.

¹H-NMR (CDCl₃) δ: 7.39 (1H, t, J=8.1 Hz), 6.97 (1H, d, J=8.4 Hz), 6.62 (1H, d, J=7.9 Hz), 4.51 (1H, m), 4.27 (2H, d, J=6.3 Hz), 4.16 (2H, m), 3.90 (1H, m), 2.76 (2H, t, J=12.4 Hz), 2.15-2.10 (4H, m), 1.82 (2H, d, J=12.0 Hz), 1.80-1.25 (16H).

A signal due to OH was not observed.

TLC (silica gel, ethyl acetate/hexane=1:1) Rf: 0.20.

Step 2. trans-4-{[3-(Piperidin-4-ylmethoxy)-1,2-benzisoxazol-4-yl]oxy}cyclohexanol hydrochloride The title compound was prepared according to the procedure described in Step 4 of EXAMPLE 8 using tert-butyl 4-[({4-[(trans-4-hydroxycyclohexyl)oxy]-1,2-benzisoxazol-3-yl}oxy)methyl]piperidine-1-carboxylate (EXAMPLE 41, Step 1) instead of tert-butyl 4-{[(4-isobutyoxy-1,2-benzisoxazol-3-yl)oxy]-methyl}piperidine-1-carboxylate.

$^1$H-NMR (DMSO-d$_6$) δ: 8.97 (1H, br), 8.63 (1H, br), 7.51 (1H, t, J=8.2 Hz), 7.00 (1H, d, J=8.2 Hz), 6.87 (1H, d, J=8.0 Hz), 4.56 (1H, m), 4.23 (2H, d, J=6.9 Hz), 3.63 (1H, m), 3.31 (2H, m), 2.91 (2H, q, J=10.5 Hz), 2.18 (1H, m), 2.05-1.80 (6H, m), 1.60-1.30 (6H, m).

A signal due to O$\underline{H}$ was not observed.

MS (ESI) m/z: 347 (M—Cl)$^+$.

Step 3

4-({4-[({4-[(trans-4-Hydroxycyclohexyl)oxy]-1,2-benzisoxazol-3-yl}oxy)methyl]piperidin-1-yl}-methyl)tetrahydro-2H-pyran-4-ol The title compound was prepared according to the procedure described in Step 5 of EXAMPLE 8 using trans-4-{[3-(piperidin-4-ylmethoxy)-1,2-benzisoxazol-4-yl]oxy}cyclohexanol hydrochloride (EXAMPLE 41, Step 2) instead of 4-{[(isobutoxy-1,2-benzisoxazol-3-yl)oxy]methyl}piperidinium chloride.

$^1$H-NMR (CDCl$_3$) δ: 7.38 (1H, t, J=8.2 Hz), 6.98 (1H, d, J=8.4 Hz), 6.62 (1H, d, J=8.1 Hz), 4.52 (1H, m), 4.27 (2H, d, J=5.9 Hz), 3.91 (1H, m), 3.82-3.49 (4H, m), 2.93 (2H, d, J=11.7 Hz), 2.41 (2H, t, J=11:7 Hz), 2.34 (2H, s), 2.11 (4H, m), 1.83-1.44 (13H, m).

Two signals due to O$\underline{H}$ were not observed.

MS (ESI) m/z: 461 (M+H)$^+$.

IR (KBr) ν: 3396, 2939, 1611, 1529, 1431, 1366, 1097, 1080 cm$^{-1}$.

Example 42

4-({4-[({4-[(trans-4-Hydroxycyclohexyl)oxy]-1,2-benzisoxazol-3-yl}oxy)methyl]piperidin-1-yl}-methyl)tetrahydro-2H-pyran-4-carboxylic acid

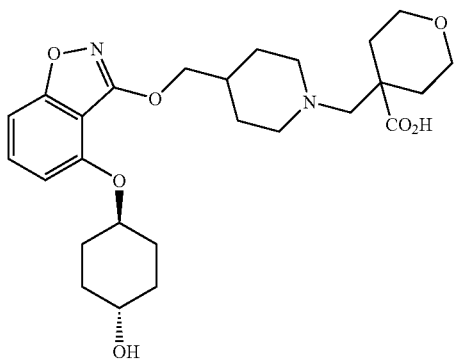 [SMILES: O=C(O)C1(CN2CCC(COc3noc4cccc(O[C@H]5CC[C@H](O)CC5)c34)CC2)CCOCC1]

Step 1 trans-4-{[3-(Piperidin-4-ylmethoxy)-1,2-benzisoxazol-4-yl]oxy}cyclohexanol

The title compound was prepared according to the procedure described in Step 2 of EXAMPLE 2 using tert-butyl 4-[({4-[(trans-4-hydroxycyclohexyl)oxy]-1,2-benzisoxazol-3-yl}oxy)methyl]piperidine-1-carboxylate (EXAMPLE 41, step 1) instead of tert-butyl 4-({[4-(2,2,2-trifluoroethoxy)-1,2-benzisoxazol-3-yl]oxy}-methyl)piperidine-1-carboxylate.

$^1$H-NMR (CDCl$_3$) δ: 7.38 (1H, t, J=8.2 Hz), 6.98 (1H, d, J=8.4 Hz), 6.62 (1H, d, J=8.0 Hz), 4.52 (1H, m), 4.24 (2H, d, J=6.6 Hz), 3.92 (1H, m), 3.14 (2H, d, J=12.3 Hz), 2.67 (2H, t, J=12.2 Hz), 2.11 (5H, m), 1.85 (2H, d, J=11.9 Hz), 1.71 (2H, m), 1.5 (2H, m), 1.31 (2H, m).

Two signals due to O$\underline{H}$ and N$\underline{H}$ were not observed.

MS (ESI) m/z: 347 (M+H)$^+$.

IR (KBr) ν: 2939, 1612, 1541, 1431, 1363, 1086 cm$^{-1}$.

Step 2

Methyl 4-({4-[({4-[(trans-4-hydroxycyclohexyl)oxy]-1,2-benzisoxazol-3-yl}oxy)methyl]piperidin-1-yl}methyl)tetrahydro-2H-pyran-4-carboxylate The title compound was prepared according to the procedure described in Step 3 of EXAMPLE 2 using trans-4-{[3-(Piperidin-4-ylmethoxy)-1,2-benzisoxazol-4-yl]oxy}cyclohexanol (EXAMPLE 42, Step 1) and methyl 4-formyltetrahydro-2H-pyran-4-carboxylate (EXAMPLE 18, Step 1) instead of 3-(piperidin-4-ylmethoxy)-4-(2,2,2-trifluoroethoxy)-1,2-benzisoxazole and methyl 1-formylcyclobutanecarboxylate.

$^1$H-NMR (CDCl$_3$) δ: 7.38 (1H, t, J=8.2 Hz), 6.97 (1H, d, J=8.4 Hz), 6.63 (1H, d, J=7.9 Hz), 4.52 (1H, m), 4.25 (2H, d, J=5.6 Hz), 3.94 (1H, m), 3.83 (2H, dd, J=11.7, 3.4 Hz), 3.72 (3H, s), 3.46 (2H, t, J=11.5 Hz), 2.79 (2H, d, J=11.4 Hz), 2.50 (2H, s), 2.25 (2H, t, J=10.5 Hz), 2.11-2.00 (7H, m), 1.77-1.47 (10H, m).

A signal due to O$\underline{H}$ was not observed.

TLC (silica gel, ethyl acetate/hexane 1:1) Rf: 0.24.

Step 3

4-({4-[({4-[(trans-4-Hydroxycyclohexyl)oxy]-1,2-benzisoaol-3-yl}oxy)methyl]piperidin-1-yl}-methyl)tetrahydro-2H-pyran-4-carboxylic acid The title compound was prepared according to the procedure described in Step 6 of EXAMPLE 1 using methyl 4-({4-[({4-[(trans-4-hydroxycyclohexyl)oxy]-1,2-benzisoxazol-3-yl}oxy)methyl]piperidin-1-yl}methyl)tetrahydro-2H-pyran-4-carboxylate (EXAMPLE 42, Step 2) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

$^1$H-NMR (DMSO-d$_6$) δ: 7.48 (1H, t, J=8.1 Hz), 7.07 (1H, d, J=8.4 Hz), 6.84 (1H, d, J=8.2 Hz), 4.55 (1H, m), 4.17 (2H, d, J=5.6 Hz), 3.67 (3H, m), 3.31 (2H, m), 2.84 (2H, d, J=12.1 Hz), 2.50 (2H, s), 2.22 (2H, t, J=11.9 Hz), 1.99 (2H, m), 1.90-1.60 (7H, m), 1.51-1.30 (8H, m).

Two signals due to O$\underline{H}$ and CO$_2$$\underline{H}$ were not observed.

MS (ESI) m/z: 489 (M+H)$^+$, 487 (M−H)$^−$.

IR (KBr) ν: 1607, 1531, 1431, 1369, 1085 cm$^{-1}$.

Anal. Calcd for C$_{26}$H$_{36}$N$_2$O$_7$·0.2H$_2$O: C, 63.45; H, 7.45; N, 5.69. Found: C, 63.37; H, 7.46; N, 5.58.

Example 43

4-({4-[({4-[(cis-4-Hydroxycyclohexyl)oxy]-1,2-benzisoxazol-3-yl}oxy)methyl]piperidin-1-yl}methyl)-tetrahydro-2H-pyran-4-carboxylic acid

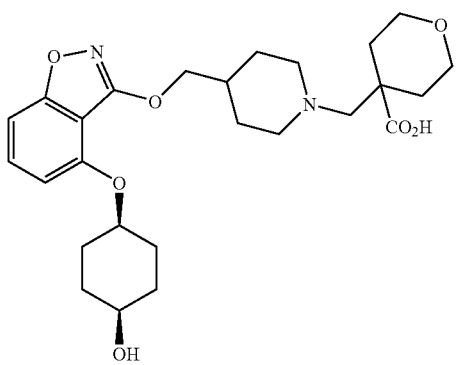 [SMILES: O=C(O)C1(CN2CCC(COc3noc4cccc(O[C@H]5CC[C@@H](O)CC5)c34)CC2)CCOCC1]

Step 1 tert-Butyl 4-[({4-[(cis-4-{[tert-butyl(dimethyl)silyl]oxy}hydroxycyclohexyl)oxy]-1,2-benzisoxazol-3-yl}oxy)methyl]piperidine-1-carboxylate The title compound was prepared according to the procedure described in Step 2 of EXAMPLE 7 using tert-butyl 4-{[(4-hydroxy-1,2-benzisoxazol-3-yl)oxy]methyl}piperidine-1-carboxylate (EXAMPLE 17, step 2) and trans-4-{[tert-butyl(dimethyl)silyl]oxy}cyclohexanol (*Org. Lett.* 2003, 5, 2319, "more polar isomer") instead of 4-(benzyloxy)-1,2-benzisoxazol-3-ol and tert-butyl 4-(2-hydroxyethyl)piperidine-1-carboxylate.

$^1$H-NMR (CDCl$_3$) δ: 7.37 (1H, t, J=8.2 Hz), 6.96 (1H, d, J=8.4 Hz), 6.61 (1H, d, J=7.9 Hz), 4.50 (1H, m), 4.25 (2H, d, J=7.2 Hz), 4.14 (2H, m), 3.77 (1H, m), 2.77 (2H, t, J=11.6 Hz), 2.05 (2H, m), 1.85-1.26 (m, 20H), 0.91 (9H, s), 0.07 (6H, s). TLC (silica gel, ethyl acetate/hexane=1:2) Rf: 0.60.

Step 2 cis-4-{[3-(Piperidin-4-ylmethoxy)-1,2-benzisoxazol-4-yl]oxy}cyclohexanol

The title compound was prepared according to the procedure described in Step 2 of EXAMPLE 2 using tert-butyl 4-[({4-[(cis-4-{[tert-butyl(dimethyl)silyl]oxy}hydroxycyclohexyl)oxy]-1,2-benzisoxazol-3-yl}-oxy)methyl]piperidine-1-carboxylate (EXAMPLE 43, step 1) instead of tert-butyl 4-({[4-(2,2,2-trifluoroethoxy)-1,2-benzisoxazol-3-yl]oxy}methyl)piperidine-1-carboxylate.

$^1$H-NMR (CDCl$_3$) δ: 7.38 (1H, t, J=8.2 Hz), 6.95 (1H, d, J=8.4 Hz), 6.63 (1H, d, J=7.9 Hz), 4.78 (1H, br), 4.37 (2H, d, J=2.3 Hz), 3.58 (1H, m), 3.17 (2H, d, J=11.5 Hz), 2.64 (2H, t, J=11.5 Hz), 2.11 (2H, d, J=14.7 Hz), 1.99-1.91 (7H, m), 1.66 (4H, m).

Two signals due to OH and NH were not observed.
MS (ESI) m/z: 347 (M+H)$^+$.
IR (KBr) ν: 3285, 2941, 1611, 1533, 1431, 1361, 1082 cm$^{-1}$.

Step 3

Methyl 4-({4-[({4-[(cis-4-hydroxycyclohexyl)oxy]-1,2-benzisoxazol-3-yl}oxy)methyl]piperidin-1-yl}-methyl)tetrahydro-2H-pyran-4-carboxylate The title compound was prepared according to the procedure described in Step 3 of EXAMPLE 2 using cis-4-{[3-(piperidin-4-ylmethoxy)-1,2-benzisoxazol-4-yl]oxy}cyclohexanol (EXAMPLE 43, Step 2) and methyl 4-formyltetrahydro-2H-pyran-4-carboxylate (EXAMPLE 18, Step 1) instead of 3-(piperidin-4-ylmethoxy)-4-(2,2,2-trifluoroethoxy)-1,2-benzisoxazole and methyl 1-formylcyclobutanecarboxylate.

$^1$H-NMR (CDCl$_3$) δ: 7.37 (1H, t, J=8.2 Hz), 6.96 (1H, d, J=8.4 Hz), 6.60 (1H, d, J=7.9 Hz), 4.58 (1H, br), 4.26 (2H, d, J=4.9 Hz), 3.85-3.77 (4H, m), 3.72 (3H, s), 3.47 (2H, t, J=10.8 Hz), 2.79 (2H, d, J=11.4 Hz), 2.50 (2H, s), 2.28-2.01 (6H, m), 1.87-1.51 (13H, m). TLC (silica gel, ethyl acetate/hexane 1:1) Rf: 0.18.

Step 4

4-({4-[({4-[(cis-4-Hydroxycyclohexyl)oxy]-1,2-benzisoxaol-3-yl}oxy)methyl]piperidin-1-yl}methyl)tetrahydro-2H-pyran-4-carboxylic acid The title compound was prepared according to the procedure described in Step 6 of EXAMPLE 1 using methyl 4-({4-[({4-[(cis-4-hydroxycyclohexyl)oxy]-1,2-benzisoxazol-3-yl}oxy)methyl]piperidin-1-yl}-methyl)tetrahydro-2H-pyran-4-carboxylate (EXAMPLE 43, Step 3) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

$^1$H-NMR (CDCl$_3$) δ: 7.39 (1H, t, J=8.4 Hz), 6.97 (1H, d, J=8.4 Hz), 6.61 (1H, d, J=8.1 Hz), 4.62 (1H, m), 4.35 (2H, d, J=4.8 Hz), 3.90 (2H, d, J=11.2 Hz), 3.84-3.75 (3H, m), 3.26 (2H, d, J=12.2 Hz), 2.64 (4H, m), 2.07 (2H, m), 2.00-1.60 (13H, m), 1.50 (2H, m).

Two signals due to OH and NH were not observed.
MS (ESI) m/z: 489 (M+H)$^+$, 487 (M−H)$^-$.
IR (KBr) ν: 3393, 2949, 1616, 1529, 1371, 1084 cm$^{-1}$.
Anal. Calcd for C$_{26}$H$_{36}$N$_2$O$_7$.2.2H$_2$O: C, 59.12; H, 7.71; N, 5.30. Found: C, 59.08; H, 7.68; N, 5.20.

Example 44 trans-4-({4-[({4-[(cis-4-Hydroxycyclohexyl)oxy]-1,2-benzisoxazol-3-yl}oxy)methyl]piperidin-1-yl}-methyl)cyclohexanecarboxylic acid

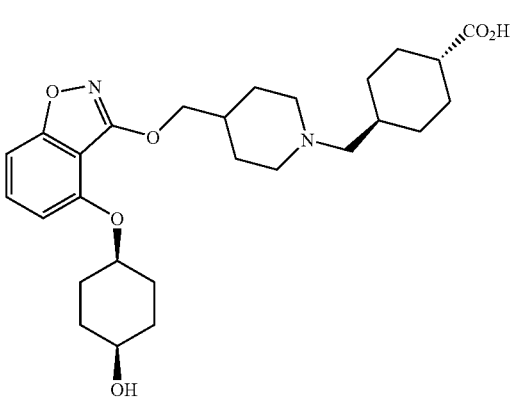 [SMILES: O=C(O)[C@H]1CC[C@H](CN2CCC(COc3noc4cccc(O[C@H]5CC[C@@H](O)CC5)c34)CC2)CC1]

Step 1

Methyl trans-4-({4-[({4-[(cis-4-hydroxycyclohexyl)oxy]-1,2-benzisoxazol-3-yl}oxy)methyl]piperidin-1-yl}methyl)cyclohexanecarboxylate The title compound was prepared according to the procedure described in Step 3 of EXAMPLE 2 using cis-4-{[3-(piperidin-4-ylmethoxy)-1,2-benzisoxazol-4-yl]oxy}cyclohexanol (EXAMPLE 43, Step 2) and methyl trans-4-formylcyclohexanecarboxylate (JP 490-48639) instead of 3-(piperidin-4-ylmethoxy)-4-(2,2,2-trifluoroethoxy)-1,2-benzisoxazole and methyl 1-formylcyclobutanecarboxylate.
$^1$H-NMR (CDCl$_3$) δ: 7.38 (1H, dd, J=8.1, 8.4 Hz), 6.96 (1H, d, J=8.4 Hz), 6.62 (1H, d, J=8.1 Hz), 4.77-4.67 (1H, m), 4.38-4.31 (2H, m), 3.78-3.63 (4H, m), 3.06-2.90 (2H, m), 2.37-0.86 (27H, m). Signal due to O$\underline{H}$ was not observed.
MS (ESI) m/z: 501 (M+H)$^+$.

Step 2 trans-4-({4-[({4-[(cis-4-Hydroxycyclohexyl)oxy]-1,2-benzisoxazol-3-yl}oxy)methyl]piperidin-1-yl}-methyl)cyclohexanecarboxylic acid The title compound was prepared according to the procedure described in Step 6 of EXAMPLE 1 using methyl trans-4-({4-[({4-[(cis-4-hydroxycyclohexyl)oxy]-1,2-benzisoxazol-3-yl}oxy)methyl]piperidin-1-yl}methyl)cyclohexanecarboxylate (EXAMPLE 44, Step 1) instead of methyl 4-{[4-({[4-(2,2,2-trifluoro-ethoxy)-1,2-benzisoxazol-3-yl]oxy}methyl)piperidin-1-yl]methyl}tetrahydro-2H-pyran-4-carboxylate.
$^1$H-NMR (DMSO-d$_6$) δ: 7.49 (1H, dd, J=8.1, 8.4 Hz), 7.08 (1H, d, J=8.4 Hz), 6.83 (1H, d, J=8.1 Hz), 4.69-4.61 (1H, m), 4.18 (2H, d, J=5.8 Hz), 3.65-3.52 (1H, m), 2.91-2.77 (2H, m), 2.19-1.18 (25H, m), 0.96-0.75 (2H, m).
Signals due to CO$_2$$\underline{H}$ and O$\underline{H}$ were not observed.
MS (ESI) m/z: 473 (M+H)$^+$, 471 (M−H)$^−$.
m.p.: 182.7° C.
IR (KBr) ν: 3447, 2941, 1611 cm$^{-1}$.
Anal. Calcd for C$_{27}$H$_{38}$N$_2$O$_6$·1.2H$_2$O: C, 63.81; H, 8.01; N, 5.51. Found: C, 63.78; H, 7.97; N, 5.48.

Example 45

1-({4-[({4-[(cis-4-Hydroxycyclohexyl)oxy]-1,2-benzisoxazol-3-yl}oxy)methyl]piperidin-1-yl}methyl)-cyclopentanecarboxylic acid Step 1

Methyl 1-({4-[({4-[(cis-4-hydroxycyclohexyl)oxy]-1,2-benzisoxazol-3-yl}oxy)methyl]piperidin-1-yl}-methyl)cyclopentanecarboxylate The title compound was prepared according to the procedure described in Step 3 of EXAMPLE 2 using cis-4-{[3-(piperidin-4-ylmethoxy)-1,2-benzisoxazol-4-yl]oxy}cyclohexanol (EXAMPLE 43, Step 2) and methyl 1-formylcyclopentanecarboxylate (*Synthesis* 1997, 32-34) instead of 3-(piperidin-4-ylmethoxy)-4-(2,2,2-trifluoroethoxy)-1,2-benzisoxazole and methyl 1-formylcyclobutanecarboxylate.
$^1$H-NMR (CDCl$_3$) δ: 7.38 (1H, dd, J=8.1, 8.4 Hz), 6.96 (1H, d, J=8.4 Hz), 6.61 (1H, d, J=8.1 Hz), 4.68-4.58 (1H, m), 4.27 (1H, d, J=4.8 Hz), 3.83-3.65 (4H, m), 2.93-2.79 (2H, m), 2.60 (2H, s), 2.37-0.86 (24H, m).
Signal due to O$\underline{H}$ was not observed.

Step 2

1-({4-[({4-[(cis-4-Hydroxycyclohexyl)oxy]-1,2-benzisoxazol-3-yl}oxy)methyl]piperidin-1-yl}methyl)-cyclopentanecarboxylic acid The title compound was prepared according to the procedure described in Step 6 of EXAMPLE 1 using methyl 1-({4-[({4-[(cis-4-hydroxycyclohexyl)oxy]-1,2-benzisoxazol-3-yl}oxy)methyl]piperidin-1-yl}-methyl)cyclopentanecarboxylate (EXAMPLE 45, Step 1) instead of methyl 4-{[4-({[4-(2,2,2-trifluoro-ethoxy)-1,2-benzisoxazol-3-yl]oxy}methyl)piperidin-1-yl]methyl}tetrahydro-2H-pyran-4-carboxylate.
$^1$H-NMR (DMSO-d$_6$) δ: 7.50 (1H, dd, J=8.0, 8.4 Hz), 7.08 (1H, d, J=8.4 Hz), 6.84 (1H, d, J=8.0 Hz), 4.70-4.61 (1H, m), 4.18 (2H, d, J=5.9 Hz), 3.68-3.49 (1H, m), 3.02-2.87 (2H, m), 2.60 (2H, s), 2.34-2.16 (2H, m), 2.07-1.23 (21H, m).
Signals due to CO$_2$$\underline{H}$ and O$\underline{H}$ were not observed.
MS (ESI) m/z: 473 (M+H)$^+$, 471 (M−H)$^−$.
m.p.: 189.6° C.
IR (KBr) ν: 3422, 2951, 1608 cm$^{-1}$.
Anal. Calcd for C$_{26}$H$_{36}$N$_2$O$_6$: C, 66.08; H, 7.68; N, 5.93. Found: C, 65.98; H, 7.83; N, 5.82.

Example 46

4-[(4-{[(4-{[cis-4-(Hydroxymethyl)cyclohexyl]oxy}-1,2-benzisoxazol-3-yl)oxy]methyl}piperidin-1-yl)-methyl]tetrahydro-2H-pyran-4-carboxylic acid

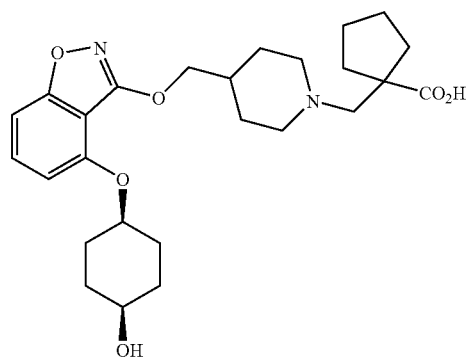 [SMILES: O=C(O)C1(CN2CCC(COc3noc4cccc(O[C@H]5CC[C@@H](O)CC5)c34)CC2)CCCC1]

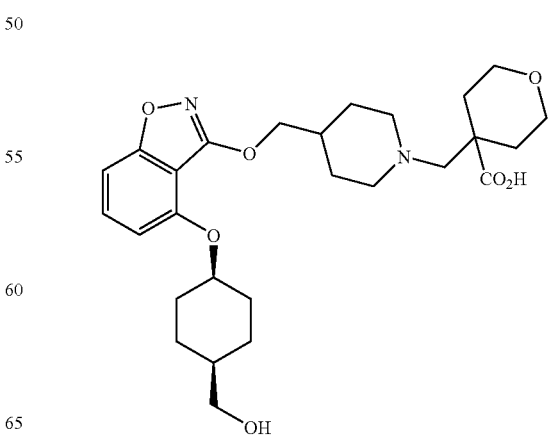

Step 1

(trans-4-Hydroxycyclohexyl)methyl acetate

To a mixture of trans-4-(hydroxymethyl)cyclohexanol (1.8 g, 14 mmol, *Tetrahedron Lett.* 1970, 11, 4281-4284.), triethylamine (2.4 mL, 17 mmol), and N,N-dimethylaminopyridine (0.34 g, 3.0 mmol) in tetrahydrofuran (70 mL) was added acetic anhydride (1.4 mL, 15 mmol) at room temperature. After being stirred at room temperature for 48 h, the mixture was concentrated in vacuo to give an oil. The residual oil was extracted with ethyl acetate (100 mL). The organic layer was washed with successively 2N hydrochloric acid, aq. sodium hydrogencarbonate, and brine. The extract was dried over magnesium sulfate and concentrated in vacuo give an oil. The residual oil was purified by silica gel column chromatography (hexane/ethyl acetate 1:1 to 1:2) to give 1.2 g (50%) the title compound as a colorless oil.

$^1$H-NMR (CDCl$_3$) δ: 3.89 (2H, d, J=6.6 Hz), 3.66-3.50 (1H, m), 2.15-1.95 (5H, m), 1.90-1.75 (2H, m), 1.72-1.46 (1H, m), 1.37-1.18 (2H, m), 1.15-0.95 (2H, m). Signal due to OH was not observed.

Step 2 tert-Butyl 4-({[4-({cis-4-[(acetyloxy)methyl]cyclohexyl}oxy)-1,2-benzisoxazol-3-yl]oxy}methyl)-piperidine-1-carboxylate The title compound was prepared according to the procedure described in Step 2 of EXAMPLE 7 using tert-butyl 4-{[(4-hydroxy-1,2-benzisoxazol-3-yl)oxy]methyl}piperidine-1-carboxylate (EXAMPLE 17, step 2) and (trans-4-hydroxycyclohexyl)methyl acetate (EXAMPLE 46, Step 1) instead of 4-(benzyloxy)-1,2-benzisoxazol-3-ol and tert-butyl 4-(2-hydroxyethyl)piperidine-1-carboxylate.

$^1$H-NMR (CDCl$_3$) δ: 7.38 (1H, dd, J=7.9, 8.3 Hz), 6.96 (1H, d, J=8.3 Hz), 6.59 (1H, d, J=7.9 Hz), 4.78-4.70 (1H, m), 4.31-3.89 (6H, m), 2.86-2.66 (2H, m), 2.21-1.19 (26H, m).

Step 3

(cis-4-{[3-(Piperidin-4-ylmethoxy)-1,2-benzisoxazol-4-yl]oxy}cyclohexyl)methyl acetate The title compound was prepared according to the procedure described in Step 2 of EXAMPLE 2 using tert-butyl 4-({[4-({cis-4-[(acetyloxy)methyl]cyclohexyl}oxy)-1,2-benzisoxazol-3-yl]oxy}methyl)-piperidine-1-carboxylate (EXAMPLE 46, Step 2) instead of ter-butyl 4-({[4-(2,2,2-trifluoroethoxy)-1,2-benzisoxazol-3-yl]oxy}methyl)piperidine-1-carboxylate.

$^1$H-NMR (CDCl$_3$) δ: 7.38 (1H, dd, J=7.9, 8.4 Hz), 6.96 (1H, d, J=8.4 Hz), 6.59 (1H, d, J=7.9 Hz), 4.78-4.70 (1H, m), 4.27 (2H, d, J=6.8 Hz), 3.93 (2H, d, J=7.0 Hz), 3.33-3.22 (2H, m), 2.83-2.68 (2H, m), 2.22-1.37 (17H, m).

Signal due to NH was not observed.

Step 4

Methyl 4-{[4-({[4-({cis-4-[(acetyloxy)methyl]cyclohexyl}oxy)-1,2-benzisoxazol-3-yl]oxy}methyl)-piperidin-1-yl]methyl}tetrahydro-2H-pyran-4-carboxylate The title compound was prepared according to the procedure described in Step 3 of EXAMPLE 2 using (cis-4-{[3-(piperidin-4-ylmethoxy)-1,2-benzisoxazol-4-yl]oxy}cyclohexyl)methyl acetate (EXAMPLE 46, Step 3) and methyl 4-formyltetrahydro-2H-pyran-4-carboxylate (EXAMPLE 18, Step 1) instead of 3-(piperidin-4-ylmethoxy)-4-(2,2,2-trifluoroethoxy)-1,2-benzisoxazole and methyl 1-formylcyclobutanecarboxylate.

$^1$H-NMR (CDCl$_3$) δ: 7.36 (1H, dd, J=7.9, 8.6 Hz), 6.95 (1H, d, J=8.6 Hz), 6.58 (1H, d, J=7.9 Hz), 4.77-4.66 (1H, m), 4.22 (2H, d, J=6.6 Hz), 3.96-3.65 (7H, m), 3.54-3.37 (2H, m), 2.83-2.67 (2H, m), 2.51 (2H, s), 2.30-1.19 (23H, m).

MS (ESI) m/z: 559 (M+H)$^+$.

Step 5

4-[(4-{[(4-{[cis-4-(Hydroxymethyl)cyclohexyl]oxy}-1,2-benzisoxazol-3-yl)oxy]methyl}piperidin-1-yl)methyl]tetrahydro-2H-pyran-4-carboxylic acid The title compound was prepared according to the procedure described in Step 6 of EXAMPLE 1 using methyl 4-{[4-({[4-({cis-4-[(acetyloxy)methyl]cyclohexyl}oxy)-1,2-benzisoxazol-3-yl]oxy}methyl)-piperidin-1-yl]methyl}tetrahydro-2H-pyran-4-carboxylate (EXAMPLE 46, Step 4) instead of methyl 4-({[4-({[4-(2,2,2-trifluoroethoxy)-1,2-benzisoxazol-3-yl]oxy}methyl)piperidin-1-yl]methyl}tetrahydro-2H-pyran-4-carboxylate.

$^1$H-NMR (DMSO-d$_6$) δ: 7.49 (1H, t, J=8.5 Hz), 7.07 (1H, d, J=8.5 Hz), 6.83 (1H, d, J=8.5 Hz), 4.88-4.80 (1H, m), 4.17 (2H, d, J=5.9 Hz), 3.76-3.73 (2H, m), 3.49-3.18 (4H, m), 2.90-2.77 (2H, m), 2.50 (2H, s), 2.30-2.13 (2H, m), 2.04-1.18 (18H, m).

Signals due to CO$_2$H and OH were not observed.

MS (ESI) m/z: 503 (M+H)$^+$, 501 (M−H)$^−$.

m.p.: 197.2° C.

IR (KBr) ν: 3441, 2926, 1610 cm$^{−1}$.

Anal. Calcd for C$_{27}$H$_{38}$N$_2$O$_7$: C, 64.52; H, 7.62; N, 5.57. Found: C, 64.46; H, 7.82; N, 5.46.

Example 47 trans-4-[(4-{[(4-{[cis-4-(Hydroxymethyl)cyclohexyl]oxy}-1,2-benzisoxazol-3-yl)oxy]methyl}-Piperidin-1-yl)methyl]cyclohexanecarboxylic acid

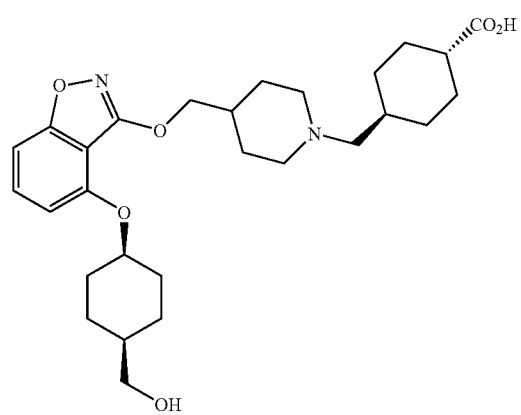 [SMILES: O=C(O)[C@H]1CC[C@H](CN2CCC(COc3noc4cccc(O[C@H]5CC[C@@H](CO)CC5)c34)CC2)CC1]

Step 1

Methyl trans-4-{[4-({[4-({cis-4-[(acetyloxy) Methyl] cyclohexyl}oxy)-1,2-benzisoxazol-3-yl]oxy}-methyl)piperidin-1-yl]methyl}cyclohexanecarboxylate The title compound was prepared according to the procedure described in Step 3 of EXAMPLE 2 using (cis-4-{[3-(piperidin-4-ylmethoxy)-1,2-benzisoxazol-4-yl]oxy}cyclohexyl)methyl acetate (EXAMPLE 46, Step 3) and methyl trans-4-formylcyclohexanecarboxylate (JP 490-48639) instead of 3-(piperidin-4-ylmethoxy)-4-(2,2,2-trifluoroethoxy)-1,2-benzisoxazole and methyl 1-formylcyclobutanecarboxylate.

$^1$H-NMR (CDCl$_3$) δ: 7.37 (1H, dd, J=8.1, 8.3 Hz), 6.96 (1H, d, J=8.3 Hz), 6.59 (1H, d, J=8.1 Hz), 4.78-4.72 (1H, m), 4.25 (2H, d, J=6.4 Hz), 3.92 (2H, d, J=7.0 Hz), 3.70-3.64 (5H, m), 2.94-2.83 (2H, m), 2.33-0.82 (29H, m).

Step 2 trans-4-[(4-{[(4-{[cis-4-(Hydroxymethyl)cyclohexyl]oxy}-1,2-benzisoxazol-3-yl)oxy]methyl}-piperidin-1-yl)methyl]cyclohexanecarboxylic acid The title compound was prepared according to the procedure described in Step 6 of EXAMPLE 1 using methyl trans-4-{[4-({[4-({cis-4-[(acetyloxy)methyl]cyclohexyl}oxy)-1,2-benzisoxazol-3-yl]oxy}methyl)-piperidin-1-yl]methyl}cyclohexanecarboxylate (EXAMPLE 47, Step 1) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

$^1$H-NMR (DMSO-d$_6$) δ: 7.51 (1H, dd, J=7.9, 8.6 Hz), 7.08 (1H, d, J=8.6 Hz), 6.84 (1H, d, J=7.9 Hz), 4.89-4.81 (1H, m), 4.28-4.14 (2H, m), 3.24 (2H, d, J=5.3 Hz), 2.20-0.80 (30H, m).
Signals due to CO$_2$H and OH were not observed.
MS (ESI) m/z: 501 (M+H)$^+$, 499 (M−H)$^−$.
IR (KBr) ν: 3386, 2934, 1612, 1083 cm$^{-1}$.
Anal. Calcd for C$_{28}$H$_{40}$N$_2$O$_6$·2H$_2$O: C, 62.67; H, 8.26; N, 5.22. Found: C, 62.75; H, 7.94; N, 5.09.

Example 48

1-[(4-{[(4-{[cis-4-(Hydroxymethyl)cyclohexyl]oxy}-1,2-benzisoxazol-3-yl)oxy]methyl}piperidin-1-yl) methyl]cyclopentanecarboxylic acid

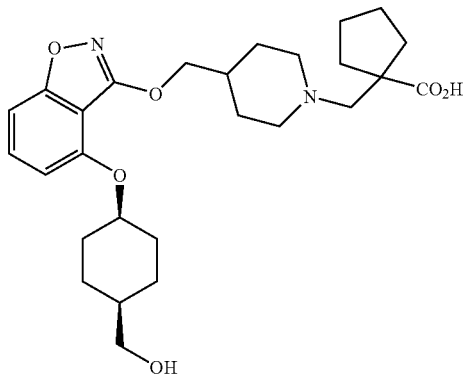 [SMILES: O=C(O)C1(CN2CCC(COc3noc4cccc(O[C@H]5CC[C@@H](CO)CC5)c34)CC2)CCCC1]

Step 1

Methyl 1-{[4-({[4-({cis-4-[(acetyloxy)methyl] cyclohexyl}oxy)-1,2-benzisoxazol-3-yl]oxy}methyl)-piperidin-1-yl]methyl}cyclopentanecarboxylate The title compound was prepared according to the procedure described in Step 3 of EXAMPLE 2 using (cis-4-{[3-(piperidin-4-ylmethoxy)-1,2-benzisoxazol-4-yl]oxy}cyclohexyl)methyl acetate (EXAMPLE 46, Step 3) and methyl 1-formylcyclopentanecarboxylate (Synthesis 1997, 32-34) instead of 3-(piperidin-4-ylmethoxy)-4-(2,2,2-trifluoroethoxy)-1,2-benzisoxazole and methyl 1-formylcyclobutanecarboxylate.

$^1$H-NMR (CDCl$_3$) δ: 7.37 (1H, t, J=7.9 Hz), 6.96 (1H, d, J=7.9 Hz), 6.59 (1H, d, J=7.9 Hz), 4.77-4.70 (1H, m), 4.22 (2H, d, J=6.6 Hz), 3.92 (2H, d, J=6.6 Hz), 3.67 (3H, s), 3.57 (2H, d, J=6.6 Hz), 2.88-2.77 (2H, m), 2.58 (2H, s), 2.21-1.23 (25H, m).

Step 2

1-[(4-{[(4-{[cis-4-(Hydroxymethyl)cyclohexyl]oxy}-1,2-benzisoxazol-3-yl)oxy]methyl}piperidin-1-yl)methyl]cyclopentanecarboxylic acid The title compound was prepared according to the procedure described in Step 6 of EXAMPLE 1 using methyl 1-{[4-({[4-({cis-4-[(acetyloxy)methyl]cyclohexyl}oxy)-1,2-benzisoxazol-3-yl]oxy}methyl)-piperidin-1-yl]methyl}cyclopentanecarboxylate (EXAMPLE 48, Step 1) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

$^1$H-NMR (DMSO-d$_6$) δ: 7.50 (1H, t, J=8.6 Hz), 7.07 (1H, d, J=8.6 Hz), 6.83 (1H, d, J=8.5 Hz), 4.88-4.80 (1H, m), 4.18 (2H, d, J=5.9 Hz), 3.24 (2H, d, J=6.6 Hz), 2.99-2.87 (2H, m), 2.60 (2H, s), 2.27-2.12 (2H, m), 2.04-1.20 (22H, m).
Signals due to CO$_2$H and OH were not observed.
MS (ESI) m/z: 487 (M+H)$^+$, 485 (M−H)$^−$.
m.p.: 188.0° C.
IR (KBr) ν: 3318, 2937, 1613 cm$^{-1}$.
Anal. Calcd for C$_{27}$H$_{38}$N$_2$O$_6$: C, 66.64; H, 7.87; N, 5.76. Found: C, 66.82; H, 8.04; N, 5.77.

Example 49

4-[(4-{[(4-{[1-(Hydroxymethyl)cyclobutyl]methoxy}-1,2-benzisoxazol-3-VI)oxy]methyl}piperidin-1-yl)methyl]tetrahydro-2H-pyran-4-carboxylic acid

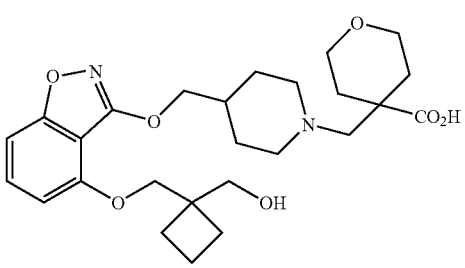 [SMILES: O=C(O)C1(CN2CCC(COc3noc4cccc(OCC5(CO)CCC5)c34)CC2)CCOCC1]

Step 1 tert-Butyl 4-{[(4-{[1-(hydroxymethyl)cyclobutyl]
methoxy}-1,2-benzisoxazol-3-yl)oxy]methyl}-piperidine-1-carboxylate The title compound was prepared according to the procedure described in Step 4 of EXAMPLE 9 using tert-butyl 4-{[(4-hydroxy-1,2-benzisoxazol-3-yl)oxy] methyl}piperidine-1-carboxylate (EXAMPLE 17, Step 2) and cyclobutane-1,1-diyldimethanol (DE 19735574) instead of 4-[(4-methoxybenzyl)oxy]-1,2-benzisoxazol-3-ol and methyl 1-{[4-(hydroxymethyl)piperidin-1-yl] methyl}cyclopentanecarboxylate.

$^1$H-NMR (CDCl$_3$) δ: 7.42 (1H, t, J=8.4 Hz), 7.01 (1H, d, J=8.4 Hz), 6.62 (1H, d, J=8.4 Hz), 4.26 (2H, d, J=6.6 Hz), 4.21 (2H, d, J=6.4 Hz), 4.15 (2H, s), 3.79 (2H, d, J=3.9 Hz), 2.87-2.68 (2H, m), 2.65-2.50 (1H, m), 2.05-1.93 (6H, m), 1.90-1.68 (4H, m), 1.47 (9H, s).

A signal due to O$\underline{H}$ was not obserbed.

Step 2

[1-({[3-(Piperidin-4-ylmethoxy)-1,2-benzisoxazol-4-yl]oxy}methyl)cyclobutyl]methanol The title compound was prepared according to the procedure described in Step 2 of EXAMPLE 2 using tert-butyl 4-{[(4-{[1-(hydroxymethyl)cyclobutyl]methoxy}-1,2-benzisoxazol-3-yl)oxy]methyl}-piperidine-1-carboxylate (EXAMPLE 49, Step 1) instead of tert-butyl 4-({[4-(2,2,2-trifluoroethoxy)-1,2-benzisoxazol-3-yl]oxy}methyl) piperidine-1-carboxylate.

$^1$H-NMR (CDCl$_3$) δ: 7.41 (1H, t, J=8.2 Hz), 6.98 (1H, d, J=8.2 Hz), 6.59 (1H, d, J=8.2 Hz), 4.28 (2H, d, J=3.1 Hz), 4.11 (2H, s), 3.77 (2H, s), 3.22-3.12 (2H, m), 2.74-2.60 (2H, m), 2.34-2.15 (2H, m), 2.03-1.60 (9H, m).

Signals due to N$\underline{H}$ and O$\underline{H}$ were not observed.
MS (ESI) m/z: 347 (M+H)$^+$.

Step 3

Methyl 4-[(4-{[(4-{[1-(hydroxymethyl)cyclobutyl]
methoxy}-1,2-benzisoxazol-3-yl)oxy]methyl}-piperidin-1-yl)methyl]tetrahydro-2H-pyran-4-carboxylate The title compound was prepared according to the procedure described in Step 3 of EXAMPLE 2 using [1-({[3-(piperidin-4-ylmethoxy)-1,2-benzisoxazol-4-yl] oxy}methyl)cyclobutyl]methanol (EXAMPLE 49, Step 2) and methyl 4-formyltetrahydro-2H-pyran-4-carboxylate (EXAMPLE 18, Step 1) instead of 3-(piperidin-4-ylmethoxy)-4-(2,2,2-trifluoroethoxy)-1,2-benzisoxazole and methyl 1-formylcyclobutane-carboxylate.

$^1$H-NMR (CDCl$_3$) δ: 7.41 (1H, t, J=8.2 Hz), 7.00 (1H, d, J=8.2 Hz), 6.61 (1H, d, J=8.2 Hz), 4.23 (2H, d, J=6.3 Hz), 4.14 (2H, s), 3.90-3.76 (6H, m), 3.72 (2H, s), 3.61-3.40 (2H, m), 2.84-2.71 (2H, m), 2.67-2.43 (1H, brs), 2.51 (2H, s), 2.32-2.13 (2H, m), 2.14-1.93 (9H, m), 1.90-1.50 (2H, m), 1.50-1.30 (2H, m).

A signal due to O$\underline{H}$ was not observed.
MS (ESI) m/z: 503 (M+H)$^+$.

Step 4

4-[(4-{[(4-{[1-(Hydroxymethyl)cyclobutyl]methoxy}-1,2-benzisoxazol-3-yl)oxy]methyl}piperidin-1-yl)methyl]tetrahydro-2H-pyran-4-carboxylic acid The title compound was prepared according to the procedure described in Step 6 of EXAMPLE 1 using methyl 4-[(4-{[(4-{[1-(hydroxymethyl)cyclobutyl]methoxy}-1,2-benzisoxazol-3-yl)oxy]methyl}-piperidin-1-yl)methyl] tetrahydro-2H-pyran-4-carboxylate (EXAMPLE 49, Step 3) instead of methyl 4-{[4-({[4-(2,2,2-trifluoroethoxy)-1,2-benzisoxazol-3-yl]oxy}methyl)piperidin-1-yl] methyl}tetrahydro-2H-pyran-4-carboxylate.

$^1$H-NMR (CDCl$_3$) δ: 7.44 (1H, t, J=8.2 Hz), 7.03 (1H, d, J=8.2 Hz), 6.62 (1H, d, J=8.2 Hz), 4.29 (2H, d, J=6.4 Hz), 4.17 (2H, s), 3.95-3.77 (4H, m), 3.79 (2H, s), 3.22-3.11 (2H, m), 2.65-2.53 (2H, m), 2.61 (2H, s), 2.10-1.90 (11H, m), 1.70-1.39 (4H, m).

Signals due to O$\underline{H}$ and CO$_2$$\underline{H}$ were not observed.
MS (ESI) m/z: 489 (M+H)$^+$, 487 (M−H)$^-$.
IR (KBr) ν: 3420, 2937, 2856, 1614, 1531, 1433, 1369, 1346, 1279, 1097, 785 cm$^{-1}$
Anal. Calcd for C$_{26}$H$_{36}$N$_2$O$_7$.0.6H$_2$O: C, 62.53; H, 7.51; N, 5.61. Found: C, 62.35; H, 7.89; N, 5.44.

Example 50

1-[(4-{[(4-{[(1-(Hydroxymethyl)cyclobutyl]methoxy}-1,2-benzisoxazol-3-yl)oxy]methyl}piperidin-1-yl)methyl]cyclobutanecarboxylic acid

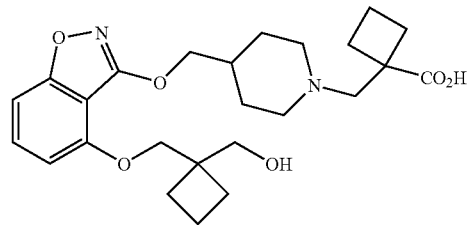 [SMILES: O=C(O)C1(CN2CCC(COc3noc4cccc(OCC5(CO)CCC5)c34)CC2)CCC1]

Step 1

Methyl 1-[(4-{[(4-{[1-(hydroxymethyl)cyclobutyl]
methoxy}-1,2-benzisoxazol-3-yl)oxy]methyl}-piperidin-1-yl)methyl]cyclobutanecarboxylate The title compound was prepared according to the procedure described in Step 3 of EXAMPLE 2 using [1-({[3-(piperidin-4-ylmethoxy)-1,2-benzisoxazol-4-yl] oxy}methyl)cyclobutyl]methanol (EXAMPLE 49, Step 2) instead of 3-(piperidin-4-ylmethoxy)-4-(2,2,2-trifluoroethoxy)-1,2-benzisoxazole.

$^1$H-NMR (CDCl$_3$) δ: 7.41 (1H, t, J=8.6 Hz), 7.00 (1H, d, J=8.6 Hz), 6.60 (1H, d, J=8.6 Hz), 4.23 (2H, d, J=5.6 Hz), 4.13 (2H, s), 3.79 (2H, s), 3.72 (3H, s), 2.90-2.77 (2H, m), 2.75 (2H, s), 2.51-2.38 (2H, m), 2.20-1.65 (15H, m), 1.55-1.34 (2H, m).

A signal due to O$\underline{H}$ was not observed.
MS (ESI) m/z: 473 (M+H)$^+$.

Step 2

1-[(4-{[(4-{[1-(Hydroxymethyl)cyclobutyl]methoxy}-1,2-benzisoxazol-3-yl)oxy]methyl}piperidin-1-yl)methyl]cyclobutanecarboxylic acid The title compound was prepared according to the procedure described in Step 6 of EXAMPLE 1 using methyl 1-[(4-{[(4-{[1-(hydroxymethyl)cyclobutyl]methoxy}-1,2-benzisoxazol-3-yl)oxy]methyl}-piperidin-1-yl)methyl]cyclobutanecarboxylate (EXAMPLE 50, Step 1) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

$^1$H-NMR (CDCl$_3$) δ: 7.43 (1H, t, J=8.3 Hz), 7.02 (1H, d, J=8.3 Hz), 6.62 (1H, d, J=8.3 Hz), 4.28 (2H, d, J=6.4 Hz), 4.16 (2H, s), 3.80 (2H, s), 3.15-3.02 (2H, m), 2.80 (2H, s), 2.61-2.20 (5H, m), 2.08-1.80 (12H, m), 1.65-1.43 (2H, m).

Signals due to CO$_2$H and OH were not observed.

MS (ESI) m/z: 459 (M+H)$^+$, 457 (M−H)$^−$.

m.p.: 194.2° C.

IR (KBr) ν: 3329, 2939, 1614, 1531, 1433, 1369, 1344, 1286, 1096, 791 cm$^{-1}$

Anal. Calcd for C$_{25}$H$_{34}$N$_2$O$_6$·0.1H$_2$O: C, 65.23; H, 7.49; N, 6.09. Found: C, 64.98; H, 7.37; N, 5.98.

Example 51

4-[(4-{[(4-{[1-(Hydroxymethyl)cyclopentyl]methoxy}-1,2-benzisoxazole-3-yl)oxy]methyl}piperidin-1-yl)methyl]tetrahydro-2H-pyran-4-carboxylic acid

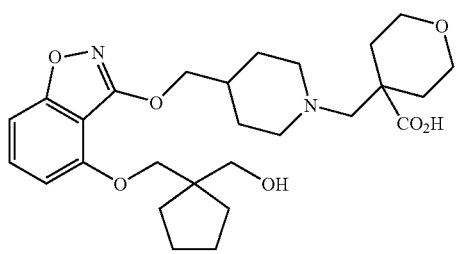 [SMILES: O=C(O)C1(CN2CCC(COc3noc4cccc(OCC5(CO)CCCC5)c34)CC2)CCOCC1]

Step 1

Methyl 1-(hydroxymethyl)cyclopentanecarboxylate

To a solution of methyl 1-formylcyclopentanecarboxylate (954 mg, 6.11 mmol, *Synthesis* 1997, 32-34) in ethanol (10 mL) was added sodium tetrahydroborate (104 mg, 2.75 mmol) at ambient temperature. After being stirred for 30 min, the mixture was concentrated in vacuo to give an oil. The residual oil was dissolved with ethyl acetate, and the solution was washed with brine. The extract was dried over magnesium sulfate and concentrated in vacuo to afford 806 mg (83%) of the title compound as a colorless oil. The crude product was used in the next step without further purification.

$^1$H-NMR (CDCl$_3$) δ: 3.72 (3H, s), 3.58 (2H, d, J=6.8 Hz), 2.55 (1H, t, J=6.8 Hz), 2.00 (2H, m), 1.77-1.59 (6H, m). TLC (silica gel, ethyl acetate/hexane=1:2) Rf: 0.24.

Step 2 tert-Butyl 4-{[(4-{[1-(methoxycarbonyl)cyclopentyl]methoxy}-1,2-benzisoxazol-3-yl)oxy]methyl}-piperidine-1-carboxylate The title compound was prepared according to the procedure described in Step 2 of EXAMPLE 7 using tert-butyl 4-{[(4-hydroxy-1,2-benzisoxazol-3-yl)oxy]methyl}piperidine-1-carboxylate (EXAMPLE 17, step 2) and methyl 1-(hydroxymethyl)cyclopentanecarboxylate (EXAMPLE 51, Step 1) instead of 4-(benzyloxy)-1,2-benzisoxazol-3-ol and tert-butyl 4-(2-hydroxyethyl)piperidine-1-carboxylate.

$^1$H-NMR (CDCl$_3$) δ: 7.39 (1H, t, J=8.2 Hz), 6.99 (1H, d, J=8.4 Hz), 6.59 (1H, d, J=7.9 Hz), 4.22 (2H, d, J=6.6 Hz), 4.18 (2H, m), 4.16 (2H, s), 3.69 (3H, s), 2.79 (2H, t, J=12.3 Hz), 2.13 (2H, m), 1.86-1.60 (9H, m), 1.47 (9H, s), 1.30 (2H, m).

TLC (silica gel, ethyl acetate/hexane=1:2) Rf: 0.54.

Step 3 tert-Butyl 4-{[(4-{[1-(hydroxymethyl)cyclopentyl]methoxy}-1,2-benzisoxazol-3-yl)oxy]methyl}-piperidine-1-carboxylate To a suspension of lithium aluminum hydride (50.7 mg, 1.34 mmol) in diethyl ether (5 mL) was added an ethereal solution (3 mL) of tert-butyl 4-{[(4-{[1-(methoxycarbonyl)cyclopentyl]methoxy}-1,2-benzisoxazol-3-yl)oxy]methyl}piperidine-1-carboxylate (EXAMPLE 51, step 2, 600 mg, 1.23 mmol) at 0° C. After being stirred for 30 min, ethyl acetate was added to the mixture. Then the mixture was washed with 2N hydrochloric acid and brine. The organic layer was dried over magnesium sulfate and concentrated in vacuo to afford 456 mg (81%) of the title compound as a white solid. The crude product was used in the next step without further purification.

$^1$H-NMR (CDCl$_3$) δ: 7.41 (1H, t, J=8.2 Hz), 7.01 (1H, d, J=8.6 Hz), 6.59 (1H, d, J=7.9 Hz), 4.27 (2H, d, J=6.6 Hz), 4.16 (2H, m), 4.00 (2H, s), 3.61 (2H, s), 2.74 (2H, t, J=12.4 Hz), 2.09 (1H, m), 1.85 (2H, d, J=13.9 Hz), 1.82-1.23 (19H, m). A signal due to OH was not observed.

TLC (silica gel, ethyl acetate/hexane=1:2) Rf: 0.26.

Step 4

[1-({[3-(Piperidin-4-ylmethoxy)-1,2-benzisoxazol-4-yl]oxy}methyl)cyclopentyl]methanol The title compound was prepared according to the procedure described in Step 2 of EXAMPLE 2 using tert-Butyl 4-{[(4-{[1-(hydroxymethyl)cyclopentyl]methoxy}-1,2-benzisoxazol-3-yl)oxy]methyl}-piperidine-1-carboxylate (EXAMPLE 51, Step 3) instead of tert-butyl 4-({[4-(2,2,2-trifluoroethoxy)-1,2-benzisoxazol-3-yl]oxy}methyl)piperidine-1-carboxylate.

$^1$H-NMR (CDCl$_3$) δ: 7.39 (1H, t, J=8.1 Hz), 6.78 (1H, d, J=8.6 Hz), 6.56 (1H, d, J=7.9 Hz), 4.28 (2H, d, J=4.1 Hz), 3.90 (2H, s), 3.79 (2H, d, J=1.6 Hz), 3.52 (1H, br), 3.14 (2H, d, J=11.5 Hz), 2.65 (2H, m), 1.95 (1H, m), 1.81-1.43 (m, 12H). A signal due to NH was not observed.

MS (ESI) m/z: 361 (M+H)$^+$.

Step 5

Methyl 4-[(4-{[(4-{[1-(hydroxymethyl)cyclopentyl]methoxy}-1,2-benzisoxazol-3-yl)oxy]methyl}-piperidin-1-yl)methyl]tetrahydro-2H-pyran-4-carboxylate The title compound was prepared according to the procedure described in Step 3 of EXAMPLE 2 using [1-({[3-(Piperidin-4-ylmethoxy)-1,2-benzisoxazol-4-yl]oxy}methyl)cyclopentyl]methanol (EXAMPLE 51, Step 4) and methyl 4-formyltetrahydro-2H-pyran-4-carboxylate (EXAMPLE 18, Step 1) instead of 3-(piperidin-4-ylmethoxy)-4-(2,2,2-trifluoroethoxy)-1,2-benzisoxazole and methyl 1-formylcyclobutane-carboxylate.

$^1$H-NMR (CDCl$_3$) δ: 7.40 (1H, t, J=8.2 Hz), 7.00 (1H, d, J=8.4 Hz), 6.59 (1H, d, J=8.1 Hz), 4.24 (2H, d, J=6.3 Hz), 3.99 (2H, s), 3.83 (2H, m), 3.77 (2H, s), 3.71 (3H, s), 3.47 (2H, m), 2.75 (2H, m), 2.51 (2H, s), 2.25 (2H, t, J=11.6 Hz), 2.02 (2H, m), 1.88-1.40 (15H, m).

A signal due to O$\underline{H}$ was not observed.

TLC (silica gel, ethyl acetate/hexane 1:2) Rf: 0.08.
TLC (NH gel, ethyl acetate/hexane 1:1) Rf: 0.47.

Step 6

4-[(4-{[(4-{[1-(Hydroxymethyl)cyclopentyl]methoxy}-1,2-benzisoxazol-3-yl)oxy]methyl}-piperidin-1-yl)methyl]tetrahydro-2H-pyran-4-carboxylic acid The title compound was prepared according to the procedure described in Step 6 of EXAMPLE 1 using methyl 4-[(4-{[(4-{[1-(hydroxymethyl)cyclopentyl]methoxy}-1,2-benzisoxazol-3-yl)oxy]methyl}-piperidin-1-yl)methyl]tetrahydro-2H-pyran-4-carboxylate (EXAMPLE 51, Step 5) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

$^1$H-NMR (CDCl$_3$) δ: 7.40 (1H, t, J=8.2 Hz), 6.99 (1H, d, J=8.4 Hz), 6.58 (1H, d, J=7.9 Hz), 4.27 (2H, d, J=5.6 Hz), 3.97 (2H, s), 3.74 (4H, m), 3.65 (2H, s), 3.07 (2H, d, J=10.7 Hz), 2.54 (2H, s), 2.43 (2H, t, J=10.9 Hz), 1.95 (2H, d, J=12.7 Hz), 1.85 (2H, d, J=13.5 Hz), 1.66-1.45 (13H, m).

Two signals due to O$\underline{H}$ and CO$_2$ were not observed.

MS (ESI) m/z: 503 (M+H)$^+$, 501 (M–H)$^-$.

IR (KBr) ν: 3358, 2949, 1614, 1533, 1433, 1096 cm$^{-1}$.

Anal. Calcd for C$_{27}$H$_{38}$N$_2$O$_7$·1.5H$_2$O: C, 61.23; H, 7.80; N, 5.29. Found: C, 61.17; H, 7.75; N, 4.98.

Example 52

1-[(4-{[(4-{[1-(Hydroxymethyl)cyclopentyl]methoxy}-1,2-benzisoxazol-3-yl)oxy]methyl}piperidin-1-yl)methyl]cyclobutanecarboxylic acid

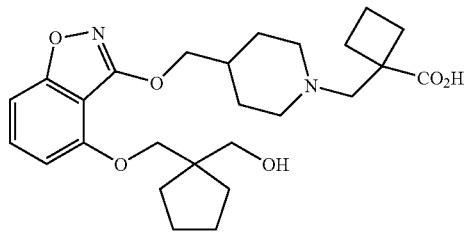 [SMILES: O=C(O)C1(CN2CCC(COc3noc4cccc(OCC5(CO)CCCC5)c34)CC2)CCC1]

Step 1

Methyl 1-[(4-{[(4-{[1-(hydroxymethyl)cyclopentyl]methoxy}-1,2-benzisoxazol-3-yl)oxy]methyl}-piperidin-1-yl)methyl]cyclobutanecarxobxylate The title compound was prepared according to the procedure described in Step 3 of EXAMPLE 2 using [1-({[3-(Piperidin-4-ylmethoxy)-1,2-benzisoxazol-4-yl]oxy}methyl)cyclopentyl]methanol (EXAMPLE 51, Step 4) instead of 3-(piperidin-4-ylmethoxy)-4-(2,2,2-trifluoroethoxy)-1,2-benzisoxazole.

$^1$H-NMR (CDCl$_3$) δ: 7.39 (1H, t, J=8.2 Hz), 6.99 (1H, d, J=8.6 Hz), 6.58 (1H, d, J=7.9 Hz), 4.23 (2H, d, J=6.1 Hz), 3.97 (2H, s), 3.75 (2H, s), 3.71 (3H, s), 2.81 (2H, d, J=11.2 Hz), 2.72 (2H, s), 2.43 (4H, m), 2.06-1.39 (17H, m).

A signal due to O$\underline{H}$ was not observed.

TLC (NH gel, ethyl acetate/hexane 1:1) Rf: 0.57.

Step 2

1-[(4-{[(4-{[1-(Hydroxymethyl)cyclopentyl]methoxy}-1,2-benzisoxazol)-3-yl]oxy}methyl)-piperidin-1-yl]methyl]cycylobutanecarboxylic acid The title compound was prepared according to the procedure described in Step 6 of EXAMPLE 1 using methyl 1-[(4-{[(4-{[1-(hydroxymethyl)cyclopentyl]methoxy}-1,2-benzisoxazol-3-yl)oxy]methyl}-piperidin-1-yl)methyl]cyclobutanecarxobxylate (EXAMPLE 52, Step 1) instead of methyl 4-{[4-({[4-(2,2,2-trifluoroethoxy)-1,2-benzisoxazol-3-yl]oxy}methyl)piperidin-1-yl]methyl}tetrahydro-2H-pyran-4-carboxylate.

$^1$H-NMR (CDCl$_3$) δ: 7.42 (1H, t, J=8.3 Hz), 7.02 (1H, d, J=8.4 Hz), 6.60 (1H, d, J=7.9 Hz), 4.29 (2H, d, J=6.4 Hz), 4.00 (2H, s), 3.65 (2H, s), 3.07 (2H, d, J=10.7 Hz), 2.80 (2H, s), 2.80-2.25 (6H, m), 2.10-1.93 (5H, m), 1.69-1.55 (10H, m).

Two signals due to O$\underline{H}$ and CO$_2\underline{H}$ were not observed.

MS (ESI) m/z: 473 (M+H)$^+$, 471 (M–H)$^-$.

IR (KBr) ν: 3302, 2945, 1622, 1611, 1568, 1533, 1431, 1094 cm$^{-1}$.

Anal. Calcd for C$_{26}$H$_{36}$N$_2$O$_6$H$_2$O: C, 63.65; H, 7.81; N, 5.71. Found: C, 63.38; H, 7.79; N, 5.63.

Example 53

4-{[4-({[4-(2,2,2-Trifluoroethoxy)-1,2-benzisoxazol-3-yl]amino}methyl)piperidin-1-yl]methyl}-tetrahydro-2H-pyran-4-carboxylic acid

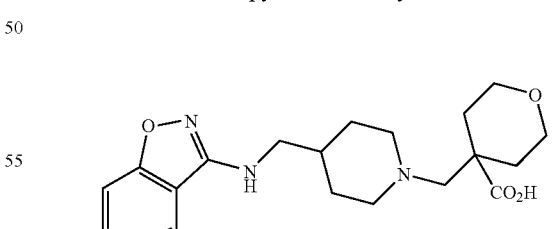

Step 1

2-Fluoro-6-(2,2,2-trifluoroethoxy)benzaldehyde

To a suspension of 2-fluoro-6-(2,2,2-trifluoroethoxy)benzonitrile (2.3 g, 11 mmol, *J. Heteloyclic Chem.* 1988, 25, 1173-1177) in toluene (40 mL) was added diisobutylaluminium hydride (1.0 M in toluene, 11 mL, 11 mmol) at −78° C. The mixture was warmed to room temperature and stirred for 16 h. Methanol (3.0 mL) was added to the mixture and the mixture was stirred for 10 min, then 2N hydrochloric acid (6.0 mL) was added to the mixture. After being stirred at room temperature for 1 h, the mixture was extracted with ethyl acetate (50 mL×2) and washed with aq. sodium hydrogencarbonate. The combined extracts were dried over magnesium sulfate and concentrated in vacuo to give a solid. The residual solid was purified by silica gel column chromatography (hexane/ethyl acetate 4:1) to afford 2.2 g (94%) of the title compound as a white solid.

$^1$H-NMR (CDCl$_3$) δ: 10.45 (1H, s), 7.60-7.45 (1H, m), 6.95-6.71 (2H, m), 4.48 (2H, q, J=7.9 Hz).

Step 2

2-Fluoro-6-(2,2,2-trifluoroethoxy)benzaldehyde oxime

The title compound was prepared according to the procedure described in Step 3 of EXAMPLE 16 using 2-fluoro-6-(2,2,2-trifluoroethoxy)benzaldehyde (EXAMPLE 53, Step 1) instead of 2-fluoro-6-isobutoxybenzaldehyde.

$^1$H-NMR (CDCl$_3$) δ: 9.15 (1H, s), 8.43 (1H, s), 7.39-7.28 (1H, m), 6.94-6.84 (1H, m), 6.72 (1H, d, J=7.9 Hz), 4.43 (2H, q, J=7.9 Hz).

Step 3

2-Fluoro-N-hydroxy-6-(2,2,2-trifluoroethoxy)benzenecarboximidoyl chloride

The title compound was prepared according to the procedure described in Step 4 of EXAMPLE 16 using 2-fluoro-6-(2,2,2-trifluoroethoxy)benzaldehyde oxime (EXAMPLE 53, Step 2) instead of 2-fluoro-6-isobutoxybenzaldehyde oxime.

$^1$H-NMR (CDCl$_3$) δ: 8.27 (1H, br), 7.49-7.39 (1H, m), 6.95-6.85 (1H, m), 6.75 (1H, d, J=8.6 Hz), 4.52-4.36 (2H, m).

Step 4

Methyl 4-{[4-({[[2-fluoro-6-(2,2,2-trifluoroethoxy)phenyl](hydroxyimino)methyl]amino}methyl)-piperidin-1-yl]methyl}tetrahydro-2H-pyran-4-carboxylate The title compound was prepared according to the procedure described in Step 8 of EXAMPLE 16 using 2-fluoro-N-hydroxy-6-(2,2,2-trifluoroethoxy)benzenecarboximidoyl chloride (EXAMPLE 53, Step 3) instead of 2-fluoro-N-hydroxy-6-isobutoxybenzenecarboximidoyl chloride.

$^1$H-NMR (CDCl$_3$) δ: 7.44-7.32 (1H, m), 6.88 (1H, d, J=8.6 Hz), 6.76 (1H, d, J=8.6 Hz), 5.44-5.33 (1H, m), 4.41 (2H, q, J=7.9 Hz), 3.85-3.74 (2H, m), 3.68 (3H, s), 3.51-3.77 (2H, m), 2.76-2.60 (4H, m), 2.45 (2H, s), 2.16-1.96 (4H, m), 1.62-1.46 (4H, m), 1.35-0.94 (3H, m).

Signal due to OH was not observed.
MS (ESI) m/z: 506 (M+H)$^+$.

Step 5

Methyl 4-{[4-({[4-(2,2,2-trifluoroethoxy)-1,2-benzisoxazol-3-yl]amino}methyl)piperidin-1-yl]methyl}-tetrahydro-2H-pyran-4-carboxylate The title compound was prepared according to the procedure described in Step 9 of EXAMPLE 16 using methyl 4-{[4-({[[2-fluoro-6-(2,2,2-trifluoroethoxy)phenyl](hydroxyimino)methyl]amino}methyl)-piperidin-1-yl]methyl}tetrahydro-2H-pyran-4-carboxylate (EXAMPLE 53, Step 4) instead of methyl 4-{[4-({[(2-fluoro-6-isobutoxyphenyl)(hydroxyimino)methyl]amino}methyl)piperidin-1-yl]methyl}tetrahydro-2H-pyran-4-carboxylate.

$^1$H-NMR (CDCl$_3$) δ: 7.38 (1H, dd, J=7.9, 8.6 Hz), 7.06 (1H, d, J=8.6 Hz), 6.50 (1H, d, J=7.9 Hz), 4.94-4.84 (1H, m), 4.51 (2H, q, J=7.9 Hz), 3.87-3.76 (2H, m), 3.71 (3H, m), 3.53-3.39 (2H, m), 3.25 (2H, t, J=5.9 Hz), 2.80-2.69 (2H, m), 2.50 (2H, s), 2.27-2.14 (2H, m), 2.10-2.00 (2H, m), 1.75-1.20 (7H, m).

MS (ESI) m/z: 486 (M+H)$^+$.

Step 6

4-{[4-({[4-(2,2,2-Trifluoroethoxy)-1,2-benzisoxazol-3-yl]amino}methyl)piperidin-1-yl]methyl}-tetrahydro-2H-pyran-4-carboxylic acid The title compound was prepared according to the procedure described in Step 7 of EXAMPLE 9 using methyl 4-{[4-({[4-(2,2,2-trifluoroethoxy)-1,2-benzisoxazol-3-yl]amino}methyl)piperidin-1-yl]methyl}-tetrahydro-2H-pyran-4-carboxylate (EXAMPLE 53, Step 5) instead of methyl 1-[(4-{[(4-isobutoxy-1,2-benzisoxazol-3-yl)oxy]methyl}piperidin-1-yl)methyl]cyclopentanecarboxylate.

$^1$H-NMR (DMSO-d$_6$) δ: 7.50 (1H, t, J=8.1 Hz), 7.13 (1H, d, J=8.1 Hz), 6.91 (1H, d, J=8.1 Hz), 5.44 (1H, t, J=5.9 Hz), 5.00 (2H, q, J=8.8 Hz), 3.75-3.62 (2H, m), 3.47-3.30 (2H, m), 3.20-3.10 (2H, m), 2.87-2.76 (2H, m), 2.49 (2H, s), 2.25-2.11 (2H, m), 1.93-1.11 (9H, m).

A signal due to CO$_2$H was not observed.
MS (ESI) m/z: 472 (M+H)$^+$, 470 (M−H)$^-$.
m.p.: 171.9° C.
IR (KBr) ν: 3431, 2951, 1618, 1162, 1118 cm$^{-1}$.
Anal. Calcd for C$_{22}$H$_{28}$N$_3$O$_5$F$_3$·H$_2$O: C, 53.98; H, 6.18; N, 8.58. Found: C, 54.25; H, 6.17; N, 8.59.

All publications, including but not limited to, issued patents, patent applications, and journal articles, cited in this application are each herein incorporated by reference in their entirety.

Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:
1. A compound of formula I

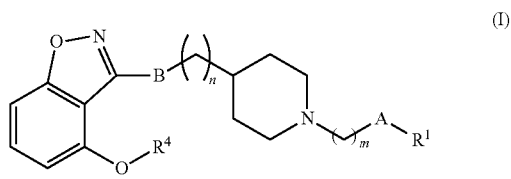

wherein:
A is —C(R$^2$)(R$^3$)— or C$^3$-C$^6$ cycloalkylene; said C$_3$-C$_6$ cycloalkylene being optionally substituted with 1 to 4 substituents independently selected from halogen, hydroxy, C$_1$-C$_4$ alkyl, or C$_1$-C$_4$ alkoxy;
B is —O— or —N(H)—;

$R^1$ is carboxy or hydroxy;
$R^2$ and $R^3$ are independently halogen or $C_1$-$C_4$ alkyl; said $C_1$-$C_4$ alkyl optionally substituted with 1 to 4 substituents independently selected from halogen, hydroxy, or $C_1$-$C_4$ alkoxy; or $R^2$ and $R^3$, together with the atom to which they are attached, form a $C_3$-$C_6$ cycloalkyl or a 6-membered heterocyclic ring containing one heteroatom selected from O or S being optionally substituted with 1 to 4 substituents independently selected from halogen, hydroxy, $C_1$-$C_4$ alkyl, or $C_1$-$C_4$ alkoxy;
$R^4$ is $C_4$-$C_6$ cycloalkyl, a 3 to 6-membered heterocyclic ring containing one heteroatom selected from O or N, or —$CH_2$—$R^5$; said $C_4$-$C_6$ cycloalkyl being optionally substituted with 1 to 4 substituents independently selected from hydroxy, oxo, or $C_1$-$C_4$ alkoxy;
$R^5$ is trifluoromethyl, isopropyl, or $C_4$-$C_6$ cycloalkyl; said $C_4$-$C_6$ cycloalkyl being optionally substituted with 1 to 4 substituents independently selected from hydroxy, oxo, $C_1$-$C_4$ alkoxy, or hydroxyl-$C_1$-$C_4$ alkyl;
m is 1 or 2; and
n is 1;
or a pharmaceutically acceptable salt or ester thereof.

2. The compound of claim 1, wherein:
A is —$C(R^2)(R^3)$— or $C_3$-$C_6$ cycloalkylene;
$R^1$ is carboxy or hydroxy;
$R^2$ and $R^3$ are independently halogen or $C_1$-$C_4$ alkyl; or $R^2$ and $R^3$, together with the atom to which they are attached, form unsubstituted $C_4$-$C_6$ cycloalkyl or unsubstituted tetrahydro-2H-pyran;
$R^4$ is trifluoroethyl, isobutyl, cyclobutylmethyl, cyclopentylmethyl, cyclopentyl, tetrahydro-2H-pyran-4-yl, (1-hydroxycyclopentyl)methyl, 2-hydroxycyclopentyl, 2-methoxycyclopentyl, 2-oxocyclopentyl, 3-hydroxycyclopentyl, 2-hydroxycyclohexyl, 4-hydroxycyclohexyl, 4-(hydroxymethyl)cyclohexyl, [1-(hydroxymethyl)cyclobutyl]methyl, or [1-(hydroxymethyl)cyclopentyl]methyl;
m is 1 or 2; and
n is 1;
or a pharmaceutically acceptable salt thereof.

3. The compound of claim 1, wherein:
A is —$C(R^2)(R^3)$—;
B is —O—;
$R^1$ is carboxy;
$R^2$ and $R^3$ are independently fluoro, methyl, or ethyl; or $R^2$ and $R^3$, together with the atom to which they are attached, form a ring selected from:

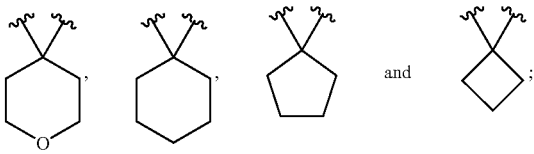

$R^4$ is trifluoroethyl, isobutyl, or cyclobutylmethyl;
m is 1; and
n is 1;
or a pharmaceutically acceptable salt thereof.

4. The compound of claim 1, which is selected from:
4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid;
1-{[4-({[4-(2,2,2-trifluoroethoxy)-1,2-benzisoxazol-3-yl]oxy}methyl)piperidin-1-yl]methyl}cyclobutane-carboxylic acid;
2,2-dimethyl-3-[4-({[4-(2,2,2-trifluoroethoxy)-1,2-benzisoxazol-3-yl]oxy}methyl)piperidin-1-yl]propanoic acid;
trans-4-{[4-({[4-(2,2,2-trifluoroethoxy)-1,2-benzisoxazol-3-yl]oxy}methyl)piperidin-1-yl]methyl}cyclohexanecarboxylic acid;
4-{2-[4-({[4-(2,2,2-trifluoroethoxy)-1,2-benzisoxazol-3-yl]oxy}methyl)piperidin-1-yl]ethyl}tetrahydro-2H-pyran-4-carboxylic acid;
2,2-difluoro-3-[4-({[4-(2,2,2-trifluoroethoxy)-1,2-benzisoxazol-3-yl]oxy}methyl)piperidin-1-yl]propanoic acid;
4-{[4-(2-{[4-(2,2,2-trifluoroethoxy)-1,2-benzisoxazol-3-yl]oxy}ethyl)piperidin-1-yl]methyl}tetrahydro-2H-pyran-4-carboxylic acid;
4-[(4-{[(4-isobutoxy-1,2-benzisoxazol-3-yl)oxy]methyl}piperidin-1-1)methyl]tetrahydro-2H-pyran-4-carboxylic acid;
1-[(4-{[(4-isobutoxy-1,2-benzisoxazol-3-yl)oxy]methyl}piperidin-1-yl)methyl]cyclobutanecarboxylic acid;
4-[2-(4-{[(4-isobutoxy-1,2-benzisoxazol-3-yl)oxy]methyl}piperidin-1-yl)ethyl]tetrahydro-2H-pyran-4-carboxylic acid;
trans-4-[(4-{[(4-isobutoxy-1,2-benzisoxazol-3-yl)oxy]methyl}piperidin-1-yl)methyl]cyclohexanecarboxylic acid;
4-[(4-{[(4-isobutoxy-1,2-benzisoxazol-3-yl)amino]methyl}piperidin-1-yl)methyl]tetrahydro-2H-pyran-4-carboxylic acid;
4-{[4-({[4-(cyclobutylmethoxy)-1,2-benzisoxazol-3-yl]oxy}methyl)piperidin-1-yl]methyl}tetrahydro-2H-pyran-4-carboxylic acid;
3-[4-({[4-(cyclobutylmethoxy)-1,2-benzisoxazol-3-yl]oxy}methyl)piperidin-1-yl]-2,2-dimethylpropanoic acid; or
4-{[4-({[4-(2,2,2-trifluoroethoxy)-1,2-benzisoxazol-3-yl]amino}methyl)piperidin-1-yl]methyl}tetrahydro-2H-pyran-4-carboxylic acid; or
a pharmaceutically acceptable salt of any of the above.

5. The compound of claim 1, which is selected from:
4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid;
1-{[4-({[4-(2,2,2-trifluoroethoxy)-1,2-benzisoxazol-3-yl]oxy}methyl)piperidin-1-yl ]methyl}cyclobutane-carboxylic acid;
2,2-dimethyl-3-[4-({[4-(2,2,2-trifluoroethoxy)-1,2-benzisoxazol-3-yl]oxy}methyl)piperidin-1-yl]-propanoic acid;
trans-4-{[4-({[4-(2,2,2-trifluoroethoxy)-1,2-benzisoxazol-3-yl]oxy}methyl)piperidin-1-yl]methyl}cyclohexanecarboxylic acid;
4-{2-[4-({[4-(2,2,2-trifluoroethoxy)-1,2-benzisoxazol-3-yl]oxy}methyl)piperidin-1-yl]ethyl}tetrahydro-2H-pyran-4-carboxylic acid;
4-[(4-{[(4-isobutoxy-1,2-benzisoxazol-3-yl)oxy]methyl}piperidin-1-1)methyl)tetrahydro-2H-pyran-4-carboxylic acid;
1-(4-{[(4-isobutoxy-1,2-benzisoxazol-3-yl)oxy)methyl}piperidin-1-yl)methyl]cyclobutanecarboxylic acid;
4-[2-(4-{[(4-isobutoxy-1,2-benzisoxazol-3-yl)oxy]methyl}piperidin-1-1)ethyl)tetrahydro-2H-pyran-4-carboxylic acid;

trans-4-[(4-{[(4-isobutoxy-1,2-benzisoxazol-3-yl)oxy]methyl}piperidin-1-yl)methyl]cyclohexanecarboxylic acid;

4-[(4-{[(4-isobutoxy-1,2-benzisoxazol-3-yl)amino]methyl}piperidin-1-yl)methyl]tetrahydro-2H-pyran-4-carboxylic acid;

4-{[4-({[4-(cyclobutylmethoxy)-1,2-benzisoxazol-3-yl]oxy}methyl)piperidin-1-yl]methyl}tetrahydro-2H-pyran-4-carboxylic acid;

3-[4-({[4-(cyclobutylmethoxy)-1,2-benzisoxazol-3-yl]oxy}methyl)piperidin-1-yl]-2,2-dimethylpropanoic acid; or 4-{[4-({[4-(2,2,2-trifluoroethoxy)-1,2-benzisoxazol-3-yl]amino}methyl)piperidin-1-yl]methyl}tetrahydro-2H-pyran-4-carboxylic acid; or a pharmaceutically acceptable salt of any of the above.

6. A pharmaceutical composition comprising the compound of claim 1, or a pharmaceutically acceptable salt thereof, and a pharmaceutically acceptable carrier.

7. A pharmaceutical composition comprising the compound of claim 2, or a pharmaceutically acceptable salt thereof, and a pharmaceutically acceptable carrier.

8. A pharmaceutical composition comprising the compound of claim 3, or a pharmaceutically acceptable salt thereof, and a pharmaceutically acceptable carrier.

9. A method for the treatment of a condition mediated by 5-HT 4 receptor activity in a mammalian subject, which comprises administering to a mammal in need of such treatment a therapeutically effective amount of the compound or pharmaceutically acceptable salt of claim 1, wherein said condition is a gastric motility disorder.

10. The method of claim 9, wherein the gastric motility disorder is selected from the group consisting of irritable bowel syndrome (IBS), constipation, dyspepsia, non-ulcer dyspepsia, and functional dyspepsia.

* * * * *